(12) United States Patent
Halby et al.

(10) Patent No.: US 10,544,156 B2
(45) Date of Patent: Jan. 28, 2020

(54) HEMI-SYNTHETIC TRILOBINE ANALOGS FOR USE AS A DRUG

(71) Applicants: PIERRE FABRE MEDICAMENT, Boulogne-Billancourt (FR); CENTRE NATIONAL DE LA RECHERCHE SCIENTIFIQUE (CNRS), Paris (FR)

(72) Inventors: Ludovic Halby, Toulouse (FR); Yoann Menon, Nailloux (FR); El Bachir Kaloun, Roquettes (FR); Christophe Long, Vielmur sur Agout (FR); Paola B. Arimondo, Toulouse (FR)

(73) Assignees: PIERRE FABRE MEDICAMENT, Boulogne-Billancourt (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/765,048

(22) PCT Filed: Oct. 3, 2016

(86) PCT No.: PCT/EP2016/073581
§ 371 (c)(1),
(2) Date: Mar. 30, 2018

(87) PCT Pub. No.: WO2017/055633
PCT Pub. Date: Apr. 6, 2017

(65) Prior Publication Data
US 2019/0062339 A1 Feb. 28, 2019

(30) Foreign Application Priority Data
Oct. 2, 2015 (EP) .................................... 15306556

(51) Int. Cl.
| C07D 491/12 | (2006.01) |
|---|---|
| C07D 491/22 | (2006.01) |
| A61P 35/00 | (2006.01) |
| C07D 519/00 | (2006.01) |

(52) U.S. Cl.
CPC ............ *C07D 491/22* (2013.01); *A61P 35/00* (2018.01); *C07D 491/12* (2013.01); *C07D 519/00* (2013.01)

(58) Field of Classification Search
CPC ...... C07D 491/22; C07D 491/12; A61P 35/00
See application file for complete search history.

(56) References Cited

FOREIGN PATENT DOCUMENTS

JP        63-179826 A        7/1988

OTHER PUBLICATIONS

Liu et al. Magn. Reson. Chem., 2013, vol. 51, No. 9, pp. 547-579.*
Berman et al., "Regions of Focal DNA Hypermethylation and Long-Range Hypomethylation in Colorectal Cancer Coincide with Nuclear Lamina-Associated Domains," Nat Genet, vol. 44, No. 1, Jan. 28, 2015, pp. 40-46 (17 pages total).
Ceccaldi et al., "C5-DNA Methyltransferase Inhibitors: From Screening to Effects on Zebrafish Embryo Development," ChemBioChem, vol. 12, 2011 (published online Jun. 1, 2011), pp. 1337-1345.
Gros et al., "Development of a Universal Radioactive DNA Methyltransferase Inhibition Test for High-Throughput Screening and Mechanistic Studies," Nucleic Acids Research, vol. 41, No. 19, e185, 2013 (published online Aug. 25, 2013), pp. 1-12.
Halby et al., "Rapid Synthesis of New DNMT Inhibitors Derivatives of Procainamide," ChemBioChem, vol. 13, 2012, pp. 157-165.
International Search Report (Form PCT/ISA/210) for International Application No. PCT/EP2016/073581, dated Jan. 18, 2017.
Inubushi et al., "Studies on the Alkaloids of Menispermaceous Plants. CXCVIII. The Structures of Trilobine and Isotrilobine. (14). Trilobine." Jour Pharm Soc, vol. 83, 1963, pp. 288-292, with Abstract.
Inubushi et al., "Synthesis of Trilobine, Isotrilobine, and Obaberine," Chem. Pharm. Bull., vol. 23, 1977, pp. 1636-1644.
Inubushi et al., "Total Synthesis of Bisbensylisoquinoline Alkaloids, Trilobine and Obaberine," Tetrahedron Letters, No. 33, 1976, pp. 2857-2860.

(Continued)

*Primary Examiner* — Samira J Jean-Louis
(74) *Attorney, Agent, or Firm* — Birch, Stewart, Kolasch & Birch, LLP

(57) ABSTRACT

The invention concerns a compound of the following formula (I) or a pharmaceutically acceptable salt or solvate thereof as well as a pharmaceutical composition containing such a compound, and the use of such a compound as a drug, notably as a DNMT inhibitor, in particular in the treatment of cancer.

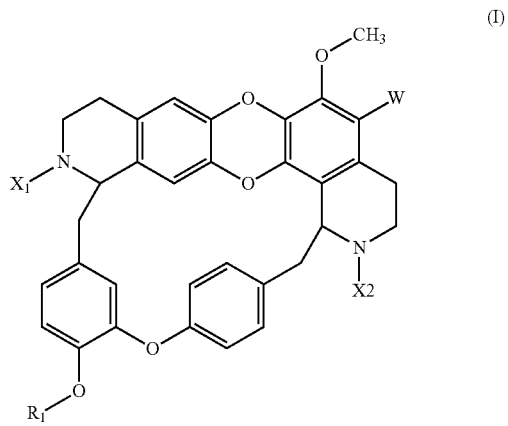

17 Claims, 1 Drawing Sheet
Specification includes a Sequence Listing.

(56) References Cited

OTHER PUBLICATIONS

Kuroda et al., "Antitumor Effect of Bisbenzylisoquinoline Alkaloids," Chem. Pharm. Bull., vol. 24, No. 10, 1976, pp. 2413-2420.
Miranda et al., "Methylation-Sensitive Single-Molecule Analysis of Chromatin Structure," Current Protocols in Molecular Biology, Unit 21.17, published online Jan. 2010, pp. 1-16.
Pardo et al., "MethylViewer: Computational Analysis and Editing for Bisulfite Sequencing and Methyltransferase Accessibility Protocol for Individual Templates (MAPit) Projects," Nucleic Acids Research, vol. 39, No. 1, e5, 2011 (published online Oct. 19, 2010) pp. 1-18.
Rohde et al., "BISMA—Fast and Accurate Bisulfite Sequencing Data Analysis of Individual Clones from Unique and Repetitive Sequences," BMC Bioinformatics, vol. 11, No. 230, 2010, pp. 1-12.
Tackie et al., "Trigillentine and Tricordatine: Two New Bisbenzylisoquinaoline Alkaloids from Triclisia Species," Phytochemistry, vol. 12, 1973, pp. 2509-2511.
Tomita et al., "Studies of the Alkaloids Menispermaceous Plants. CCI. Structure of Trilobine and Isotrilobine. (16). Structure of Trilobine." Yakugaku Zasshi, vol. 83, No. 8, pp. 760-763, with abstract.

* cited by examiner

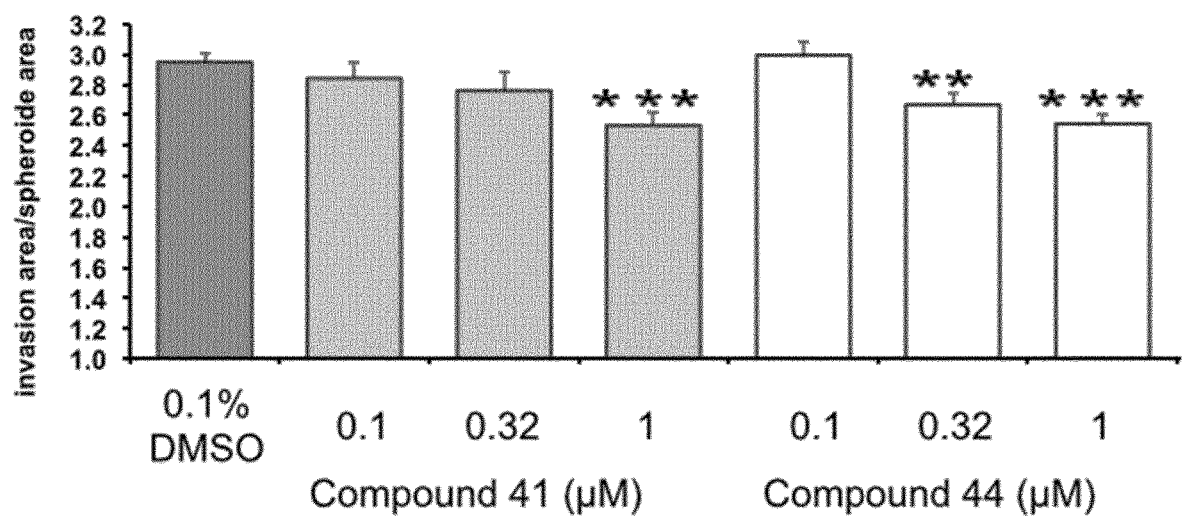
: P-value<0.01, *: P-value<0.001

HEMI-SYNTHETIC TRILOBINE ANALOGS FOR USE AS A DRUG

The present invention relates to hemi-synthetic trilobine analogues useful as DNA methyltransferase (DNMT) inhibitors, notably in the treatment of cancer and in neurological diseases.

Epigenetic modifications play an essential role in the establishment and regulation of differentiation programs that define when and where genes are expressed. Among these modifications, C5 methylation of deoxycytidines (dC) in the DNA was shown to play a key role in the epigenetic regulation in mammals. It is the most stable epigenetic mark and occurs at position 5 of the cytosine ring within mainly CpG dinucleotides. The CpG sites are not distributed randomly across the human genome: they can be regrouped in islands, which are essentially located in promoters, present as repeated sequences, or located in CpG island shores. Hypermethylation of CpG islands located in promoters induces gene silencing while hypomethylation induces gene expression. Most of the CpG sites in the repetitive sequences are methylated, thus preventing chromosomal instability by silencing transposable DNA elements. Furthermore, some CpG islands located in promoters become methylated in a sustainable manner during development, which results in turning gene expression off, a phenomenon observed in X-chromosome inactivation, imprinted genes and developmental genes. Methylation status of the promoters regulates dynamically gene expression through modification of the recognition by transcription factors and the proteins involved in chromatin remodeling.

DNA methyltransferases (DNMTs) catalyse the transfer of a methyl group from S-adenosyl-L-methionine (SAM) to position 5 of the cytosine at the CpG site. Two families of catalytically active DNMTs have been identified: DNMT1, responsible for DNA methylation maintenance during replication, and DNMT3A and 3B, responsible for de novo DNA methylation.

Alterations of DNA methylation patterns lead to various diseases such as cancer and neurological diseases. Cancerous cells present aberrant DNA methylation. In particular, a specific hypermethylation of tumour suppressor genes is observed, inducing their silencing. Restoring their expression by specific inhibition of DNA methylation represents an attractive therapeutic strategy. In addition, it has been shown that demethylating agents prime cancer cells towards immunotherapy and sensitize them towards chemotherapy.

DNMT inhibitors can be divided into two families: nucleoside analogues and non-nucleosides. The first are the most active ones. Two of them are FDA approved: 5-azacytidine (Vidaza®) and 5-aza-2'-deoxycytidine (Dacogene™). Despite their efficiency, poor bioavailability, instability in physiologic media and little selectivity restrict their use. Non-nucleoside analogues present various structures and mechanisms of action. Many of them were shown to target the catalytic site but suffer from lack of specificity and weak activity.

There exists thus a need for novel DNMT inhibitors.

The inventors of the present invention have thus discovered that hemisynthetic bisbenzylisoquinoline alkaloids can be used as DNMT inhibitors. Indeed, in their search of new DNMT inhibitors, they discovered that in the natural extracts of *Cocculus hirsutus* were present potent inhibitors of DNA methylation able to express, in leukaemia KG-1 cells, the luciferase gene under the control of a methylated CMV promoter upon demethylation of the promoter and chromatin decompaction. By a phytochemical approach, the natural bisbenzylisoquinoline alkaloid trilobine and natural analogues were thus identified. The trilobine scaffold was chemically modulated, and the ability of the derivatives to inhibit the DNMTs, to demethylate gene promoters and to induce chromatin opening and gene reexpression, such as of tumour suppressor gene in cancer cells, was characterized.

The present invention concerns thus a compound of the following formula (I), preferably of the following formula (Ia), or a pharmaceutically acceptable salt or solvate thereof:

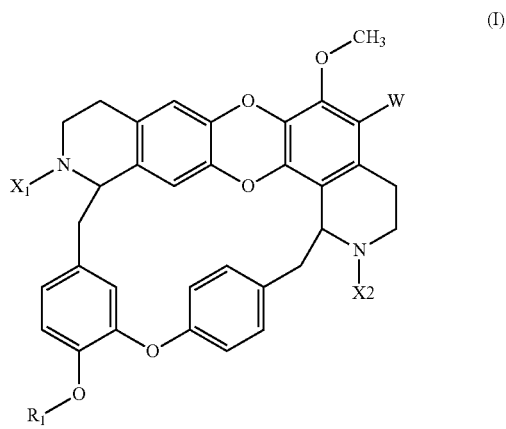

(I)

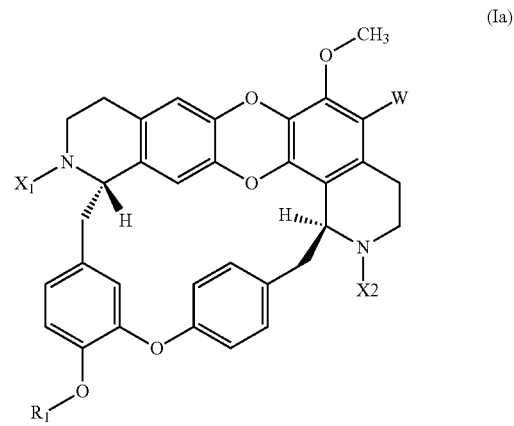

(Ia)

Wherein:
W is H,
$X_1$ and $X_2$ are, independently of each other, H, $(C_1-C_{10})$-alkyl, $(C_1-C_{10})$-alkyl-$R_2$, $(C_2-C_{10})$-alkenyl, $(C_2-C_{10})$-alkenyl-$R_2$ (such as $(C_3-C_{10})$-alkenyl-$R_2$), $CONR_3R_4$, $CSNR_3R_4$, $COR_3$, $COOR_6$, CN, $SOOR_7$, $C(NH)NHR_3$, $(C_1-C_{10})$-alkyl-$(C_5-C_{10})$-aryl or $(C_1-C_{10})$-alkyl-(5-12)-membered-heterocycle,
wherein:
$R_2$ is OH, O—$(C_1-C_{10})$-alkyl, O—$(C_5-C_{10})$-aryl, $NO_2$, CN, $NR_4R_5$, (5-12)-membered-heterocycle, $(C_5-C_{10})$-aryl, O—$((CH_2)_2O)_n$—OH with n=1-3, $CONR_3R_4$, halogen, $COOR_4$, $CF_3$, or $(C_3-C_{12})$-cycloalkyl, in which $(C_5-C_{10})$-aryl and (5-12)-membered-heterocycle are optionally substituted by at least one group selected from $NR_4R_5$, $OR_5$, $(C_1-C_{10})$-alkyl, halogen and oxo (=O),
$R_3$ is H, or a group chosen among $(C_1-C_{10})$-alkyl, $(C_3-C_{12})$-cycloalkyl, $(C_2-C_{10})$-alkenyl, $(C_5-C_{10})$-aryl and a (5-12)-membered-heteroaryl, said group being optionally substituted by at least one group selected from halogen, CN, $NR_4R_5$, mono$(C_1-C_6)$alkyl-amino, di- ($C_1$-$C_6$)-alkyl-amino, $NO_2$, $CONR_4R_5$, $COOR_4$, $CF_3$, $OR_4$ and ($C_1$-$C_{10}$)-alkyl-$R_8$, $R_4$ is H or ($C_1$-$C_{10}$)-alkyl, $R_5$ is H, ($C_1$-$C_{10}$)-alkyl, ($C_5$-$C_{10}$)-aryl or (5-12)-membered-heterocycle, preferably H or ($C_1$-$C_{10}$)-alkyl, $R_6$ is H, ($C_1$-$C_{10}$)-alkyl, ($C_5$-$C_{10}$)-aryl or ($C_1$-$C_{10}$)-alkyl-$R_2$, $R_7$ is ($C_1$-$C_{10}$)-alkyl, ($C_2$-$C_{10}$)-alkenyl, ($C_5$-$C_{10}$)-aryl or a (5-12)-membered-heterocycle, in which the fragments ($C_5$-$C_{10}$)-aryl and (5-12)-membered-heterocycle are optionally substituted by at least one group selected from halogen, CN, $NR_4R_5$, mono($C_1$-$C_6$)alkyl-amino, di-($C_1$-$C_6$)-alkyl-amino, $NO_2$, $CONR_3R_4$, $COOR_4$, $CF_3$ and $OR_4$, and is preferably ($C_1$-$C_{10}$)-alkyl, $R_8$ is H, ($C_1$-$C_{10}$)-alkyl, ($C_5$-$C_{10}$)-aryl or (5-12)-membered-heterocycle, in which ($C_5$-$C_{10}$)-aryl and (5-12)-membered-heterocycle are optionally substituted by at least one group selected from $NR_4R_5$, $OR_5$, ($C_1$-$C_{10}$)-alkyl, halogen and oxo, $R_1$ is hydrogen, ($C_1$-$C_6$)-alkyl, $COR_6$ or $SOOR_9$ with $R_9$ being a ($C_1$-$C_6$)-alkyl group optionally substituted by at least one halogen, with the proviso that $X_1$ is not H or methyl when $X_2$ is H or methyl and R1 is H or methyl.

All stereoisomers, including optical isomers, of formula (I) belong to the invention, as well as the racemic forms.

The term "stereoisomers" used in this invention refers to configurational stereoisomers and includes geometric isomers and optical isomers.

The geometric isomers, also called E/Z isomers or cis-trans isomers, result from the different position of substituents on a double C=C bond which can have a Z or E configuration, also called cis or trans configuration.

The optical isomers result from the different position in space of substituents on an atom (such as a carbon atom) comprising four different substituents. This atom thus represents a chiral or asymmetric center. Optical isomers which are not mirror images of one another are thus designated as "diastereoisomers," and optical isomers which are non-superimposable mirror images are designated as "enantiomers".

An equimolar mixture of two enantiomers of a chiral compound is designated as racemate or racemic mixture.

The expression "($C_1$-$C_{10}$)-alkyl" in the present invention means a linear or branched saturated hydrocarbon chain comprising from 1 to 10 carbon atoms. Examples of alkyl groups covered by the scope of the present invention are methyl, ethyl, propyl, butyl, tert-butyl, isopropyl, decyl groups, etc.

The expression "($C_1$-$C_6$)-alkyl" in the present invention means a linear or branched saturated hydrocarbon chain comprising from 1 to 6 carbon atoms. Examples of alkyl groups covered by the scope of the present invention are methyl, ethyl, propyl, butyl, tert-butyl, isopropyl groups, etc.

The expression "($C_3$-$C_{12}$)-cycloalkyl" means a saturated hydrocarbon ring comprising from 3 to 12 carbon atoms. Examples of cycloalkyl groups covered by the scope of the present invention are cyclopropyl, cyclobutyl, cyclopentyl, cyclohexyl, etc.

The expression "($C_2$-$C_{10}$)-alkenyl" in the present invention means a linear or branched hydrocarbon chain comprising from 2 to 10 carbon atoms containing at least one double bond, like vinyl and allyl groups.

The term "($C_1$-$C_6$)alkylamino", as used in the present invention, refers to an —NHAlk group with Alk representing a ($C_1$-$C_6$)alkyl group as defined above, including, but not limited to, methylamino, ethylamino, n-propylamino, iso-propylamino, n-butylamino, iso-butylamino, sec-butylamino, t-butylamino, n-pentylamino, n-hexylamino, and the like.

The term "di($C_1$-$C_6$)alkylamino", as used in the present invention, refers to an —$NAlk_1Alk_2$ group with $Alk_1$ and $Alk_2$ representing, independently of one another, a ($C_1$-$C_6$) alkyl group as defined above, including, but not limited to, dimethylamino, diethylamino, ethylmethylamino and the like.

The expression "aryl" in the present invention means a cyclic (mono- or polycyclic) aromatic hydrocarbon group comprising between 5 and 12 carbon atoms, preferably between 6 and 10 carbon atoms. Examples of aryl groups covered by the scope of the present invention are phenyl, naphtyl, etc.

The term "($C_1$-$C_{10}$)-alkyl-($C_5$-$C_{10}$)-aryl", as used in the present invention, refers to a ($C_1$-$C_{10}$)-alkyl group as defined above bound to the molecule via an aryl group as defined above. In particular, it can be a tolyl group ($CH_3Ph$).

The expression "(5-12)-membered-heterocycle group" in the present invention means saturated, unsaturated or aromatic hydrocarbon monocycle or bicycle (comprising fused, bridged or spiro rings, notably fused rings) each cycle having 5 or 6 members and 1 to 4, notably 1 or 2, carbon atoms which have been replaced with heteroatoms, such as nitrogen, oxygen or sulphur. Examples of heteroaryl groups covered by the scope of the present invention are pyridine, thiazole, imidazole, pyrazole, quinoline, indole, pyridazine, quinoxaline, dihydrobenzofuran, purine, furan, pyrrole, pyrroline (such as 3-pyrroline), thiophene, isothiazole, oxadiazole, imidazole, oxazole, isoxazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, benzofurane, benzothiophene, indoline, indolizine, benzothiazole, benzothionyle, benzopyranne, benzoxazole, benzo[1,3]dioxole, benzoisoxazole, benzimidazole, chromane, chromene, dihydrobenzofurane, dihydrobenzothiényle, dihydroisoxazole, isoquinoline, dihydrobenzo[1,4]dioxine, imidazo[1,2-a]pyridine, furo[2,3-c]pyridine, 2,3-dihydro-1H-indene, [1,3]dioxolo[4,5-c]pyridine, pyrrolo[1,2-c]pyrimidine, pyrrolo[1,2-a]pyrimidine, tetrahydronaphtalne, benzo[b][1,4]oxazine, etc.

The term "heteroaryl" as used in the present invention refers to an aromatic heterocycle as defined above. It can be more particularly an aromatic monocyclic or bicyclic heterocycle, each cycle comprising 5 or 6 members, such as a pyrrole, a furan, a thiophene, a thiazole, an isothiazole, an oxazole, an isoxazole, an imidazole, a pyrazole, a pyridine, a pyrimidine, a pyridazine, a pyrazine, an indole, a benzofurane, a benzothiophene, a benzothiazole, a benzoxazole, a benzimidazole, a purine, a quinoline, an isoquinoline, a quinazoline or a quinoxaline.

The term "($C_1$-$C_{10}$)-alkyl-(5-12)-membered-heterocycle", as used in the present invention, refers to a ($C_1$-$C_{10}$)-alkyl group as defined above bound to the molecule via a (5-12)-membered-heterocycle as defined above.

The expression "halogen" in the present invention means one of the following atoms: fluorine, chlorine, bromine or iodine.

For the purpose of the invention, the term "pharmaceutically acceptable" is intended to mean what is useful to the preparation of a pharmaceutical composition, and what is generally safe and non toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The expression "pharmaceutically acceptable salts" in the present invention, means all the pharmaceutically acceptable salts of the compounds according to the invention are included within the scope of the invention, in particular the salts of weak acids and of weak bases.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

In particular, it can be the hydrochloride, hydrobromide and trifluoroacetate salts.

Acceptable solvates for the therapeutic use of the compounds of the present invention include conventional solvates such as those formed during the last step of the preparation of the compounds of the invention due to the presence of solvents.

It can be for example an hydrate or an alcoholate such as an ethanolate.

The expression "pharmaceutical composition" in the present invention means any composition comprising an effective dose of a compound of the invention and at least one pharmaceutically acceptable excipient. Said excipients are selected, depending on the pharmaceutical form and the desired method of administration, from the usual excipients known by a person skilled in the art.

In one embodiment, the present invention concerns a compound of formula (Ia) or a pharmaceutically acceptable salt or solvate thereof, wherein:

W=H, $X_1$ and $X_2$ are independently of each other H, $(C_1-C_{10})$-alkyl, $(C_1-C_{10})$-alkyl-$R_2$, $(C_2-C_{10})$-alkenyl, $(C_3-C_{10})$-alkenyl-$R_2$, $CONR_3R_4$, $CSNR_3R_4$, $COR_3$, $COOR_6$, CN, $SOOR_7$, $C(NH)NHR_3$, $(C_1-C_{10})$-alkyl-$(C_5-C_{10})$-aryl or $(C_1-C_{10})$-alkyl-(5-12)-membered-heterocycle, wherein:

$R_2$ is OH, O—$(C_1-C_{10})$-alkyl, O—$(C_5-C_{10})$-aryl, $NO_2$, CN, $NR_4R_5$, (5-12)-membered-heterocycle, —$(C_5-C_{10})$-aryl, —O—$((CH_2)_2O)_n$—OH with n=1-3, $CONR_3R_4$, halogen, $COOR_4$, $CF_3$ or cycloalkyl, $R_3$ is H, $(C_1-C_{10})$-alkyl, $(C_2-C_{10})$-alkenyl, $(C_5-C_{10})$-aryl or a (5-12)-membered-heteroaryl, in which the fragments $(C_5-C_{10})$-aryl and (5-12)-membered-heterocycle can be substituted by at least one group selected from halogen, CN, $NR_4R_5$, mono$(C_1-C_6)$alkyl-amino, di-$(C_1-C_6)$-alkyl-amino, $NO_2$, $CONR_3R_4$, $COOR_4$, $CF_3$ and $OR_4$, $R_4$ is H or $(C_1-C_{10})$-alkyl, $R_5$ is H, $(C_1-C_{10})$-alkyl, $(C_5-C_{10})$-aryl or (5-12)-membered-heterocycle, $R_6$ is H, $(C_1-C_{10})$-alkyl, $(C_5-C_{10})$-aryl or $(C_1-C_{10})$-alkyl-$R_2$, $R_7$ is $(C_1-C_{10})$-alkyl, $(C_2-C_{10})$-alkenyl, $(C_5-C_{10})$-aryl or a (5-12)-membered-heterocycle, in which the fragments $(C_5-C_{10})$-aryl and (5-12)-membered-heterocycle can be substituted by at least one group selected from halogen, CN, $NR_4R_5$, mono$(C_1-C_6)$alkyl-amino, di-$(C_1-C_6)$-alkyl-amino, $NO_2$, $CONR_3R_4$, $COOR_4$, $CF_3$ and $OR_4$, $R_1$ is hydrogen, $(C_1-C_6)$-alkyl, $COR_6$ or $SOOR_9$ with $R_9$ being a $(C_1-C_6)$-alkyl group possibly substituted by at least one halogen, With the proviso that $X_1$ cannot be H or methyl when $X_2$ is H or methyl and R1 is H or methyl and that $X_2$ cannot be H or methyl when $X_1$ is H or methyl and R1 is H or methyl.

In one embodiment, the compound according to the invention is a compound of formula (I), with the proviso that:

when $X_1$ and $R_1$ are methyl groups, $X_2$ is not ethyl, benzyl, or acetyl, and when $X_1$ and $X_2$ are methyl groups, $R_1$ is not ethyl or acetyl.

The compounds deleted with the above mentioned provisos are disclosed in the following documents:

Kuroda et al. *Chem. Pharm. Bull.* 1976, 24(10), 2413-2420,
Inubushi et al. *Tet. Lett.* 1976, 17(33), 2857-2860,
Tomita et al. *J. Pharm. Soc. Japan* 1963, 83(8), 760-763,
Inubushi et al. *J. Pharm. Soc. Japan* 1963, 83(3), 288-292,
Tacki et al. *Phytochem.* 1973, 12(10), 2509-2511, and
Inubushi et al. *Chem. Pharm. Bull.* 1977, 25(7), 1636-1644, all of which concerning fields of application distinct from the one of the present application, except for Kuroda et al., which mentions the antitumoral activity of trilobine and isotrilobine.

According to a particular embodiment, $R_1$ is hydrogen, $(C_1-C_6)$-alkyl, or $SOOR_9$.

According to another particular embodiment, $R_1$ is hydrogen, methyl, or $SOOCF_3$.

According to yet another particular embodiment, $R_1$ is $(C_1-C_6)$-alkyl, preferably methyl.

According to a particular embodiment, $X_1$ and $X_2$ are, independently of each other, H, $(C_1-C_{10})$-alkyl, $(C_1-C_{10})$-alkyl-$R_2$, $CONR_3R_4$, $CSNR_3R_4$, $COR_3$, $COOR_6$, CN or $SOOR_7$.

According to another particular embodiment, $X_1$ and $X_2$ are, independently of each other, H, $(C_1-C_6)$-alkyl, $(C_1-C_6)$-alkyl-$R_2$, $CONR_3R_4$, $CSNR_3R_4$, $COR_3$, $COOR_6$, CN or $SOOR_7$.

According to yet another particular embodiment, at least one of $X_1$ and $X_2$ is not H or $(C_1-C_{10})$-alkyl, notably $X_2$ is not H or $(C_1-C_{10})$-alkyl.

According to still another particular embodiment, $X_1$ and $X_2$ are, independently of each other, H, $(C_1-C_{10})$-alkyl, $(C_1-C_{10})$-alkyl-$R_2$, $CONR_3R_4$, $CSNR_3R_4$, $COR_3$, $COOR_6$, CN or $SOOR_7$, preferably H, $(C_1-C_6)$-alkyl, $(C_1-C_6)$-alkyl-$R_2$, $CONR_3R_4$, $CSNR_3R_4$, $COR_3$, $COOR_6$, CN or $SOOR_7$, with the proviso that at least one of $X_1$ and $X_2$ is not H or $(C_1-C_{10})$-alkyl, notably $X_2$ is not H or $(C_1-C_{10})$-alkyl.

In a preferred embodiment, at least one of $X_1$ and $X_2$, preferably $X_2$, is $CONR_3R_4$ or $CSNR_3R_4$, preferably $CONR_3R_4$.

Advantageously, $R_2$ is CN, $NR_4R_5$ or a (5-12)-membered-heterocycle optionally substituted by at least one group selected from $NR_4R_5$, $OR_5$, $(C_1-C_{10})$-alkyl, halogen and oxo (=O), preferably by $NR_4R_5$.

More advantageously, $R_2$ is CN or a (5-12)-membered-heterocycle optionally substituted by at least one group selected from $NR_4R_5$, $OR_5$, $(C_1-C_6)$-alkyl, halogen and oxo (=O), preferably by $NR_4R_5$. In this case, the (5-12)-membered-heterocycle can be more particularly a monocyclic or bicyclic heteroaryl containing 1 to 5, notably 1 to 4 nitrogen atoms, each cycle comprising 5 or 6 members, such as a pyrrole, an imidazole, a pyrazole, a pyridine, a pyrimidine, a pyridazine, a pyrazine, an indole, a benzimidazole, a purine, a quinoline, an isoquinoline, a cinnoline, a quinazoline or a quinoxaline.

Even more particularly, $R_2$ is CN or a purine optionally substituted by at least one group selected from $NR_4R_5$, $OR_5$, $(C_1-C_{10})$-alkyl and halogen, preferably by $NR_4R_5$, such as by $NH_2$.

In particular, $R_3$ is H, or a group chosen among $(C_1-C_{10})$-alkyl, $(C_3-C_{12})$-cycloalkyl, $(C_2-C_{10})$-alkenyl and $(C_6-C_{10})$-aryl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_{10})$-alkyl-$R_8$, such as selected from $NR_4R_5$, di-$(C_1-C_6)$-alkyl-amino and $(C_1-C_6)$-alkyl-$R_8$.

More particularly, $R_3$ is H, or a group chosen among $(C_1-C_6)$-alkyl, $(C_3-C_{12})$-cycloalkyl, and $(C_2-C_{10})$-alkenyl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_6)$-alkyl-$R_8$, such as selected from $NR_4R_5$, di-$(C_1-C_6)$-alkyl-amino and $(C_1-C_6)$-alkyl-$R_8$.

Even more particularly, $R_3$ is H, or a group chosen among methyl, ethyl, propyl, cyclohexyl, vinyl and propenyl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_6)$-alkyl-$R_8$, such as selected from $NR_4R_5$, di-$(C_1-C_6)$-alkyl-amino and $(C_1-C_6)$-alkyl-$R_8$.

Yet even more particularly, $R_3$ is H, methyl, chloro-ethyl, diethylaminopropyl, (2,5-dioxo-3-pyrroline)-methyl-cyclohexyl, vinyl or dimethylaminopropenyl.

$R_4$ can be H or $(C_1-C_6)$-alkyl, in particular $R_4$ is H, methyl or ethyl, preferably $R_4$ is H.

Preferably, $R_5$ is H or $(C_1-C_{10})$-alkyl, in particular, $R_5$ is H or $(C_1-C_6)$-alkyl, and can be H, methyl, or ethyl.

In particular, $R_6$ is $(C_1-C_{10})$-alkyl-$R_2$, such as $(C_1-C_6)$-alkyl-$R_2$, for example $(CH_2)_m$—$R_2$ with m=1-4, such as propyl-$R_2$ or butyl-$R_2$.

Advantageously, $R_7$ is $(C_1-C_{10})$-alkyl, such as $(C_1-C_6)$-alkyl, and can be methyl.

Preferably, $R_8$ is a (5-12)-membered-heterocycle, optionally substituted by at least one group selected from $NR_4R_5$, $OR_5$, $(C_1-C_{10})$-alkyl, halogen and oxo, such as by at least one oxo.

In this case, the (5-12)-membered-heterocycle can be a saturated, unsaturated or aromatic hydrocarbon monocycle or bicycle, each cycle having 5 or 6 members and 1 to 4, notably 1 or 2, carbon atoms which have been replaced with heteroatoms selected from nitrogen, oxygen and sulfur atoms, such as nitrogen atom. In particular, the heterocycle can be a pyrroline, such as a 3-pyrroline. For example, $R_8$ can be 2,5-dioxo-3-pyrroline.

In a first embodiment, $X_1$ and $X_2$ are, independently of each other, H, $(C_1-C_{10})$-alkyl, $(C_1-C_{10})$-alkyl-$R_2$, $CONR_3R_4$, $CSNR_3R_4$, $COR_3$, $COOR_6$, CN, or $SOOR_7$, wherein:
$R_2$ is CN or a (5-12)-membered-heterocycle, optionally substituted by at least one $NR_4R_5$, $OR_5$, $(C_1-C_{10})$-alkyl and halogen, preferably by $NR_4R_5$,
$R_3$ is H, or a group chosen among $(C_1-C_{10})$-alkyl, $(C_3-C_{12})$-cycloalkyl and $(C_2-C_{10})$-alkenyl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_{10})$-alkyl-$R_8$, preferably by halogen, $NR_4R_5$, di-$(C_1-C_6)$-alkyl-amino and $(C_1-C_{10})$-alkyl-$R_8$,
$R_4$ is H or $(C_1-C_{10})$-alkyl,
$R_5$ is H or $(C_1-C_{10})$-alkyl,
$R_6$ is $(C_1-C_{10})$-alkyl-$R_2$,
$R_7$ is $(C_1-C_{10})$-alkyl, and
$R_8$ is a (5-12)-membered-heterocycle, substituted by at least one group selected from $NR_4R_5$, $OR_5$, $(C_1-C_{10})$-alkyl, halogen and oxo, preferably by at least one oxo group.

In a second embodiment, $X_1$ and $X_2$ are, independently of each other, H, $(C_1-C_{10})$-alkyl, $(C_1-C_{10})$-alkyl-$R_2$, $CONR_3R_4$, $CSNR_3R_4$, $COR_3$, $COOR_6$, CN, or $SOOR_7$, and at least one of $X_1$ and $X_2$ is not H or $(C_1-C_{10})$-alkyl, preferably $X_2$ is not H or $(C_1-C_{10})$-alkyl,
wherein:
$R_2$ is CN or a (5-12)-membered-heterocycle, optionally substituted by at least one $NR_4R_5$, $OR_5$, $(C_1-C_{10})$-alkyl and halogen, preferably by $NR_4R_5$,
$R_3$ is H, or a group chosen among $(C_1-C_{10})$-alkyl, $(C_3-C_{12})$-cycloalkyl and $(C_2-C_{10})$-alkenyl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_{10})$-alkyl-$R_8$, preferably by halogen, $NR_4R_5$, di-$(C_1-C_6)$-alkyl-amino and $(C_1-C_{10})$-alkyl-$R_8$,
$R_4$ is H or $(C_1-C_{10})$-alkyl,
$R_5$ is H or $(C_1-C_{10})$-alkyl,
$R_6$ is $(C_1-C_{10})$-alkyl-$R_2$,
$R_7$ is $(C_1-C_{10})$-alkyl, and
$R_8$ is a (5-12)-membered-heterocycle, substituted by at least one group selected from $NR_4R_5$, $OR_5$, $(C_1-C_{10})$-alkyl, halogen and oxo, preferably by at least one oxo group,
with the proviso that $X_2$ is not H or $(C_1-C_{10})$-alkyl.

In a third embodiment, $X_1$ is H, $(C_1-C_{10})$-alkyl, $(C_1-C_{10})$-alkyl-$R_2$, $CONR_3R_4$, $CSNR_3R_4$, $COR_3$, $COOR_6$, CN, or $SOOR_7$, and $X_2$, is $CONR_3R_4$ or $CSNR_3R_4$, preferably $CONR_3R_4$,
wherein:
$R_2$ is CN or a (5-12)-membered-heterocycle, optionally substituted by at least one $NR_4R_5$, $OR_5$, $(C_1-C_{10})$-alkyl and halogen, preferably by $NR_4R_5$,
$R_3$ is H, or a group chosen among $(C_1-C_{10})$-alkyl, $(C_3-C_{12})$-cycloalkyl and $(C_2-C_{10})$-alkenyl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_{10})$-alkyl-$R_8$, preferably by halogen, $NR_4R_5$, di-$(C_1-C_6)$-alkyl-amino and $(C_1-C_{10})$-alkyl-$R_8$,
$R_4$ is H or $(C_1-C_{10})$-alkyl,
$R_5$ is H or $(C_1-C_{10})$-alkyl,
$R_6$ is $(C_1-C_{10})$-alkyl-$R_2$,
$R_7$ is $(C_1-C_{10})$-alkyl, and
$R_8$ is a (5-12)-membered-heterocycle, substituted by at least one group selected from $NR_4R_5$, $OR_5$, $(C_1-C_{10})$-alkyl, halogen and oxo, preferably by at least one oxo group.

In the above first, second and third above mentioned embodiments, the (5-12)-membered-heterocycle is preferably:
in the definition of $R_2$, a monocyclic or bicyclic heteroaryl containing 1 to 5, notably 1 to 4 nitrogen atoms, each cycle comprising 5 or 6 members, such as a pyrrole, an imidazole, a pyrazole, a pyridine, a pyrimidine, a pyridazine, a pyrazine, an indole, a benzimidazole, a purine, a quinoline, an isoquinoline, a cinnoline, a quinazoline or a quinoxaline, preferably a purine;

in the definition of $R_8$, a saturated, unsaturated or aromatic hydrocarbon monocycle or bicycle, each cycle having 5 or 6 members and 1 to 4, notably 1 or 2, carbon atoms which have been replaced with heteroatoms selected from nitrogen, oxygen and sulfur atoms, such as nitrogen atom, preferably a pyrroline, such as a 3-pyrroline.

According to another aspect of the present invention, the new hemi-synthetic bis(benzylisoquinoline) analogues of formula I correspond to those of formula I wherein:

$X_1$ is methyl, a 9-membered heteroaryl $(C_1$-$C_6)$-alkyl possibly substituted by an amino group, $CSNHR_3$ with $R_3$ being a $(C_1$-$C_6)$-alkyl group possibly substituted by a di-$(C_1$-$C_6)$alkyl-amino group, $CONHR_3$ with $R_3$ being a $(C_1$-$C_6)$-alkyl group possibly substituted by a di-$(C_1$-$C_6)$alkyl-amino group, and $R_1$ is a methyl group, in particular $R_1$ and $R_2$ are methyl groups.

According to yet another aspect of the present invention, the new hemi-synthetic bis(benzylisoquinoline) analogues of formula I correspond to those of formula I wherein:

$X_1$ and $R_1$ are methyl groups, in particular $X_1$, $R_1$ and $R_2$ are methyl groups, and $X_2$ is $CSNHR_3$ with $R_3$ being a $(C_1$-$C_6)$-alkyl group possibly substituted by a di-$(C_1$-$C_6)$-alkyl-amino group.

The compounds of the present invention may be selected from the compounds 10-22, 24-28, 30-33, 41-51 and 53-54 and the pharmaceutically acceptable salts and solvates thereof.

The present invention relates also to a compound of formula (I) such as defined above, for use as a drug, notably intented for the treatment of cancer and of neurological diseases, in particular cancer, or intented for cell reprogramming, notably for the treatment of cancer.

In one embodiment, the compounds of formula (I) such as defined above are DNA methyl transferase (DNMT) inhibitors.

Consequently, the present invention relates also to a compound of formula (I) such as defined above, for use as a DNMT inhibitor.

The present invention relates also to a compound of formula (I) such as defined above, for use as a drug intented for inhibiting DNMT.

According to the invention, the expression "DNMT inhibitor" refers to molecules that are able to reduce the DNMT activity. Preferentially, the use of a DNMT inhibitor according to the invention makes it possible to inhibit the activity of said DNMT. The compounds showed also their properties of inhibitors of DNA methylation in cells. The DNMT inhibitory activity can be tested by measuring the expression of a CMV-Luc gene, notably as described in example II.3 of the present application, or by measuring the inhibition of hDNMT3A or hDNMT1 enzymes, notably as described in example II.1 and II.2 of the present application. DNMT inhibitors according to the invention are thus able to reprogramming cells towards less aggressive state.

Also, the present invention relates to a compound of formula (I) such as defined above, for use as a drug, as a DNMT inhibitor for use in a drug for treatment of cancer and neurological diseases, and cell reprogramming, notably intended for the treatment of cancer.

The present invention also relates to the use of a compound of formula (I) such as defined above, for the manufacture of a drug, notably intended for the treatment of cancer.

The present invention also relates to the use of a compound of formula (I) such as defined above, for the manufacture of a drug intended for inhibiting DNMT.

The present invention also relates to a method for the treatment of cancer, comprising the administration to a person in need thereof of an effective dose of a compound of formula (I) such as defined above.

In particular the compound relates to its use in combination to prime cells towards chemotherapy or immunotherapy.

The present invention also relates to a method for inhibiting DNMT, comprising the administration to a person in need thereof of an effective dose of a compound of formula (I) such as defined above.

The neurological disease according to the invention may be more particularly schizophrenia and neurodegenerative diseases.

The cancer according to the invention may be colon cancer; hepatocarcinoma; melanoma; breast cancer; ovarian cancer; kidney cancer; liver cancer; pancreatic cancer; prostate cancer; glioblastoma; lung cancer, such as non-small cell lung cancer; neuroblastoma; myofibroblastic tumor; lymphoma, such as B- and T-cell lymphoma or anaplastic large-cell lymphoma; leukemia, such as AML (acute myeloid leukemia), MDS (myelodysplastic syndrome), CMML (chronic myelomonocytic leukemia) and CML (chronic myeloid leukemia); and multiple myeloma.

The cancer may be more particularly colon cancer, hepatocarcinoma, melanoma, breast cancer, ovarian cancer, kidney cancer, liver cancer, pancreatic cancer, prostate cancer, glioblastoma, non-small cell lung cancer, neuroblastoma, myofibroblastic tumor, B- and T-cell lymphoma or anaplastic large-cell lymphoma, leukemia (AML, MDS, CMML, CML), multiple myeloma. The cancer can be in particular a DNMT-overexpressing cancer.

The present invention also relates to a pharmaceutical composition comprising at least one compound of formula (I) such as defined above, and at least one pharmaceutically acceptable excipient.

The pharmaceutical compositions according to the invention may be formulated notably for oral administration, topical administration or for injection, wherein said compositions are intended for mammals, including humans.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. It may be necessary to use doses outside these ranges as determined by the person skilled in the art.

The active ingredient may be administered for several cycles to keep the reprogramming of the cell.

The pharmaceutical compositions according to the invention may further comprise at least one other active ingredient, such as an anticancer agent.

The present invention relates also to a pharmaceutical composition comprising:

(i) at least one compound of formula (I) such as defined above, and (ii) at least one other active ingredient, such as an anticancer agent, as a combination product for simultaneous, separate or sequential use in the treatment of cancer.

This combined active ingredient can be selected from the group consisting of:

Cytotoxic agents such as doxorubicin, R-CHOP (Rituximab, Cyclophosphamide, Hydroxydaunorubicin, Oncovin, Prednisone or Prednisolone), PARP (Poly ADP Ribose Polymerase) inhibitors, etoposide, cisplatin, vinorelbine, vinflunine, bortezomib, etc.;

Other epigenetics drugs such as:
Inhibitors histone deacetylase (HDACi, such as inhibitors of HDAC 1 & 2),
Inhibitors of chromatin remodeler (such as CHD4),
Inhibitors of histone modifiers (such as demethylases JARDI1A/B or methylases EZH2);

Immunotherapies such as antiCTL4 or antiPD1.

The present invention also relates to a pharmaceutical composition such as defined above for use as a drug, notably intended for the treatment of cancer.

The present invention also relates to methods for the preparation of the compounds of formula (I) according to the invention.

The compounds according to the present invention can be obtained by chemical synthesis as by one of the methods described below.

LEGEND OF THE FIGURE

FIG. 1: Fluorescent invasion area for spheroids in presence of DMSO or of 0.1, 0.32 or 1 µM of compound 41 or 44.

EXAMPLES

The examples, which follow, illustrate the invention without limiting its scope in any way.

The following abbreviations have been used in the following examples.
BSA: bovine serum albumin
CMV: cytomegalovirus
CpG: deoxycytidine-phosphate-deoxyguanosine
DMF: Dimethylformamide
DMSO: Dimethylsulfoxide
DNMT: C5 DNA methyltransferase
EMEM: Eagle's Minimum Essential Medium
EDTA: Ethylenediaminetetraacetic acid
HEPES: 4-(2-Hydroxyethyl)-1-piperazineethanesulfonic acid
HPLC: High Performance Liquid Chromatography
HRMS: High Resolution Mass Spectrometry
luc: luciferase
NMR: Nuclear Magnetic Resonance
PBS: Phosphate buffered saline
PCR: Polymerase Chain Reaction
PBST: Phosphate buffered saline+Tween-20
RT: Room temperature
SAH: S-adenosyl-L-homocysteine
SAM: S-adenosyl-L-methionine
THF: Tetrahydrofuran
TLC: Thin Layer Chromatography

Example I. Synthesis of Examples of Compounds of Formula According to the Present Invention

Example 1: Product 10

To a solution of trilobine (1) (6 mg-10.68 µmol) in 300 µL of tetrahydrofuran (THF) was added ethyl formate (46 µL-570 µmol) and 1 drop of acetic acid. The mixture was stirred 24 h at RT in inert argon atmosphere. The reaction mixture was concentrated under reduced pressure and the residue was purified by semi-preparative X-Terra RP-18 HPLC, eluting with a linear gradient H₂O/MeCN with 1% formic acid (95:5 to 50:50), to give 10 as a mixture of two rotamers in proportion 50/50 (0.4 mg, 0.678 µmol, 6%).

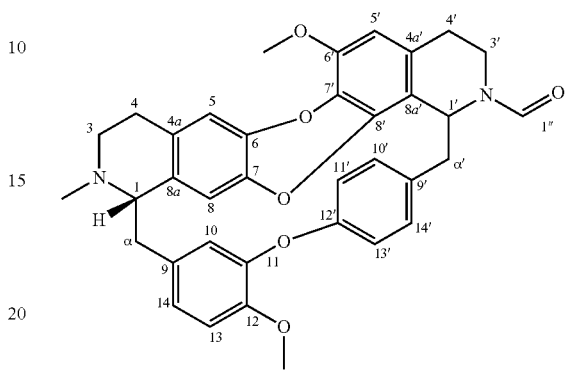

(10)

$^1$H NMR (500 MHz, CDCl$_3$) δ 8.51/8.24 (1H, s, H-1"), 8.00/7.43 (1H, dd, J=8.3 Hz, J=2.2 Hz, H-14'), 7.27/7.02 (1H, m, H-13'), 7.09 (m, H-10'), 6.97-6.87 (3H, dd, H-11', H-13, H-14), 6.71/6.67 (1H, s, H-5), 6.62/6.55 (1H, d, J=1.9 Hz, H-10), 6.42/6.36 (1H, s, H-5'), 6.39-6.24 (1H, s, H-8), 5.76/4.95 (1H, br d, J=5.5 Hz, H-1'), 4.23 (1H, m, H-3'), 3.96/3.95 (3H, s, 12-OMe), 3.89/3.88 (3H, s, 6'-OMe), 3.74 (2H, m, H-3'), 3.69/3.61 (1H, br, H-1), 3.44 (1H, m, H-3'), 3.28-2.96 (4H, m, H-α, H-α'), 2.95/2.73 (6H, m, H-3, H-4, H-4'), 2.43/2.42 (3H, s, N2-Me).

$^{13}$C NMR (125 MHz, CDCl$_3$) δ 161.2/160.9 (C-1"), 154.6 (C-12'), 150.2 (C-11), 147.6 (C-12), 146.9 (C-6'), 139.7 (C-6 or C-7 or C-8'), 139.6 (C-6 or C-7 or C-8'), 139.2 (C-6 or C-7 or C-8'), 137.3 (C-9'), 133.2 (C-9), 132.2 (C-8a), 131.4 (C-10'), 130.9/129.2 (C-14'), 130.2 (C-7'), 130.0 (C-4a), 127.7 (C-4a'), 123.5/123.1 (C-13'), 121.7/121.9 (C-11' and C-14), 118.0/118.9 (C-8a'), 117.8/117.4 (C-10), 116.2/116.0 (C-5), 114.7/114.5 (C-8), 113.0/112.5 (C-13), 107.3/107.0 (C-5'), 65.2/65.7 (C-1), 56.6 (C-6'-OMe), 56.4 (C-12-OMe), 55.5/49.2 (C-1'), 50.4/49.9 (C-3), 46.2/45.6 (C-α'), 41.1/36.4 (C-3'), 40.2 (C—N2-Me), 38.0/38.5 (C-α), 29.2/27.1 (C-4'), 26.4/26.2 (C-4).

HRMS-ESI (m/z) calculated for C$_{36}$H$_{35}$N$_2$O$_6$ [M+H]$^+$: 591.2490; Found: 591.2431.

Example 2: Product 11

To a solution of trilobine (1) (6 mg-10.68 µmol) in 200 µL of dichloromethane (CH$_2$Cl$_2$) and 200 µL of propan-2-ol, was added isocyanatotrimethylsilane (2 mg-17.36 µmol). The mixture was stirred 16 h at RT in inert argon atmosphere. The reaction mixture was concentrated under reduced pressure and the residue was purified by semi-preparative X-Terra RP-18 HPLC, eluting with a linear gradient H$_2$O/MeCN with 0.02% trimethylamine (80:20 to 0:100). The collected fractions were evaporated under reduced pressure, to give 11 (4.7 mg, 7.77 µmol, 73%).

(11)

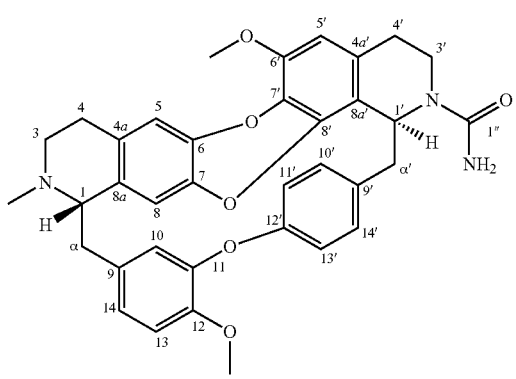

¹H NMR (500 MHz, CDCl₃) δ 7.96 (1H, br d, J=7.7 Hz, H-14'), 7.19 (1H, dd, J=8.5 Hz, J=2.6 Hz, H-13'), 7.05 (1H, br dd, J=8.1 Hz, J=1.8 Hz, H-10'), 6.96 (1H, dd, J=8.1 Hz, J=2.6 Hz, H-11'), 6.90 (2H, s, H-13, H-14), 6.64 (1H, s, H-10), 6.62 (1H, s, H-5), 6.39 (1H, s, H-5'), 6.25 (1H, s, H-8), 5.57 (1H, br, H-1'), 4.60 (2H, s, 1"-N$H_2$), 3.96 (3H, s, 12-O$Me$), 3.88 (3H, s, 6'-O$Me$), 3.71-3.57 (2H, m, H-3'), 3.32 (1H, d, J=14.2 Hz, H-α'), 3.27 (1H, br, H-1), 2.96-2.81 (6H, m, H-3, H-4', H-α, H-α'), 2.78-2.71 (3H, m, H-3, H-4), 2.61-2.54 (1H, m, H-4), 2.34 (3H, s, N2-$Me$).

¹³C NMR (125 MHz, CDCl₃) δ 157.4 (C-1"), 154.9 (C-12'), 150.1 (C-11), 147.5 (C-12), 146.7 (C-6'), 139.7 (C-6 or C-7), 139.3 (C-6 or C-7), 139.1 (C-8'), 137.6 (C-9'), 135.1 (C-9), 134.9 (C-8a), 130.9 (C-14'), 130.8 (C-4a), 130.6 (C-10'), 130.2 (C-7'), 128.5 (C-4a'), 123.1 (C-13'), 122.2 (C-14), 121.5 (C-11'), 120.1 (C-8a'), 117.7 (C-10), 115.9 (C-5), 114.5 (C-8), 112.3 (C-13), 106.6 (C-5'), 67.1 (C-1), 56.6 (C-6'-O$Me$), 56.4 (C-12-O$Me$), 52.2 (C-1'), 51.2 (C-3), 46.1 (C-α'), 41.8 (C—N2-$Me$), 41.1 (C-3'), 40.3 (C-α), 28.0 (C-4'), 27.4 (C-4).

HRMS-ESI (m/z) calculated for $C_{36}H_{33}N_3O_6$ [M+H]⁺: 606.2599; Found: 606.2598.

Example 3: Product 12

To a solution of trilobine (1) (6 mg-10.68 μmol) in 300 μL of THF was added N,N-diisopropylethylamine (2 μL-11.78 μmol) and N,N-diethyl-3-isothiocyanatopropan-1-amine (2 μL-11.07 μmol). The mixture was stirred 16 h at RT in inert argon atmosphere. The reaction mixture was concentrated under reduced pressure and the residue was purified by semi-preparative X-Terra RP-18 HPLC, eluting with a linear gradient H₂O/MeCN with 1% formic acid (80:20 to 0:100), to give 12 (2 mg, 2.72 μmol, 26%).

(12)

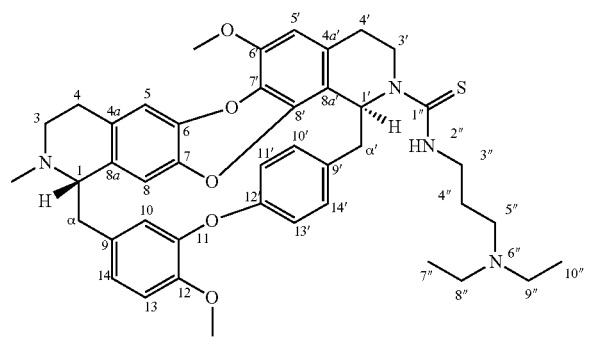

¹H NMR (500 MHz, CDCl₃) δ 8.16 (1H, br, H-14'), 7.92 (1H, br, 2"-NH), 7.13 (1H, dd, J=8.3 Hz, J=2.3 Hz, H-13'), 6.96 (1H, dd, J=8.4 Hz, J=2.0 Hz, H-11'), 6.90-6.84 (3H, m, H-10', H-13, H-14), 6.68 (1H, s, H-5), 6.66 (1H, d, J=1.9 Hz, H-10), 6.63 (1H, br, H-1'), 6.47 (1H, s, H-5'), 6.44 (1H, s, H-8), 3.93 (3H, s, 12-O$Me$), 3.90 (3H, s, 6'-O$Me$), 3.89-3.82 (6H, m, H-3', H-3", H-5"), 3.63 (1H, br, H-1), 3.43 (1H, d, J=12.7 Hz, H-α'), 3.17-2.85 (9H, m, H-4', H-8", H-9", H-α, H-α'), 2.66-2.74 (2H, m, H-4), 2.65-2.58 (2H, m, H-3), 2.28 (3H, s, N2-$Me$), 2.15-2.02 (2H, br, H-4"), 1.20 (6H, br t, J=6.5 Hz, H-7", H-10").

¹³C NMR (125 MHz, CDCl₃) δ 180.9 (C-1"), 154.8 (C-12'), 149.5 (C-11), 147.9 (C-12), 146.8 (C-6'), 140.7 (C-6 or C-7), 139.5 (C-6 or C-7), 139.2 (C-8'), 136.0 (C-9), 132.7 (C-9), 132.3 (C-14'), 131.7 (C-4a), 130.6 (C-8a), 130.4 (C-10'), 130.0 (C-4a' and C-7'), 132.1 (C-11'), 122.7 (C-13'), 121.1 (C-14), 119.4 (C-8a'), 117.7 (C-10), 115.7 (C-5), 115.0 (C-8), 112.6 (C-13), 106.7 (C-5'), 64.3 (C-1), 56.6 (C-6'-O$Me$), 56.3 (C-12-O$Me$), 56.1 (C-1'), 51.4 (C-3), 45.9 (C-8" and C-9"), 44.6 (C-α'), 44.2 (C-3' and C-3" and C-5"), 39.2 (C—N2-$Me$), 36.3 (C-α), 28.2 (C-4'), 26.4 (C-4), 23.9 (C-4"), 9.0 (C7" and C-10").

HRMS-ESI (m/z) calculated for $C_{43}H_{51}N_4O_5S$ [M+H]⁺: 735.3575; Found: 735.3572.

Example 4: Product 13

To a solution of trilobine (1) (6 mg-10.68 μmol) in 400 μL of CH₂Cl₂ was added methanesulfonyl chlorure (2 μL-25.84 μmol) and N,N-diisopropylethylamine (4.5 μL-26.46 μmol). The mixture was stirred 12 h at RT in inert argon atmosphere. The reaction mixture was concentrated under reduced pressure and the residue was purified by HPLC semi-preparative X-Terra RP-18, eluting with a linear gradient H₂O/MeCN with 0.02% triethylamine (75:25 to 20:80), to give 13 (1.2 mg, 1.88 μmol, 18%).

(13)

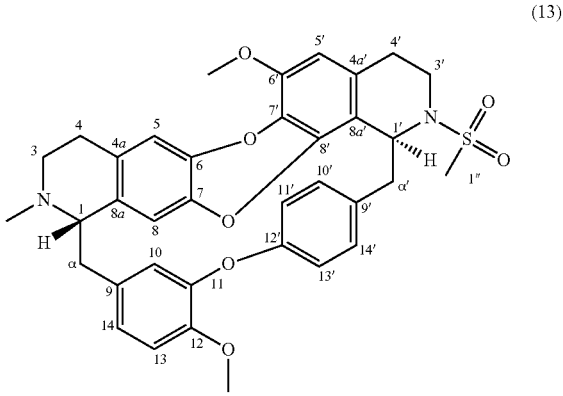 [SMILES: COc1ccc2cc1Oc1ccc(cc1)C[C@H]1c3c(cc(OC)c4c3Oc3cc5c(cc3O4)CCN(C)[C@H]5C2)CCN1S(C)(=O)=O]

¹H NMR (500 MHz, CDCl₃) δ 8.00 (1H, dd, J=8.5 Hz, J=2.2 Hz, H-14'), 7.27-7.25 (1H, br, H-13'), 7.12 (1H, dd, J=7.9 Hz, J=1.9 Hz, H-10'), 7.02 (1H, dd, J=8.3 Hz, J=2.6 Hz, H-11'), 6.87-6.90 (2H, m, H-13, H-14), 6.65 (1H, s, H-5), 6.60 (1H, d, J=1.7 Hz, H-10), 6.39 (1H, s, H-5'), 6.19 (1H, s, H-8), 5.29 (1H, br, H-1'), 4.04 (1H, m, H-3'), 3.99 (3H, s, 12-O$Me$), 3.90 (3H, s, 6'-O$Me$), 3.57-3.63 (1H, m, H-3'), 3.50 (1H, br d, J=14.9 Hz, H-α'), 3.27 (1H, br t, J=3.3 Hz, H-1), 3.04-2.75 (7H, m, H-3, H-4, H-4', H-α, H-α'), 2.78 (3H, s, 1"-S-$Me$), 2.67-2.60 (2H, m, H-3, H-4), 2.41 (3H, s, N2-$Me$).

$^{13}$C NMR (125 MHz, CDCl$_3$) δ 154.8 (C-12'), 150.3 (C-11), 147.4 (C-12), 147.1 (C-6'), 139.5 (C-6 or C-7), 139.2 (C-6 or C-7), 139.1 (C-8'), 137.6 (C-9'), 137.8 (C-8a), 135.2 (C-9), 130.9 (C-10'), 130.8 (C-4a), 130.3 (C-7'), 129.8 (C-14'), 126.8 (C-4a'), 123.4 (13'), 122.0 (C-14), 121.8 (C-11'), 119.0 (C-8a'), 117.5 (C-10), 116.0 (C-5), 114.5 (C-8), 112.2 (C-13), 107.0 (C-5'), 67.6 (C-1), 56.6 (C-6'-OMe), 56.4 (C-12-OMe), 54.1 (C-1'), 50.7 (C-3), 45.8 (C-α'), 42.7 (C—N2-Me), 41.1 (C-α), 40.3 (C-3'), 39.7 (C1"-S-Me), 27.8 (C-4), 26.3 (C-4').

HRMS-ESI (m/z) calculated for C$_{36}$H$_{37}$N$_2$O$_7$S [M+H]$^+$: 641.2316; Found: 641.2332.

Example 5: Product 14

To a solution of trilobine (1) (6 mg-10.68 μmol) in 300 μL of THF was added methyl isothiocyanate (1 μL-14.62 μmol) and N,N-diisopropylethylamine (2 μL-11.76 μmol). The mixture was stirred 12 h at RT in inert argon atmosphere. The reaction mixture was concentrated under reduced pressure and the residue was purified by semi-preparative X-Terra RP-18 HPLC, eluting with a linear gradient H$_2$O/MeCN with 0.02% triethylamine (50:50 to 0:100), to give 14 (3.8 mg, 5.98 μmol, 56%).

(14)

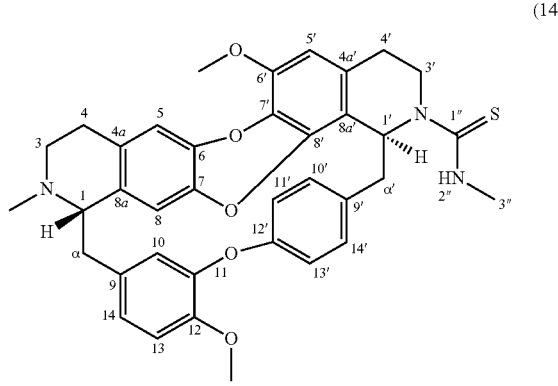

$^1$H NMR (500 MHz, CDCl$_3$) δ 8.04 (1H, br, H-14'), 7.14 (1H, dd, J=8.6 Hz, J=2.2 Hz, H-13'), 6.97-6.90 (4H, m, H-10', H-11', H-13, H-14), 6.74 (1H, d, J=1.8 Hz, H-10), 6.66 (1H, s, H-5), 6.46 (1H, s, H-5'), 6.39 (1H, s, H-8), 5.29 (1H, br, H-1'), 6.37 (1H, m, H-3'), 5.70 (1H, br, 2"-NH), 3.96 (3H, s, 12-OMe), 3.91 (3H, s, 6'-OMe), 3.84-3.89 (1H, m, H-3'), 3.50 (1H, br d, J=13.7 Hz, H-α'), 3.37 (1H, br d, J=5.5 Hz, H-1), 3.26 (3H, d, J=4.5 Hz, 3"-NH-Me), 3.10 (1H, m, H-4'), 3.06-2.92 (5H, m, H-3, H-4', H-α, H-α'), 2.79-2.72 (2H, m, H-3, H-4), 2.56 (1H, m, H-4), ☐ 2.26 (3H, s, N2-Me).

$^{13}$C NMR (125 MHz, CDCl$_3$) δ 182.0 (C-1"), 155.6 (C-12'), 149.6 (C-11), 147.9 (C-12), 147.0 (C-6'), 139.9 (C-6 or C-7 or C-8'), 139.4 (C-6 or C-7 or C-8'), 139.1 (C-6 or C-7 or C-8'), 135.8 (C-9'), 134.7 (C-9), 134.0 (C-8a), 131.8 (C-4a), 131.6 (C-14), 130.4 (C-10'), 130.3 (C-7'), 129.2 (C-4a'), 122.8 (C-13'), 122.5 (C-14), 121.2 (C-11'), 119.1 (C-8a'), 118.3 (C-10), 115.8 (C-5), 114.5 (C-8), 112.5 (C-13), 106.6 (C-5'), 66.0 (C-1), 56.7 (C-6'-OMe), 56.4 (C-12-OMe), 56.1 (C-1'), 51.8 (C-3), 44.9 (C-α'), 44.2 (C-3'), 40.4 (C—N2-Me), 38.9 (C-α), 33.4 (C3"-NH-Me), 28.0 (C-4'), 26.7 (C-4).

HRMS-ESI (m/z) calculated for C$_{37}$H$_{38}$N$_3$O$_5$S [M+H]$^+$: 636.2527; Found: 636.2540.

Example 6: Product 15

To a solution of trilobine (1) (6 mg-10.68 μmol) in 300 μL of THF was added cyanogen bromide (7 μL-15.42 μmol) and N,N-diisopropylethylamine (3 μL-17.64 μmol). The mixture was stirred 24 h at RT in inert argon atmosphere. The reaction mixture was concentrated under reduced pressure and the residue was purified by semi-preparative X-Terra RP-18 HPLC, eluting with a linear gradient H$_2$O/MeCN with 0.02% triethylamine (50:50 to 0:100), to give 15 (0.8 mg, 1.36 μmol, 13%).

(15)

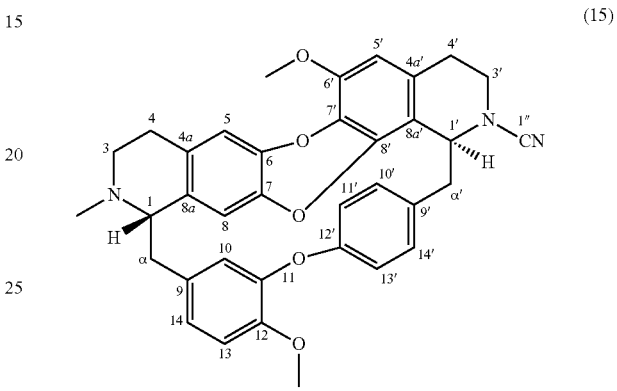

$^1$H NMR (500 MHz, CDCl$_3$) δ 7.73 (1H, dd, J=8.4 Hz, J=1.9 Hz, H-14'), 7.30 (1H, dd, J=8.3 Hz, J=2.6 Hz, H-13'), 7.17 (1H, dd, J=8.2 Hz, J=1.9 Hz, H-10'), 7.03 (1H, dd, J=8.3 Hz, J=2.3 Hz, H-11'), 6.90-6.86 (2H, m, H-13, H-14), 6.64 (1H, s, H-5), 6.56 (1H, d, J=1.5 Hz, H-10), 6.35 (1H, s, H-5'), 6.17 (1H, s, H-8), 4.78 (1H, t, J=3.5 Hz, H-1'), 3.98 (3H, s, 12-OMe), 3.88 (3H, s, 6'-OMe), 3.57 (2H, m, H-3'), 3.48 (1H, dd, J=15.7 Hz, J=2.7 Hz, H-α'), 3.28 (1H, br, H-1), 3.07 (1H, m, H-4'), 3.06-2.92 (2H, m, H-α, H-α'), 2.86 (1H, m, H-3), 2.78-2.70 (3H, m, H-4, H-4', H-α), 2.67-2.61 (2H, m, H-3, H-4), 2.43 (3H, s, N2-Me).

$^{13}$C NMR (125 MHz, CDCl$_3$) δ 154.9 (C-12'), 150.2 (C-11), 147.4 (C-12), 147.2 (C-6'), 139.2 (C-6 or C-7), 139.1 (C-6 or C-7), 137.3 (C-9'), 135.9 (C-8'), 135.4 (C-9), 134.1 (C-8a), 131.3 (C-10'), 130.6 (C-4a and C-7'), 129.3 (C-14'), 126.3 (C-4a'), 123.3 (C-13'), 122.1 (C-11' and C-14), 117.8 (C-1" and C-8a'), 117.4 (C-10), 116.1 (C-5), 114.4 (C-8), 112.4 (C-13), 106.8 (C-5'), 67.7 (C-1), 58.9 (C-1'), 56.6 (C-6'-OMe), 56.4 (C-12-OMe), 50.0 (C-3), 45.1 (C-α'), 42.7 (C-3'), 42.9 (C—N2-Me), 41.2 (C-α), 27.8 (C-4), 27.0 (C-4').

HRMS-ESI (m/z) calculated for C$_{36}$H$_{34}$N$_3$O$_5$ [M+H]$^+$: 588.2500; Found: 588.2493.

Example 7: Product 16

To a solution of trilobine 1 (6 mg-10.68 μmol) in 300 μL of ethanol was added 2 μL acrylonitrile (133.17 μmol) and 3 μL of N-ethyl-N-isopropylpropan-2-amine (11.78 μmol). The mixture was stirred 24 h at RT in inert argon atmosphere. The reaction mixture was concentrated under reduced pressure and the residue was purified by semi-preparative X-Terra RP-18 HPLC, eluting with a linear gradient H$_2$O/MeCN with 1% formic acid (95:5 to 50:50), to give 16 (1. mg, 1.95 μmol, 18%).

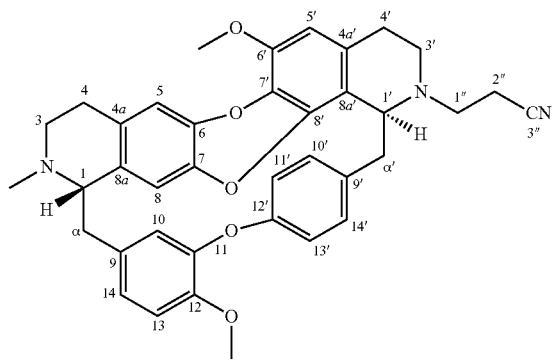

(16)

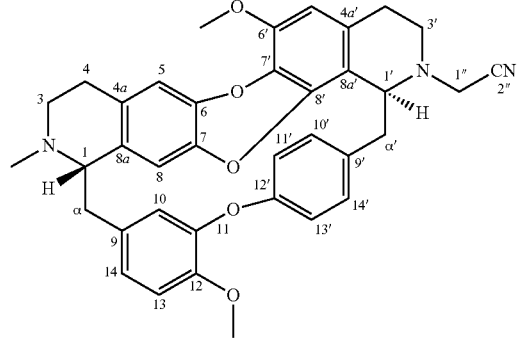

(17)

¹H NMR (500 MHz, MeOD) δ 7.66 (1H, dd, J=8.5 Hz, J=2.1 Hz, H-14'), 7.18 (1H, dd, J=8.3 Hz, J=2.6 Hz, H-13'), 7.14 (1H, dd, J=8.3 Hz, J=2.4 Hz, H-10'), 7.02 (1H, d, J=8.3 Hz, H-13), 6.96 (1H, dd, J=8.3 Hz, J=2.1 Hz, H-14), 6.88 (1H, dd, J=8.3 Hz, J=2.6 Hz, H-11'), 6.67 (1H, s, H-5), 6.65 (1H, d, J=2.0 Hz, H-10), 6.50 (1H, s, H-5'), 6.32 (1H, s, H-8), 4.06 (1H, br, H-1'), 3.93 (3H, s, 12-OMe), 3.83 (3H, s, 6'-OMe), 3.61 (1H, br, H-1), 3.38 (2H, m, H-3', H-α'), 3.11 (1H, m, H-3'), 3.05-2.72 (12H, m, H-1", H-2", H-3, H-4, H-4', H-α, H-α'), 2.57 (1H, m, H-4'), 2.53 (3H, s, N2-Me).

¹³C NMR (125 MHz, MeOD) δ 156.3 (C-12'), 151.6 (C-11), 149.6 (C-12), 148.1 (C-6'), 142.3 (C-6 or C-7), 141.5 (C-6 or C-7), 140.9 (C-9'), 138.2 (C-8'), 134.4 (C-9), 132.7 (C-8a), 132.5 (C-10'), 131.5 (C-4a), 130.8 (C-7'), 130.4 (C-14'), 129.7 (C-4a'), 123.6 (C-13'), 123.5 (C-14), 122.4 (C-11'), 121.0 (C-8a'), 120.7 (C-3"), 118.9 (C-10), 116.9 (C-5), 115.6 (C-8), 114.5 (C-13), 108.9 (C-5'), 67.8 (C-1), 61.3 (C-1'), 57.7 (C-6'-OMe and C-12-OMe), 52.0 (C-3), 50.2 (C-1"), 44.9 (C-α'), 43.6 (C-3'), 41.3 (C—N2-Me), 39.8 (C-α), 27.0 (C-4), 23.6 (C-4'), 18.1 (C-2").

HRMS-ESI (m/z) calculated for $C_{38}H_{38}N_3O_5$ [M+H]⁺: 616.2806; Found: 616.2799.

Example 8: Product 17

To a solution of trilobine 1 (6 mg, 10.68 μmol) in 2 mL of DMF was added 2-bromoacetonitrile (1 μL-14.35 μmol), potassium iodide (0.5 mg-3.01 μmol) and potassium carbonate (2 mg-14.47 μmol). The mixture was stirred 24 h at RT. The reaction mixture was concentrated under reduced pressure and the residue was purified by semi-preparative X-Terra RP-18 HPLC, eluting with a linear gradient H₂O/MeCN with 1% formic acid (80:20 to 0:100), to give 17 (2.3 mg, 3.82 μmol, 36%).

¹H NMR (500 MHz, MeOD) δ 7.68 (1H, dd, J=8.6 Hz, J=2.2 Hz, H-14'), 7.20 (1H, dd, J=8.3 Hz, J=2.5 Hz, H-13'), 7.13 (1H, dd, J=8.3 Hz, J=2.2 Hz, H-10'), 7.01 (1H, d, J=8.2 Hz, H-13), 6.95 (1H, dd, J=8.2 Hz, J=2.2 Hz, H-14), 6.88 (1H, dd, J=8.3 Hz, J=2.6 Hz, H-11'), 6.67 (1H, s, H-5), 6.60 (1H, d, J=2.0 Hz, H-10), 6.51 (1H, s, H-5'), 6.25 (1H, s, H-8), 4.06 (1H, br, H-1'), 3.92 (3H, s, 12-OMe), 3.86 (1H, m, H-1"), 3.84 (3H, s, 6'-OMe), 3.86 (1H, d, J=17.0 Hz, H-1"), 3.62 (1H, br, H-1), 3.35 (2H, m, H-3', H-α'), 3.09 (1H, br m, H-3'), 3.05-2.98 (3H, m, H-3, H-α), 2.94-2.71 (5H, m, H-4, H-4', H-α, H-α'), 2.66 (1H, m, H-4'), 2.52 (3H, s, N2-Me).

¹³C NMR (125 MHz, MeOD) δ 156.3 (C-12'), 151.7 (C-Hz), 149.4 (C-12), 148.2 (C-6'), 142.3 (C-7), 141.3 (C-6), 140.5 (C-8'), 140.3 (C-9'), 134.4 (C-9), 133.2 (C-8a), 132.5 (C-10'), 131.9 (C-4a), 131.0 (C-7'), 130.3 (C-14'), 129.4 (C-4a'), 123.7 (C-11'), 123.6 (C-14), 122.7 (C-13'), 120.0 (C-8a'), 118.8 (C-2" and C-10), 117.0 (C-5), 115.6 (C-8), 114.5 (C-13), 108.7 (C-5'), 67.7 (C-1), 60.3 (C-1'), 56.9 (C-6'-OMe and C-12-OMe), 51.7 (C-3), 45.1 (C-3'), 44.8 (C-α'), 42.6 (C-1"), 41.3 (C—N2-Me), 39.6 (C-α), 27.0 (C-4), 24.5 (C-4').

HRMS-ESI (m/z) calculated for $C_{37}H_{36}N_3O_5$ [M+H]⁺: 602.2649; Found: 602.2647.

Example 9: Product 18

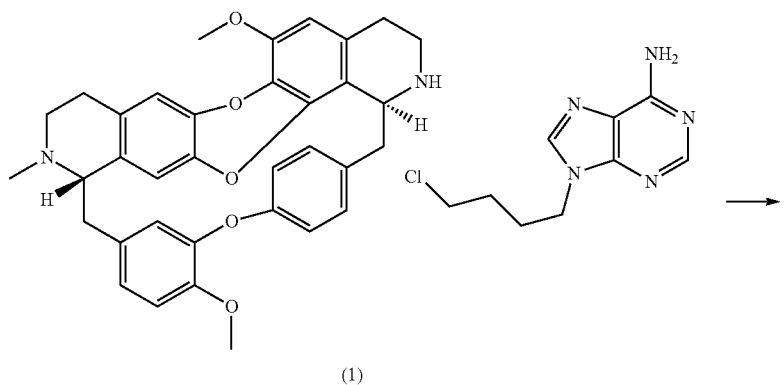

(1)

-continued

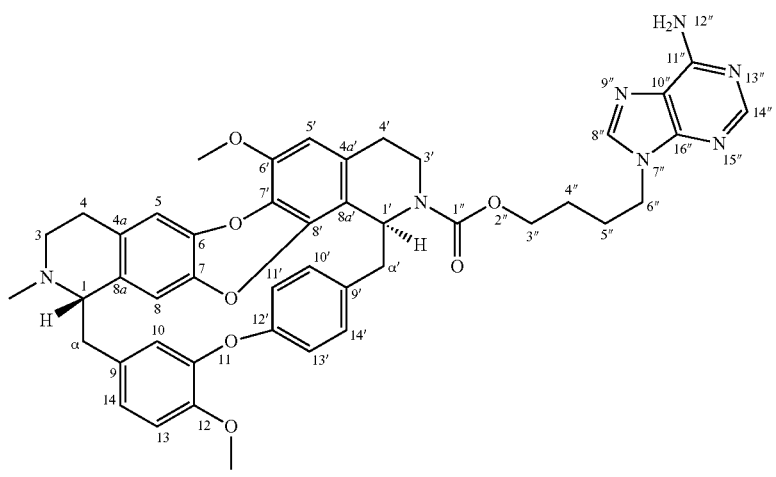

(18)

To a solution of trilobine 1 (6 mg-10.68 μmol) in 2 mL of DMF was added 9-(4-chlorobutyl)-9H-purin-6-amine (3 mg-13.29 μmol), potassium iodide (0.5 mg-3.01 μmol) and potassium carbonate (5 mg-36.18 μmol). The mixture was stirred 24 hours at 70° C. The reaction mixture was concentrated under reduced pressure and the residue was purified by HPLC semi-preparative X-Terra RP-18, eluting with a linear gradient $H_2O$/MeCN with 1% formic acid (80.20 to 0:100), to give 18 as a mixture of two rotamers in proportion 60/40 (1.8 mg, 2.26 μmol, 21%).

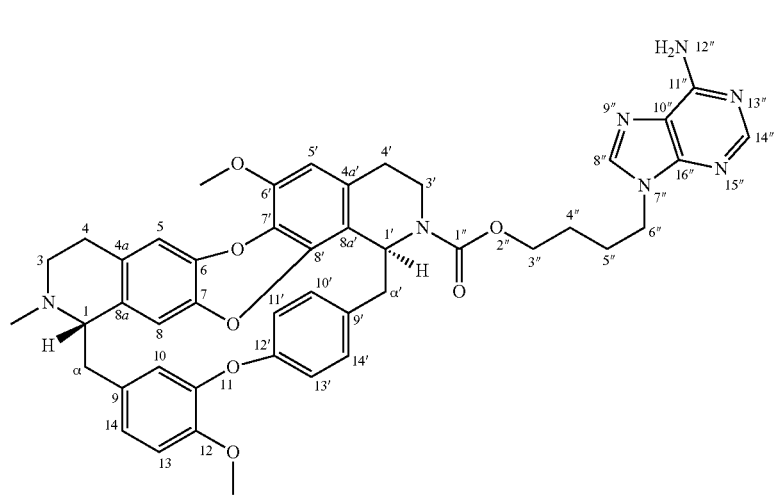

(18)

$^1$H NMR (500 MHz, MeOD) δ 8.19/8.02 (1H, s, H-14″), 8.15/8.00 (1H, s, H-8″), 7.79/7.58 (1H, br d, J=7.7 Hz, H-14′), 7.08 (1H, m, H-13′), 7.03 (1H, d, J=8.2 Hz, H-13), 6.97 (2H, m, H-10′, H-14), 6.81 (1H, br d, J=7.3 Hz, H-11′), 6.74 (1H, s, H-5), 6.66/6.54 (1H, br, H-10), 6.63 (1H, s, H-5′), 6.44/6.21 (1H, s, H-8), (1H, br d, J=7.3 Hz, H-1′), 4.37-4.20 (4H, H-3″, H-6″), 3.91 (3H, s, 12-OMe), 3.87 (3H, s, 6′-OMe), 3.80 (1H, br, H-1), 3.68-3.56 (2H, m, H-3′), 3.33 (1H, m, H-3), 3.18 (1H, m, H-α′), 3.02-2.80 (8H, H-3, H-4, H-4′, H-α, H-α′), 2.52 (3H, s, N2-Me), 2.04 (2H, m, H-5″), 1.73 (2H, m, H-4″).

$^{13}$C NMR (125 MHz, MeOD) δ 157.5 (C-1″ or C-11″), 157.3 (C-1″ or C-11″), 156.7/156.5 (C-12′), 153.7/153.8 (C-14″), 151.3/150.8 (C-11), 150.8/150.7 (C-16″), 149.8/149.7 (C-12), 148.4/148.5 (C-6′), 142.9/142.6 (C-8″), 142.4 (C-6 or C-7), 141.1 (C-6 or C-7), 139.6 (C-8′), 138.5/138.3 (C-9′), 133.2 (C-9), 132.5 (C-4a), 132.3/131.5 (C-14′), 132.0/131.8 (C-10′), 131.7 (C-4a′), 130.8 (C-7′ and C-8a), 124.1/124.0 (C-14), 123.6/123.4 (C-13′), 122.3/122.2 (C-11′), 120.3 (C-10″), 119.9 (C-8a′), 119.0/118.9 (C-10), 117.0/117.1 (C-5), 115.9/115.4 (C-8), 114.6/114.5 (C-13), 108.9/108.7 (C-5′), 66.4 (C-1), 67.0/66.2 (C-3″), 57.0 (C-6′-OMe and C-12-OMe), 53.8/53.9 (C-1′), 52.6/52.1 (C-3), 46.9/46.7 (C-α′), 44.8/44.9 (C-6″), 42.0/42.1 (C-3′), 40.0 (C—N2-Me), 37.5 (C-α), 29.1 (C-4′), 27.8 (C-5″), 27.5 (C-4″), 26.4 (C-4).

HRMS-ESI (m/z) calculated for $C_{45}H_{46}N_7O_7$ [M+H]$^+$: 796.3453; Found: 796.3442.

Example 10: Product 19

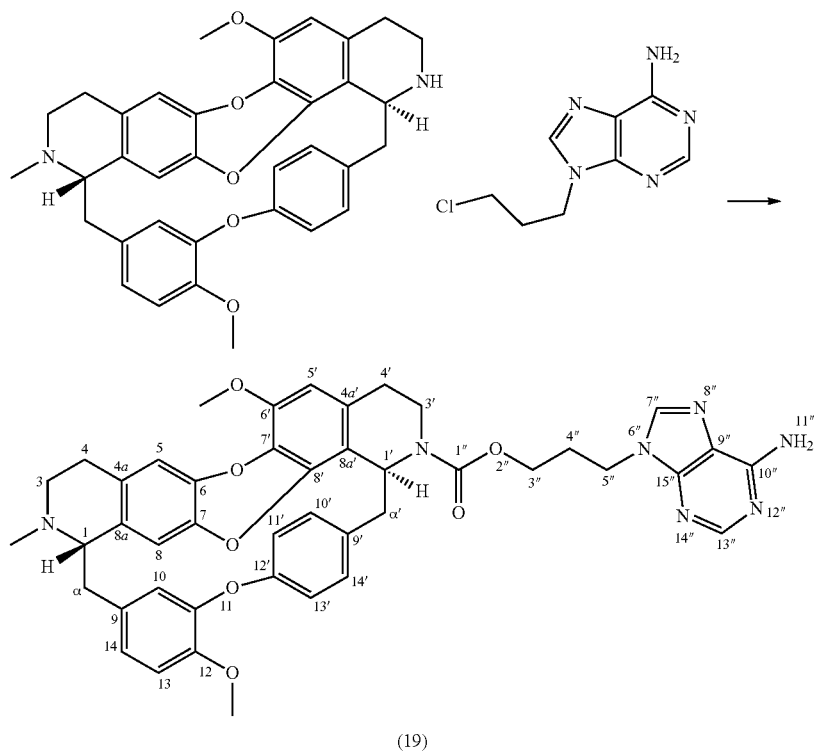

(19)

To a solution of trilobine 1 (6 mg-10.68 μmol) in 2 mL of DMF was added 9-(3-chloropropyl)-9H-purin-6-amine (3 mg-14.17 μmol), potassium iodide (0.5 mg-3.01 μmol) and potassium carbonate (5 mg-36.18 μmol). The mixture was stirred 24 hours at 70° C. The reaction mixture was concentrated under reduced pressure and the residue was purified by HPLC semi-preparative X-Terra RP-18, eluting with a linear gradient H$_2$O/MeCN with 1% formic acid (80.20 to 0:100), to give 19 as a mixture of two rotamers in proportion 80/20 (1.8 mg, 2.30 μmol, 22%).

$^1$H NMR (500 MHz, MeOD) δ 8.19/8.07 (1H, s, H-7″), 8.14/7.98 (1H, s, H-13″), 7.79/7.64 (1H, br d, J=8.3 Hz, H-14'), 7.09 (1H, dd, J=8.1 Hz, J=2.3 Hz, H-13'), 7.02 (1H, d, J=8.3 Hz, H-13), 6.98 (2H, m, H-10', H-14), 6.83 (1H, dd, J=8.2 Hz, J=2.1 Hz, H-11'), 6.72 (1H, s, H-5), 6.65 (1H, br, H-10), 6.62 (1H, s, H-5'), 6.42/6.35 (1H, s, H-8), 5.34 (1H, br d, J=7.3 Hz, H-1'), 4.44-4.36 (2H, m, H-5″), 4.32-4.17 (2H, m, H-3″), 3.91 (3H, s, 12-OMe), 3.87 (3H, s, 6'-OMe), 3.74 (1H, br, H-1), 3.66 (1H, m, H-3'), 3.45 (1H, m, H-3'), 3.17-2.77 (10H, H-3, H-4, H-4', H-α, H-α'), 2.50/2.45 (3H, s, N2-Me), 2.35 (2H, m, H-4″).

$^{13}$C NMR (125 MHz, MeOD) δ 157.4 (C-1″ or C-10″), 156.9 (C-1″ or C-10″), 156.5 (C-12'), 153.9 (C-13″), 151.4 (C-11), 151.1 (C-15″), 149.7 (C-12), 148.4 (C-6'), 143.0 (C-7″), 142.5 (C-6 or C-7), 141.1 (C-6 or C-7), 139.6 (C-8'), 138.5 (C-9'), 133.5 (C-9), 132.5 (C-4a), 132.3 (C-14'), 131.9 (C-10'), 131.6 (C-4a'), 130.8 (C-7' and C-8a), 124.0 (C-14), 123.6 (C-13'), 122.2 (C-11'), 120.2 (C-9″), 119.1 (C-10), 119.0 (C-8a'), 117.0 (C-5), 115.7/115.9 (C-8), 114.5/114.6 (C-13), 108.8/108.6 (C-5'), 66.7 (C-1), 64.7/64.4 (C-3"), 57.0 (C-6'-OMe and C-12-OMe), 53.7 (C-1'), 52.6 (C-3), 47.0 (C-α'), 42.9 (C-5"), 41.8 (C-3'), 40.2 (C—N2-Me), 37.5 (C-α), 30.6/30.4 (C-4"), 29.1/28.7 (C-4'), 26.5 (C-4).

HRMS-ESI (m/z) calculated for $C_{44}H_{44}N_7O_7$ [M+H]$^+$: 782.3297; Found: 782.3296.

Examples 11 and 12: Products 20 and 21

To a solution of O-methylcocsoline 3 (6 mg-10.68 μmol) in 2 mL of DMF was added 2-bromoacetonitrile (3 mg-25.01 μmol), potassium iodide (0.5 mg-3.01 μmol) and potassium carbonate (5 mg-36.18 μmol). The mixture was stirred 24 hours at RT. The reaction mixture was concentrated under reduced pressure and the residue was purified by HPLC semi-preparative X-Terra RP-18, eluting with a linear gradient H$_2$O/MeCN with 0.02% triethylamine (95:5 to 0:100), to give 20 (0.2 mg, 0.33 μmol, 3.1%) and 21 (1.4 mg, 2.08 μmol, 19%).

(20)

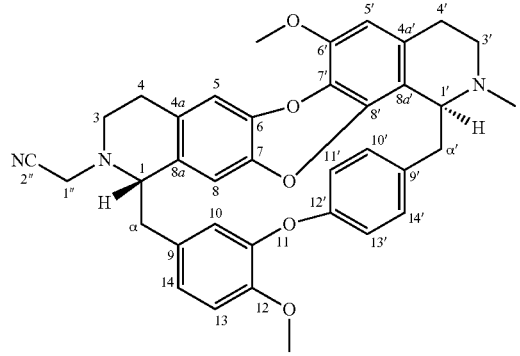

$^1$H NMR (500 MHz, MeOD) δ 7.66 (1H, dd, J=8.2 Hz, J=2.4 Hz, H-14'), 7.22 (1H, dd, J=8.0 Hz, J=2.2 Hz, H-10'), 7.17 (1H, dd, J=8.5 Hz, J=2.6 Hz, H-13'), 7.02-7.05 (2H, m, H-11', H-13), 6.96 (1H, dd, J=8.3 Hz, J=2.2 Hz, H-14), 6.62 (1H, s, H-5), 6.58 (1H, d, J=2.1 Hz, H-10), 6.53 (1H, s, H-5'), 6.16 (1H, s, H-8), 4.13 (1H, br t, J=3.3 Hz, H-1'), 4.00 (1H, d, J=17.4 Hz, H-1"), 3.97 (3H, s, 12-OMe), 3.87 (3H, s, 6'-OMe), 3.78 (1H, d, J=17.4 Hz, H-1"), 3.46 (1H, br t, H-1), 3.41-3.19 (2H, m, H-3'), 3.00-2.61 (10H, m, H-3, H-4, H-4', H-α, H-α'), 2.58 (3H, s, N2'-Me).

$^{13}$C NMR (125 MHz, MeOD) δ 155.7 (C-12'), 152.0 (C-11), 149.0 (C-12), 148.1 (C-6'), 141.4 (C-6 or C-7 or C-8' or C-9'), 141.2 (C-6 or C-7 or C-8' or C-9'), 141.0 (C-6 or C-7 or C-8' or C-9'), 140.5 (C-6 or C-7 or C-8' or C-9'), 135.6 (C-8a), 135.4 (C-9), 132.6 (C-10'), 131.6 (C-4a), 131.1 (C-7'), 129.9 (C-14'), 128.8 (C-4a'), 123.8 (C-13'), 123.2 (C-11'), 122.8 (C-14), 121.1 (C-8a'), 118.0 (C-10), 116.8 (C-5), 116.7 (C-2"), 115.3 (C-8), 114.2 (C-13), 108.5 (C-5'), 66.2 (C-1), 61.4 (C-1'), 56.9 (C-6'-OMe and C-12-OMe), 50.3 (C-3), 46.0 (C-3'), 43.5 (C-α), 43.2 (C-α'), 42.5 (C-1"), 42.0 (C—N2'-Me), 28.9 (C-4), 24.6 (C-4').

HRMS-ESI (m/z) calculated for $C_{37}H_{36}N_3O_5$ [M+H]$^+$: 602.2649; Found: 602.2647.

(21)

$^1$H NMR (500 MHz, MeOD) δ 7.75 (1H, dd, J=8.5 Hz, J=2.2 Hz, H-14'), 7.21 (1H, dd, J=8.2 Hz, J=2.4 Hz, H-10'), 7.17 (1H, dd, J=8.4 Hz, J=2.7 Hz, H-13'), 7.00-6.98 (2H, m, H-11', H-13), 6.92 (1H, dd, J=8.2 Hz, J=2.2 Hz, H-14), 6.57 (1H, s, H-5), 6.54 (1H, d, J=2.2 Hz, H-10), 6.47 (1H, s, H-5'), 6.12 (1H, s, H-8), 4.24 (1H, br, J=3.3 Hz, H-1'), 3.98 (1H, d, J=17.5 Hz, H-1"), 3.94 (3H, s, 12-OMe), 3.88 (1H, m, H-1'"), 3.84 (3H, s, 6'-OMe), 3.76 (2H, m, H-1" and H-1'"), 3.44 (1H, br, H-1), 3.18-2.56 (12H, m, H-3, H-3', H-4, H-4', H-α, H-α').

$^{13}$C NMR (125 MHz, MeOD) δ 155.7 (C-12'), 152.0 (C-11), 149.0 (C-12), 148.2 (C-6'), 141.3 (C-6 or C-7 or C-8' or C-9'), 141.0 (C-6 or C-7 or C-8' or C-9'), 140.7 (C-6 or C-7 or C-8' or C-9'), 135.8 (C-8a), 135.5 (C-9), 132.5 (C-10'), 131.5 (C-4a), 131.1 (C-7'), 129.7 (C-14'), 129.0 (C-4a'), 123.8 (C-13'), 123.2 (C-11'), 122.8 (C-14), 119.9 (C-8a'), 119.0 (C-2'"), 118.1 (C-10), 116.8 (C-5), 116.7 (C-2"), 115.3 (C-8), 114.3 (C-13), 108.4 (C-5'), 66.3 (C-1), 60.3 (C-1'), 56.9 (C-6'-OMe and C-12-OMe), 49.6 (C-3), 45.2 (C-1'" or C-3'), 44.9 (C-1'" or C-3'), 43.6 (C-α or C-α'), 43.5 (C-α or C-α'), 42.5 (C-1"), 28.9 (C-4), 24.0 (C-4').

HRMS-ESI (m/z) calculated for $C_{38}H_{34}N_4NaO_5$ [M+Na]$^+$: 649.2421; Found: 649.2415.

Example 13: Product 22

To a solution of O-methylcocsoline 3 (6 mg-10.68 μmol) in 2 mL of ethanol was added acrylonitrile (3 mg-56.60 μmol) and N-ethyl-N-isopropylpropan-2-amine (0.5 mg-3.87 μmol). The mixture was stirred 24 hours in inert argon atmosphere at RT. The reaction mixture was concentrated under reduced pressure and the residue was purified by HPLC semi-preparative X-Terra RP-18, eluting with a linear gradient H$_2$O/MeCN with 0.1% formic acid (95:5 to 0:100), to give 22 (2.2 mg, 3.58 μmol, 33%).

(22)

¹H NMR (500 MHz, MeOD) δ 7.65 (1H, dd, J=8.5 Hz, J=2.1 Hz, H-14'), 7.20 (2H, m, H-10', H-13'), 6.98 (2H, m, H-11', H-13), 6.90 (1H, dd, J=8.1 Hz, J=2.0 Hz, H-14), 6.58 (1H, s, H-5), 6.56 (1H, d, J=2.0 Hz, H-10), 6.54 (1H, s, H-5'), 6.08 (1H, s, H-8), 4.29 (1H, br, H-1'), 3.93 (3H, s, 12-OMe), 3.84 (3H, s, 6'-OMe), 3.46 (1H, br t, J=3.4 Hz, H-1), 3.42-3.34 (2H, m, H-3', H-α'), 3.14 (1H, m, H-3'), 3.05 (1H, m, H-4'), 2.97-2.92 (2H, m, H-3, H-α), 2.87-2.81 (2H, m, H-3, H-α'), 2.75-2.70 (5H, m, H-3, H-4', H-1", H-α), 2.74 (3H, s, N2'-Me), 2.67-2.57 (2H, m, H-4), 2.48 (2H, m, H-2").

¹³C NMR (125 MHz, MeOD) δ 156.3 (C-12'), 151.8 (C-11), 149.0 (C-12), 148.6 (C-6'), 141.3 (C-8'), 140.8 (C-6 or C-7), 140.6 (C-6 or C-7), 139.4 (C-9'), 136.6 (C-9), 136.3 (C-8a), 132.8 (C-10'), 132.2 (C-4a), 131.4 (C-7'), 129.9 (C-14'), 127.8 (C-4a'), 123.9 (C-13'), 123.1 (C-11' or C-14), 123.0 (C-11' or C-14), 120.6 (C-3"), 118.6 (C-8a'), 118.4 (C-10), 116.9 (C-5), 115.3 (C-8), 114.3 (C-13), 108.4 (C-5'), 66.4 (C-1), 61.9 (C-1'), 57.0 (C-6'-OMe and C-12-OMe), 49.4 (C-1"), 47.0 (C-3), 46.3 (C-3'), 42.7 (C-α), 42.2 (C-α'), 41.4 (C—N2'-Me), 27.3 (C-4), 24.0 (C-4'), 17.4 (C-2").

HRMS-ESI (m/z) calculated for $C_{38}H_{38}N_3O_5$ [M+H]⁺: 616.2806; Found: 616.2807.

Example 14: Product 24

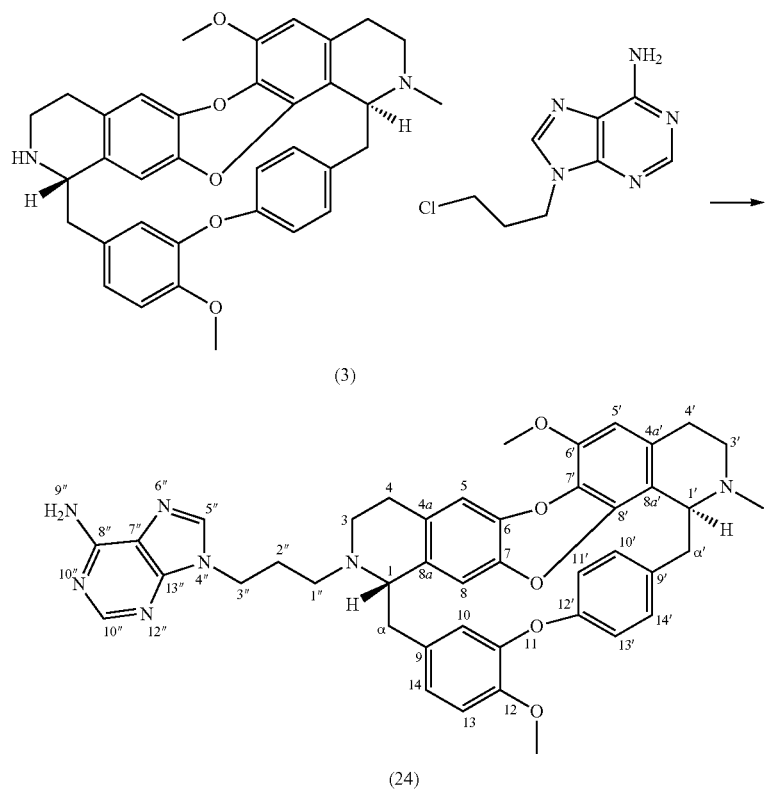

To a solution of O-methylcocsoline 3 (3 mg-5.34 μmol) in 200 μL of DMF was added 9-(3-chloropropyl)-9H-purin-6-amine (13 mg-61.42 μmol), potassium iodide (0.5 mg-3.01 μmol) and potassium carbonate (8.5 mg-36.18 μmol). The mixture was stirred 24 hours at 70° C. The reaction mixture was concentrated under reduced pressure and the residue was purified by HPLC semi-preparative X-Terra RP-18, eluting with a linear gradient H₂O/MeCN with 1% formic acid (95.5 to 50:50), to give 24 (1.2 mg, 1.63 μmol, 30%).

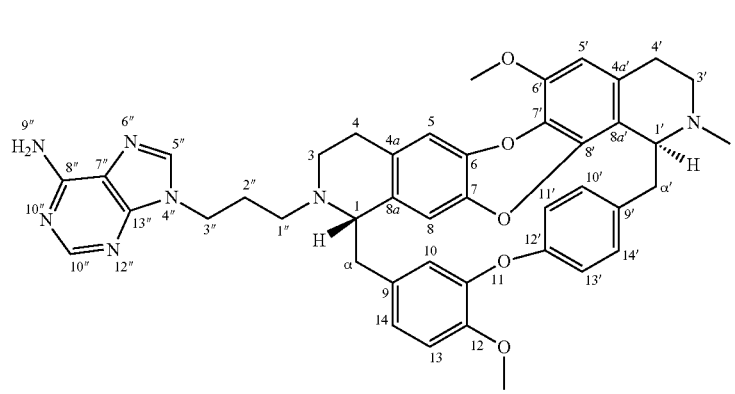

(24)

$^1$H NMR (500 MHz, MeOD) δ 8.19 (1H, s, H-11″), 8.05 (1H, s, H-5″), 7.66 (1H, dd, J=8.5 Hz, J=2.1 Hz, H-14′), 7.25 (1H, dd, J=8.4 Hz, J=2.3 Hz, H-10′), 7.18 (1H, dd, J=8.5 Hz, J=2.6 Hz, H-13′), 7.00 (1H, dd, J=8.2 Hz, J=2.5 Hz, H-11′), 6.80 (1H, d, J=8.3 Hz, H-13), 6.56-6.52 (3H, m, H-5, H-5′, H-14), 6.49 (1H, d, J=2.1 Hz, H-10), 6.00 (1H, s, H-8), 4.24-4.28 (3H, m, H-1′, H-3″), 3.95 (3H, s, 12-OMe), 3.88 (3H, s, 6′-OMe), 3.44 (1H, br d, J=16.4 Hz, H-α′), 3.38-3.34 (2H, m, H-1, H-3′), 3.09 (1H, m, H-3′), 2.96-2.75 (6H, m, H-3, H-4′, H-α, H-α′), 2.74 (3H, s, N2′-Me), 2.67-2.58 (4H, m, H-1″, H-4, H-α), 2.49 (1H, m, H-1″), 2.02 (2H, m, H-2″).

$^{13}$C NMR (125 MHz, MeOD) δ 157.4 (C-8″), 156.0 (C-12′), 153.8 (C-11″), 151.8 (C-11), 150.9 (C-13″), 148.8 (C-12), 148.6 (C-6′), 143.0 (C-5″), 141.3 (C-6 or C-7 or C-8′), 140.8 (C-6 or C-7 or C-8′), 140.7 (C-6 or C-7 or C-8′), 139.8 (C-9′), 136.4 (C-8a and C-9), 132.8 (C-10′), 131.9 (C-4a), 131.3 (C-7′), 129.8 (C-14′), 128.0 (C-4a′), 123.9 (C-13′), 123.1 (C-11′), 122.9 (C-14), 120.2 (C-7″), 119.0 (C-8a′), 118.1 (C-10), 116.8 (C-5), 115.2 (C-8), 113.9 (C-13), 108.3 (C-5′), 66.6 (C-1), 61.8 (C-1′), 57.0 (C-6′-OMe or C-12-OMe), 56.9 (C-6′-OMe or C-12-OMe), 51.3 (C-1″), 46.8 (C-3), 46.4 (C-3′), 43.2 (C-3″), 42.2 (C-α′), 41.5 (C—N2′-Me), 41.3 (C-α), 28.2 (C-2″), 27.9 (C-4), 24.2 (C-4′).

HRMS-ESI (m/z) calculated for $C_{43}H_{44}N_7O_5$ [M+H]$^+$: 738.3398; Found: 738.3383.

Example 15: Product 25

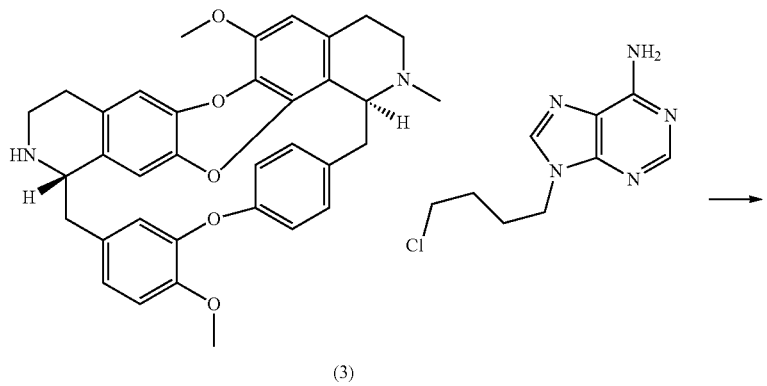

(3)

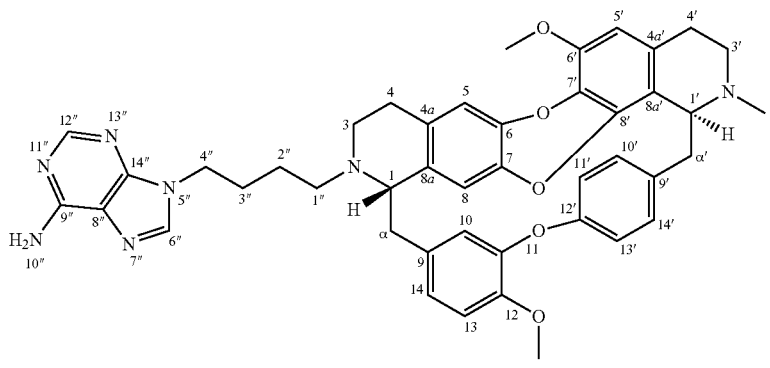

(25)

To a solution of O-methylcocsoline 3 (3 mg-5.34 μmol) in 200 μL of DMF was added 9-(4-chlorobutyl)-9H-purin-6-amine (14 mg-62.04 μmol), potassium iodide (0.5 mg-3.01 μmol) and potassium carbonate (8.5 mg-36.18 μmol). The mixture was stirred 24 hours at 70° C. The reaction mixture was concentrated under reduced pressure and the residue was purified by HPLC semi-preparative X-Terra RP-18, eluting with a linear gradient H₂O/MeCN with 1% formic acid (95.5 to 50:50), to give 25 (2.1 mg, 2.80 μmol, 52%).

$^1$H NMR (500 MHz, MeOD) δ 8.18 (1H, s, H-12″), 8.08 (1H, s, H-6″), 7.63 (1H, dd, J=8.2 Hz, J=2.4 Hz, H-14′), 7.19 (2H, m, H-10′, H-13′), 6.96 (1H, d, J=8.4 Hz, H-13), 6.90 (2H, m, H-11′, H-14), 6.65 (1H, s, H-5), 6.57 (2H, m, H-5′, H-10), 6.17 (1H, s, H-8), 4.28 (1H, br d, J=4.1 Hz, H-1′), 4.21 (2H, t, J=7.0 Hz, H-4″), 3.92 (3H, s, 12-OMe), 3.85 (3H, s, 6′-OMe), 3.66 (1H, br, H-1), 3.40 (2H, m, H-3′, H-α′), 3.12 (1H, m, H-3′), 3.09-2.95 (3H, m, H-3, H-α), 2.87-2.79 (4H, m, H-4′, H-α, H-α′), 2.73 (3H, s, N2′-Me), 2.69 (2H, m, H-4), 2.59 (2H, m, H-1″), 1.87 (2H, m, H-3″), 1.48 (2H, m, H-2″).

$^{13}$C NMR (125 MHz, MeOD) δ 157.4 (C-9″), 156.4 (C-12′), 153.8 (C-12″), 151.6 (C-11), 150.9 (C-14″), 149.3 (C-12), 148.7 (C-6′), 142.8 (C-6″), 141.9 (C-6 or C-7 or C-8′), 140.9 (C-6 or C-7 or C-8′), 140.5 (C-6 or C-7 or C-8′), 139.0 (C-9′), 134.9 (C-9), 133.8 (C8a), 132.7 (C-10′), 132.2 (C-4a), 131.2 (C-7′), 130.3 (C-14′), 128.1 (C-4a′), 123.9 (C-13′), 123.5 (C-14), 122.8 (C-11′), 120.1 (C-8″), 118.6 (C-8a′ and C-10), 117.0 (C-5), 115.4 (C-8), 114.3 (C-13),

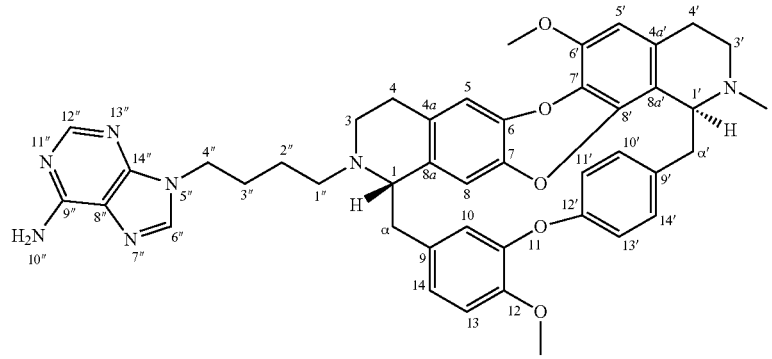

(25)

108.7 (C-5′), 66.0 (C-1), 61.7 (C-1′), 56.9 (C-6′-OMe and C-12-OMe), 52.6 (C-1″), 47.7 (C-3), 46.2 (C-3′), 44.6 (C-4″), 41.8 (C-α′), 41.5 (C—N2′-Me), 39.8 (C-α), 28.9 (C-3″), 26.6 (C-4), 24.5 (C-2″), 24.2 (C-4′).

HRMS-ESI (m/z) calculated for $C_{44}H_{46}N_7O_5$ [M+H]$^+$: 752.3555; Found: 752.3544.

Example 16: Product 27

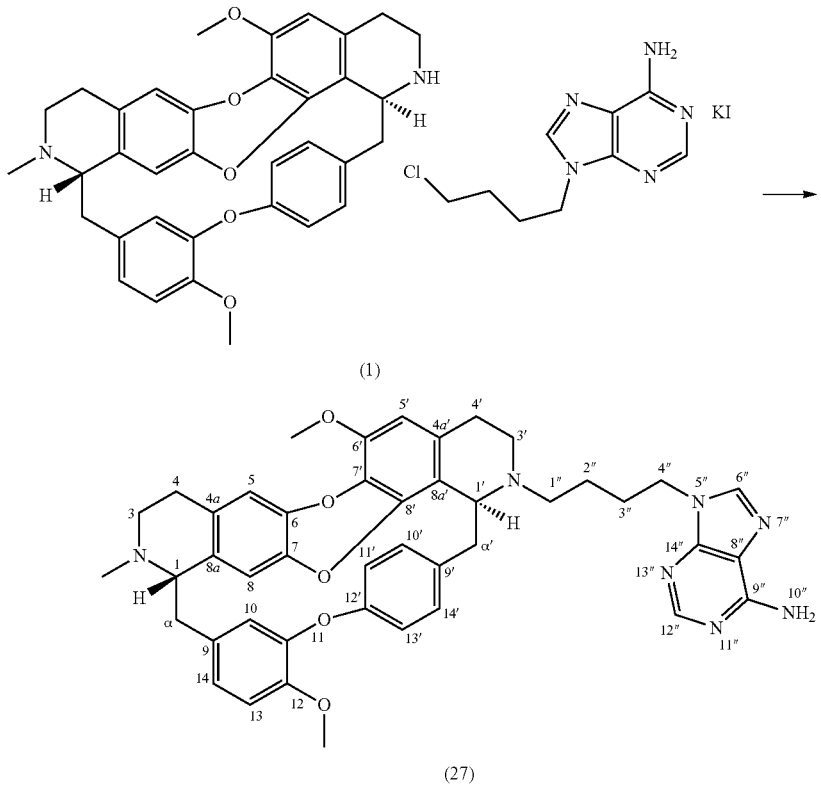

To a solution of trilobine 1 (3 mg-5.34 µmol) in 200 µL of MeCN was added 9-(4-chlorobutyl)-9H-purin-6-amine (10 mg-44.31 µmol), potassium iodide (0.5 mg-3.01 µmol) and potassium carbonate (8.5 mg-36.18 µmol). The mixture was stirred 24 hours at 70° C. The reaction mixture was concentrated under reduced pressure and the residue was purified by HPLC semi-preparative X-Terra RP-18, eluting with a linear gradient H₂O/MeCN with 1% formic acid (95.5 to 50:50), to give 27 (1.1 mg, 1.46 µmol, 27%).

(27)

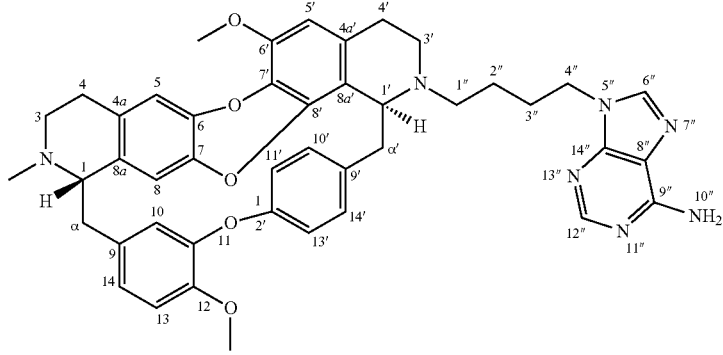

$^1$H NMR (500 MHz, MeOD) δ 8.16 (1H, s, H-12″), 8.13 (1H, s, H-6″), 7.42 (1H, dd, J=8.3 Hz, J=2.1 Hz, H-14′), 7.12 (1H, dd, J=8.3 Hz, J=2.7 Hz, H-13′), 7.09 (1H, dd, J=8.3 Hz, J=2.2 Hz, H-10′), 7.04 (1H, d, J=8.4 Hz, H-13), 6.99 (1H, dd, J=8.2 Hz, J=2.1 Hz, H-14), 6.85 (1H, dd, J=8.3 Hz, J=2.7 Hz, H-11′), 6.71 (1H, s, H-5), 6.64 (1H, d, J=1.9 Hz, H-10), 6.52 (1H, s, H-5′), 6.33 (1H, s, H-8), 4.30 (2H, t, J=6.8 Hz, H-4″), 4.12 (1H, d, J=5.9 Hz, H-1′), 3.93 (3H, s, 12-OMe), 3.85 (3H, s, 6′-OMe), 3.72 (1H, br, H-1), 3.31-3.27 (2H, m, H-3′, H-α′), 3.21 (1H, m, H-3), 3.12-2.99 (3H, m, H-3, H-α, H-α′), 2.94-2.86 (2H, m, H-4, H-4′), 2.82-2.65 (5H, m, H-1″, H-3, H-4, H-4′), 2.54 (3H, s, N2-Me), 2.00 (2H, m, H-3″), 1.70 (2H, br, H-2″).

$^{13}$C NMR (125 MHz, MeOD) δ 157.5 (C-9″), 156.4 (C-12′), 153.8 (C-12″), 151.5 (C-11), 150.9 (C-14″), 149.6 (C-12), 148.3 (C-6′), 142.9 (C-6″), 142.4 (C-6 or C-7 or C-8′), 141.2 (C-6 or C-7 or C-8′), 140.3 (C-6 or C-7 or C-8′), 139.6 (C-9′), 133.8 (C-9), 132.5 (C-10′), 131.9 (C-4a), 131.4 (C-8a), 130.7 (C-7′), 130.5 (C-14′), 129.3 (C-4a′), 123.9 (C-14), 123.7 (C-13′), 122.6 (C-11′), 120.1 (C-8″), 119.8 (C-8a′), 119.1 (C-10), 117.0 (C-5), 115.6 (C-8), 114.6 (C-13), 109.0 (C-5′), 67.2 (C-1), 59.8 (C-1′), 57.0 (C-6′-OMe and C-12-OMe), 53.6 (C-1″), 52.4 (C-3), 44.7 (C-4″), 44.1 (C-α′), 43.0 (C-3′), 40.6 (C—N2-Me), 38.6 (C-α), 29.1 (C-3″), 26.7 (C-4), 25.5 (C-2″), 23.9 (C-4′).

HRMS-ESI (m/z) calculated for $C_{44}H_{46}N_7O_5$ [M+H]⁺: 752.3555; Found: 752.3541.

Example 17: Product 28

(1)

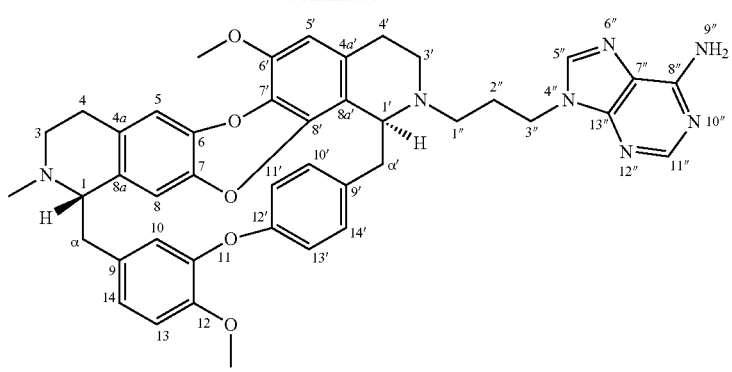

(28)

To a solution of trilobine 1 (3 mg-5.34 µmol) in 200 µL of DMF was added 9-(3-chloropropyl)-9H-purin-6-amine (10 mg-47.25 µmol), potassium iodide (0.5 mg-3.01 µmol) and triethylamine (10 µL-74.10 µmol). The mixture was stirred 24 hours at 70° C. The reaction mixture was concentrated under reduced pressure and the residue was purified by HPLC semi-preparative X-Terra RP-18, eluting with a linear gradient H₂O/MeCN with 1% formic acid (95.5 to 50:50), to give 28 (1.7 mg, 2.31 µmol, 43%).

HRMS-ESI (m/z) calculated for $C_{43}H_{44}N_7O_5$ [M+H]⁺: 738.3398; Found: 738.3387.

Example 19: Product 30

To a solution of trilobine 1 (3 mg-5.34 µmol) in 250 µL of DMF was added 2,5-dimethylenepyrrolidin-1-yl-4-((2,5-dioxo-2,5-dihydro-1H-pyrrol-1-yl)methyl)cyclohexanecarboxylate (6 mg-18.16 µmol) and triethylamine (10 µL-74.10

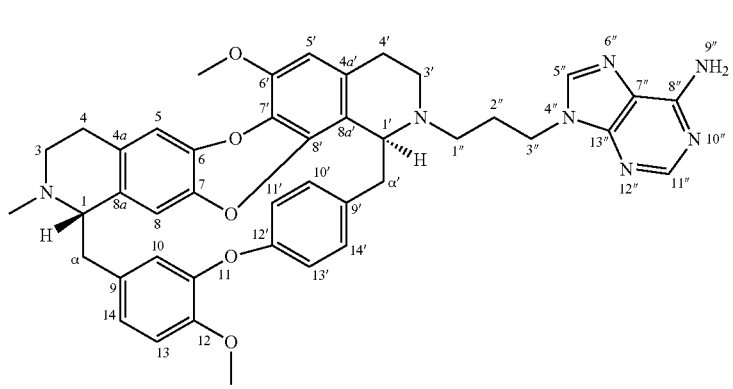

(28)

$^1$H NMR (500 MHz, MeOD) δ 8.11 (1H, s, H-5″), 8.09 (1H, s, H-11″), 7.38 (1H, dd, J=8.3 Hz, J=2.1 Hz, H-14′), 7.10 (1H, dd, J=8.3 Hz, J=2.7 Hz, H-13′), 7.06 (1H, dd, J=8.3, J=2.1 Hz, H-10′), 7.03 (1H, d, J=8.7 Hz, H-13), 6.99 (1H, dd, J=8.3 Hz, J=2.0 Hz, H-14), 6.81 (1H, dd, J=8.2 Hz, J=2.5 Hz, H-11′), 6.71 (1H, s, H-5), 6.64 (1H, d, J=2.1 Hz, H-10), 6.46 (1H, s, H-5′), 6.30 (1H, s, H-8), 4.37 (2H, m, H-3″), 3.94 (1H, br, H-1′), 3.92 (3H, s, 12-O<u>Me</u>), 3.83 (3H, s, 6′-O<u>Me</u>), 3.77 (1H, br, H-1), 3.28-2.95 (7H, m, H-3, H-3′, H-α, H-α′), 2.94-2.60 (7H, m, H-1″, H-3′, H-4, H-4′), 2.57 (3H, s, N2-<u>Me</u>), 2.22 (2H, m, H-2″).

$^{13}$C NMR (125 MHz, MeOD) δ 157.4 (C-8″), 156.3 (C-12′), 153.8 (C-11″), 151.5 (C-11), 150.9 (C-13″), 149.6 (C-12), 148.0 (C-6′), 142.6 (C-5″), 142.6 (C-6 or C-7 or C-8′), 141.4 (C-6 or C-7 or C-8′), 140.0 (C-6 or C-7 or C-8′ and C-9′), 133.5 (C-9), 132.5 (C-10′), 131.7 (C-4a), 130.6 (C-8a and C-14′), 130.4 (C-7′), 129.7 (C-4a′), 123.9 (C-14), 123.6 (C-13′), 122.4 (C-11′), 120.9 (C-8a′), 120.2 (C-7″), 119.2 (C-10), 117.0 (C-5), 115.7 (C-8), 114.6 (C-13), 108.9 (C-5′), 67.0 (C-1), 59.7 (C-1′), 57.0 (C-6′-O<u>Me</u> or C-12-O<u>Me</u>), 56.9 (C-6′-OMe or C-12-OMe), 52.5 (C-3), 51.7 (C-1″), 43.8 (C-3′), 43.5 (C-3″), 42.5 (C-α′), 40.6 (C—N2-<u>Me</u>), 38.1 (C-α), 28.4 (C-2″), 26.5 (C-4), 24.8 (C-4′).

µmol). The reaction mixture was stirred 18 hours at RT. The reaction mixture was concentrated under reduced pressure and the residue was purified by HPLC semi-preparative X-Terra RP-18, eluting with a linear gradient H₂O/MeCN with 1% formic acid (95.5 to 50:50), to give 30 (2.1 mg, 2.69 µmol, 50%).

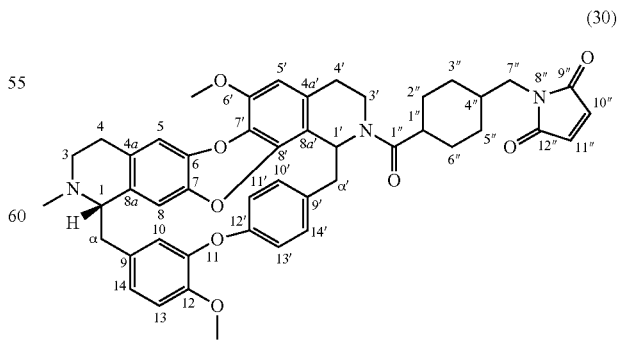

(30)

$^1$H NMR (500 MHz, MeOD) δ 7.87 (1H, dd, J=8.6 Hz, J=2.0 Hz, H-14′), 7.07 (1H, dd, J=8.6 Hz, J=2.5 Hz, H-13′), 7.00 (1H, d, J=8.1 Hz, H-13), 6.97 (2H, m, H-10', H-14), 6.82 (1H, m, H-11'), 6.80 (2H, s, H-11", H-12"), 6.71 (1H, s, H-5), 6.65 (1H, d, J=2.2 Hz, H-10), 6.64 (1H, s, H-5'), 6.38 (1H, s, H-8), 5.79 (1H, br d, J=7.2 Hz, H-1'), 3.91 (3H, s, 12-OMe), 3.87 (3H, s, 6'-OMe), 3.87-3.73 (2H, m, H-3'), 3.69 (1H, br, H-1), 3.38 (2H, m, H-8"), 3.14 (1H, d, J=13.7 Hz, H-α'), 3.10-2.85 (7H, m, H-3, H-4', H-α, H-α'), 2.82-2.77 (2H, m, H-4), 2.67 (1H, m, H-2"), 2.48 (3H, s, N2-Me), 1.98-1.93 (2H, m, H-3" or H-4", or H-6" or H-7"), 1.82-1.71 (3H, m, H-3" or H-4", or H-6" or H-7" and H-5"), 1.59-1.50 (2H, m, (2H, m, H-3" or H-4", or H-6" or H-7"), 1.19-1.05 (2H, m, H-3" or H-4", or H-6" or H-7").

$^{13}$C NMR (125 MHz, MeOD) δ 177.1 (C-1"), 173.0 (C-10" and C-13"), 156.5 (C-12'), 151.4 (C-11), 149.6 (C-12), 148.4 (C-6'), 142.4 (C-6 or C-7 or C-8'), 141.1 (C-6 or C-7 or C-8'), 140.0 (C-6 or C-7 or C-8'), 138.5 (C-9'), 135.5 (C-11" and C-12"), 133.8 (C-9), 132.4 (C-4a and C-10'), 131.8 (C-14'), 131.5 (C-4a' and C-8a), 131.0 (C-7'), 123.9 (C-14), 123.6 (C-13'), 122.1 (C-11'), 120.0 (C-8a'), 119.0 (C-10), 116.9 (C-5), 115.8 (C-8), 114.5 (C-13), 108.5 (C-5'), 66.7 (C-1), 57.0 (C-6'-OMe or C-12-OMe), 56.9 (C-6'-OMe or C-12-OMe), 52.5 (C-3), 51.8 (C-1'), 47.1 (C-α'), 44.7 (C-8"), 43.2 (C-3'), 42.2 (C-2"), 40.4 (C—N2-Me), 38.2 (C-5"), 37.7 (C-α), 31.1 (C-4" or C-6"), 31.0 (C-4" or C-6"), 30.0 (C-4' or C-3" or C-7"), 29.9 (C-4' or C-3" or C-7"), 26.6 (C-4).

HRMS-ESI (m/z) calculated for $C_{47}H_{48}N_3O_8$ [M+H]$^+$: 782.3436; Found: 782.3436.

Example 20: Product 31

To a solution of acryloyl chloride (150 µL-1.85 mmol) and de N-hydroxysuccinimide (212 mg-1.85 mmol) in 250 µL of DMF was added trilobine 1 (3 mg-5.34 µmol) and triethylamine (10 µL-74.10 µmol). The mixture was stirred 18 hours at RT. The reaction mixture was concentrated under reduced pressure and the residue was purified by HPLC semi-preparative X-Terra RP-18, eluting with a linear gradient H$_2$O/MeCN with 1% formic acid (95.5 to 50:50), to give 31 (2.6 mg, 4.22 µmol, 79%).

(31)

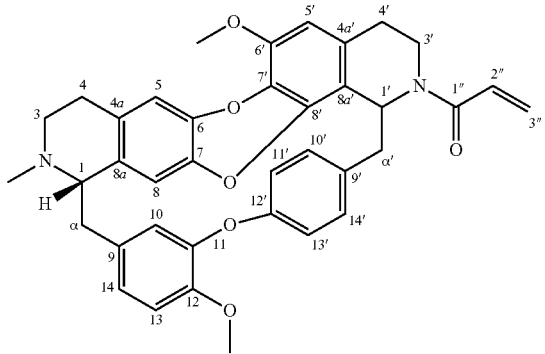

$^1$H NMR (500 MHz, DMSO-d$_6$) δ 8.04 (1H, dd, J=8.6 Hz, 1.7 Hz, H-14'), 7.16 (2H, m, H-10', H-13'), 7.02 (1H, dd, J=8.0 Hz, J=2.5 Hz, H-11'), 6.99 (1H, d, J=8.3 Hz, H-13), 6.94-6.88 (2H, m, H-2", H-14), 6.66 (1H, s, H-5), 6.63 (1H, s, H-5'), 6.47 (1H, d, J=1.9 Hz, H-10), 6.25 (1H, dd, J=16.6 Hz, J=2.2 Hz, H-3"), 6.06 (1H, s, H-8), 5.88 (1H, br, H-1'), 5.77 (1H, dd, J=10.5 Hz, J=2.2 Hz, H-3"), 4.09 (1H, m, H-3'), 3.86 (3H, s, 12-OMe), 3.79 (3H, s, 6'-OMe), 3.66 (1H, m, H-3'), 3.32 (1H, br d, J=16.0 Hz, H-α'), 3.07 (1H, br, H-1), 2.96 (1H, dd, J=15.7 Hz, J=5.5 Hz, H-α'), 2.88-2.70 (5H, m, H-3, H-4', H-α), 2.63-2.56 (2H, m, H-4), 2.46 (1H, m, H-3), 2.25 (3H, s, N2-Me).

$^{13}$C NMR (125 MHz, DMSO-d$_6$) δ 164.1 (C-1"), 153.7 (C12'), 149.7 (C-11), 146.7 (C-12), 146.2 (C-6'), 138.8 (C-6 or C-7 or C-8'), 138.6 (C-6 or C-7 or C-8'), 138.2 (C-6 or C-7 or C-8'), 137.9 (C-9'), 135.5 (C-8a), 134.7 (C-9), 130.7 (C-4a and C-10'), 130.3 (C-14'), 128.9 (C-7'), 128.5 (C2" and C-4a'), 128.1 (C-3"), 122.3 (C-13'), 121.8 (C-14), 121.4 (C-11'), 119.1 (C-8a'), 116.4 (C-10), 115.4 (C-5), 113.5 (C-8), 112.6 (C-13), 107.2 (C-5'), 67.2 (C-1), 56.0 (C-6'-OMe or C-12-OMe), 55.7 (C-6'-OMe or C-12-OMe), 49.9 (C-3), 49.7 (C-1'), 45.1 (C-α'), 42.4 (C—N2-Me), 40.4 (C-α or C-3'), 40.3 (C-α or C-3'), 28.2 (C-4'), 27.3 (C-4).

HRMS-ESI (m/z) calculated for $C_{38}H_{37}N_2O_6$ [M+H]$^+$: 617.2646; Found: 617.2654.

Example 21: Product 32

To a solution of 3-chloropropanoyl chloride (100 µL-1.04 mmol) and N-hydroxysuccinimide (12 mg-107.97 µmol) in 250 µL of DMF was added trilobine 1 (3 mg-5.34 µmol) and trimethylamine (10 µL-74.10 µmol). The mixture was stirred 48 hours at RT. The reaction mixture was concentrated under reduced pressure and the residue was purified by HPLC semi-preparative X-Terra RP-18, eluting with a linear gradient H$_2$O/MeCN with 1% formic acid (95.5 to 50:50), to give 32 (0.7 mg, 1.07 µmol, 20%).

(32)

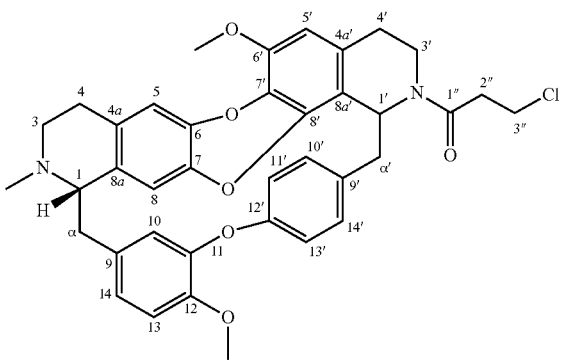

$^1$H NMR (500 MHz, MeOD) δ 7.91 (1H, dd, J=8.2 Hz, 2.0 Hz, H-14'), 7.10 (H, dd, J=8.4 Hz, J=2.6 Hz, H-13'), 7.02 (2H, m, H-10', H-13), 6.97 (1H, dd, J=8.1 Hz, J=2.0 Hz, H-14), 6.86 (1H, dd, J=8.1 Hz, J=2.5 Hz, H-11'), 6.70 (1H, s, H-5), 6.66 (1H, d, J=2.1 Hz, H-10), 6.65 (1H, s, H-5'), 6.38 (1H, s, H-8), 5.83 (1H, br dd, J=7.6 Hz, J=1.7 Hz, H-1'), 3.92 (3H, s, 12-OMe), 3.91-3.88 (2H, m, H-3' or H-3"), 3.87 (3H, s, 6'-OMe), 3.72 (2H, m, H-3' or H-3"), 3.60 (1H, br, H-1), 3.22 (1H, br d, J=14.1 Hz, H-α'), 3.11-2.71 (11H, m, H-2", H-3, H-4, H-4', H-α, H-α'), 2.43 (3H, s, N2-Me).

$^{13}$C NMR (125 MHz, MeOD) δ 171.1 (C-1"), 156.6 (C12'), 151.4 (C-11), 149.5 (C-12), 148.5 (C-6'), 142.2 (C-6 or C-7 or C-8'), 141.0 (C-6 or C-7 or C-8'), 140.0 (C-6 or C-7 or C-8'), 138.5 (C-9'), 134.1 (C-9), 132.5 (C-4a and C-14'), 132.2 (C-8a), 131.8 (C-7' and C-10'), 131.4 (C-4a'), 123.9 (C-14), 123.6 (C-13'), 122.2 (C-11'), 119.9 (C-8a'), 119.0 (C-10), 116.9 (C-5), 115.7 (C-8), 114.4 (C-13), 108.5 (C-5'), 66.9 (C-1), 57.0 (C-6'-OMe and C-12-OMe), 52.5 (C-3), 52.0 (C-1'), 46.9 (C-α'), 43.4 (C-3' or C-3"), 41.0 (C-3' or C-3"), 40.6 (C—N2-Me), 38.3 (C-α), 37.7 (C-2"), 29.5 (C-4'), 26.9 (C-4).

HRMS-ESI (m/z) calculated for $C_{38}H_{38}ClN_2O_6[M+H]^+$: 653.2398; Found: 653.2413.

Example 22: Product 33

To a solution of N,N-dicyclohexylcarbodiimide (100 μL-460 μmol) and N-hydroxysuccinimide (12 mg-107.97 μmol) in 250 μL of DMF was added trilobine 1 (3 mg-5.34 μmol) and triethylamine (10 μL-74.10 μmol). The mixture was stirred 48 hours at RT. The reaction mixture was concentrated under reduced pressure and the residue was purified by HPLC semi-preparative X-Terra RP-18, eluting with a linear gradient $H_2O$/MeCN with 1% formic acid (95.5 to 50:50), to give 33 (0.4 mg, 0.59 μmol, 11%).

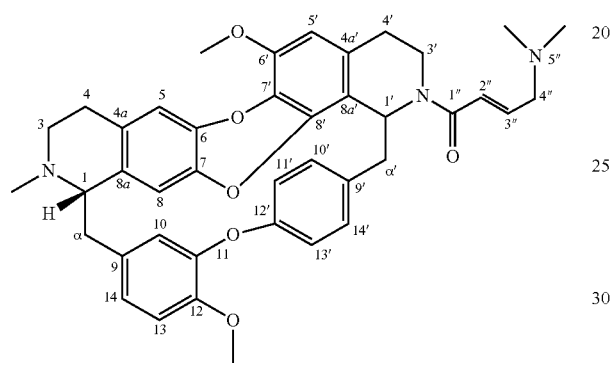

(33)

$^1$H NMR (500 MHz, MeOD) δ 8.01 (1H, dd, J=8.6 Hz, J=2.2 Hz, H-14'), 7.95 (2H, m, H-10'), 7.00 (1H, d, J=8.3 Hz), 6.95-6.86 (3H, m), 6.72 (1H, m), 6.64 (1H, s), 6.61 (1H, s), 6.27 (1H, s, H-8), 5.92 (1H, dd, J=6.6 Hz, J=1.8 Hz, H-1'), 3.93 (3H, s, 12-OMe), 3.86 (3H, s, 6'-OMe), 3.26 (2H, m), 3.02-2.64, 10H, m), 2.35-6-2.34 (9H, m, N2-Me, N5"-Me).

$^{13}$C NMR (125 MHz, MeOD) δ 167.0, 156.6, 149.3, 148.5, 142.7, 140.9, 140.2, 132.3 (C-14'), 131.8 (C-10'), 125.6, 123.6, 122.5, 119.0, 116.8, 115.4 (C-8), 114.3, 108.4 (C-5'), 68.0, 61.4, 57.0 (C-6'-OMe and C-12-O-Me), 52.3 (C-1'), 52.2, 49.9, 45.4 (C—N5"-Me), 43.3, 41.4 (C—N2-Me), 33.3, 29.7, 27.6.

HRMS-ESI (m/z) calculated for $C_{41}H_{44}N_3O_6 [M+H]^+$: 674.3225; Found: 674.3204.

Example 23: Products 1, 2, 3 and 7

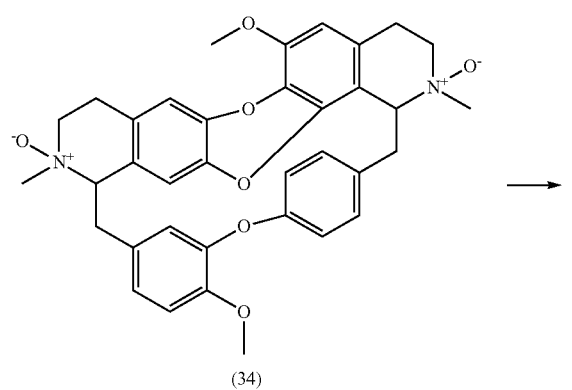

(34)

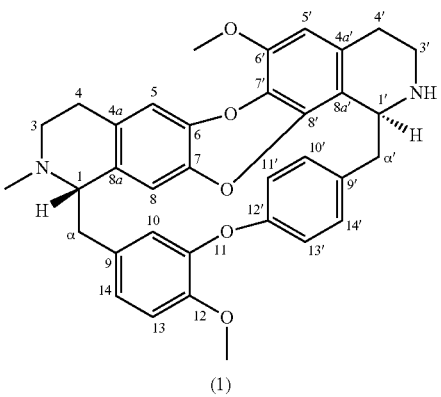

(1)

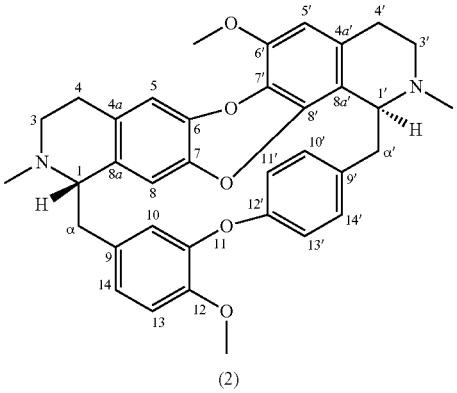

(2)

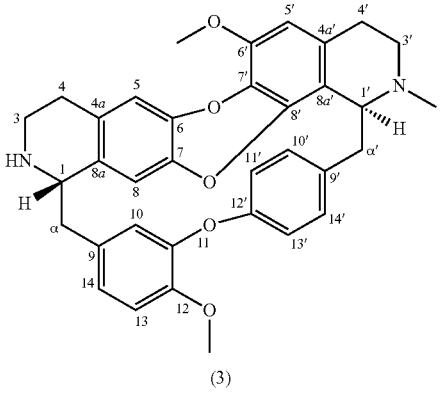

(3)

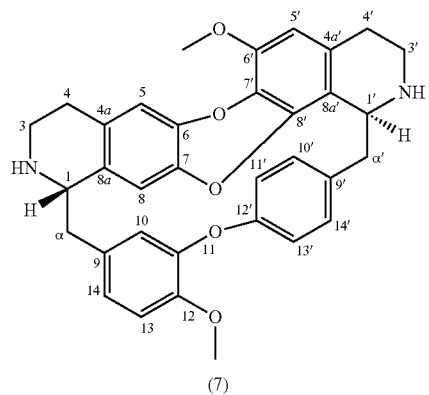 [SMILES: COc1ccc2cc1Oc1ccc(cc1)C[C@@H]1NCCc3cc(OC)c4c(c31)Oc1cc3c(cc1O4)CCN[C@H]3C2]

(7)

To an ice-cooled solution of product 34 (48.5 mg-79.77 μmol) in 800 μL of methanol was added iron sulphate heptahydrate (82 mg-294.95 μmol). The reaction was stirred 48 hours at RT. Then, the reaction mixture was concentrated under reduced pressure. The residue was dissolved with EDTA (10 mL-0.1M) and adjusted at pH=10 with ammoniac. The solution was extracted by a liquid-liquid extraction with dichloromethane. The organic phase was dried with sulfate magnesium and concentrated under reduced pressure. The residue was purified by silica gel column with a linear gradient of dichloromethane-methanol 1% NH$_3$ (100:0 to 90:10), to give nortrilobine 7 (6.4 mg, 19.08 μmol, 15%), trilobine 1 (5.6 mg, 9.96 μmol, 12%), isotrilobine 2 (3.9 mg, 6.77 μmol, 9%) and O-methylcocsoline 3 (4 mg, 7.12 μmol, 9%).

(1)

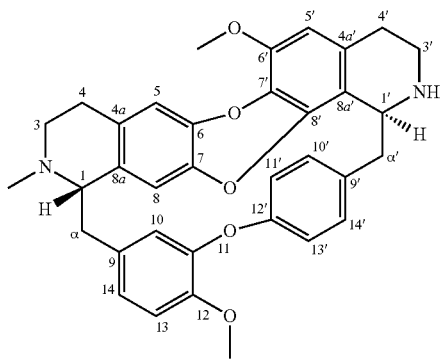

$^1$H NMR (500 MHz, MeOD) δ 7.64 (1H, dd, J=8.3 Hz, J=1.9 Hz, H-14'), 7.15 (2H, m, H-10', H-13'), 6.96 (1H, d, J=8.3 Hz, H-13), 6.93 (1H, dd, J=8.3 Hz, J=2.7 Hz, H-11'), 6.87 (1H, dd, J=8.1 Hz, J=2.0 Hz, H-14), 6.52 (1H, s, H-5), 6.49 (1H, d, J=2.0 Hz, H-10), 6.43 (1H, s, H-5'), 6.07 (1H, s, H-8), 4.27 (1H, t, J=3.3 Hz, H-1'), 3.92 (3H, s, 12-OMe), 3.78 (3H, s, 6'-OMe), 3.27 (1H, m, H-α'), 3.22 (1H, m, H-1), 3.15-3.10 (2H, m, H-3'), 2.92-2.56 (9H, m, H-3, H-4, H-4', H-α, H-α'), 2.39 (3H, s, N2-Me).

$^{13}$C NMR (125 MHz, MeOD) δ 155.7 (C-12'), 151.8 (C-11), 148.8 (C-12), 147.8 (C-6'), 141.2 (C-6 or C-7 or C-9'), 141.0 (C-6 or C-7 or C-9'), 140.1 (C-8'), 136.4 (C-9), 136.2 (C-8a), 132.5 (C-10'), 131.0 (C-4a), 130.8 (C-7'), 129.8 (C-4a'), 129.6 (C-14'), 123.5 (C-13'), 123.2 (C-14), 122.8 (C-11'), 122.4 (C-8a'), 118.3 (C-10), 116.7 (C-5), 115.3 (C-8), 114.1 (C-13), 108.4 (C-5'), 68.8 (C-1), 56.9 (C-6'-OMe), 56.8 (C-12-OMe), 54.7 (C-1'), 50.5 (C-3), 45.6 (C-α'), 42.9 (C—N2-Me), 41.9 (C-α'), 39.3 (C-3'), 28.7 (C-4'), 28.1 (C-4).

HRMS-ESI (m/z) calculated for C$_{35}$H$_{35}$N$_2$O$_5$ [M+H]$^+$: 563.2540; Found: 563.2541.

(2)

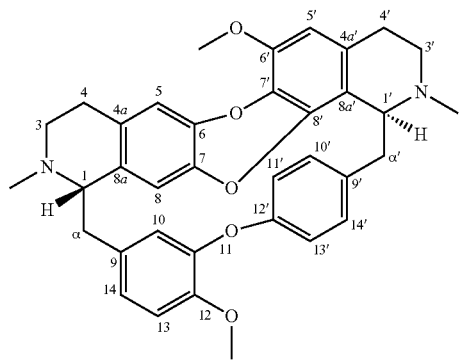

$^1$H NMR (500 MHz, MeOD) δ 7.63 (1H, dd, J=8.4 Hz, J=2.0 Hz, H-14'), 7.18 (1H, dd, J=7.8 Hz, J=2.0 Hz, H-10'), 7.16 (1H, dd, J=8.2 Hz, J=2.5 Hz, H-13'), 6.98 (1H, d, J=8.3 Hz, H-13), 6.95 (1H, dd, J=8.2 Hz, J=2.8 Hz, H-11'), 6.91 (1H, dd, J=8.3 Hz, J=2.0 Hz, H-14), 6.58 (1H, s, H-5), 6.56 (1H, d, J=1.9, H-10), 6.49 (1H, s, H-5'), 6.13 (1H, s, H-8), 4.10 (1H, m, H-1'), 3.93 (3H, s, 12-OMe), 3.83 (3H, s, 6'-OMe), 3.35 (1H, m, H-α'), 3.21 (1H, m, H-1), 3.17 (H, m, H-3'), 3.00-2.88 (4H, m, H-3, H-3', H-4', H-α), 2.81-2.60 (5H, H-3, H-4, H-4', H-α, H-α'), 2.57 (3H, s, N2'-Me), 2.37 (3H, s, N2-Me).

$^{13}$C NMR (125 MHz, MeOD) δ 156.0 (C-12'), 151.9 (C-11), 148.9 (C-12), 148.0 (C-6'), 141.4 (C-6 or C-7 or C-8' or C-9'), 141.0 (C-6 or C-7 or C-8' or C-9'), 140.8 (C-6 or C-7 or C-8' or C-9'), 140.5 (C-6 or C-7 or C-8' or C-9'), 136.2 (C-9), 135.8 (C-8a), 132.6 (C-10'), 131.5 (C-4a) 130.9 (C-7'), 130.0 (C-14'), 128.8 (C-4a'), 123.8 (C-13'), 123.3 (C-13), 122.9 (C-11'), 121.1 (C-8a'), 118.4 (C-1), 116.8 (C-5), 115.2 (C-8), 114.2, C-13), 108.4 (C-5'), 68.9 (C-1), 61.5 (C-1'), 56.9 (C-6'-OMe and C-12-OMe), 51.8 (C-3), 46.0 (C-3'), 42.6 (C—N2-Me), 42.4 (C-α'), 42.0 (C—N2'-Me), 41.6 (C-α), 28.1 (C-4), 24.6 (C-4').

HRMS-ESI (m/z) calculated for C$_{36}$H$_{37}$N$_2$O$_5$ [M+H]$^+$: 577.2697; Found: 577.2698.

(3)

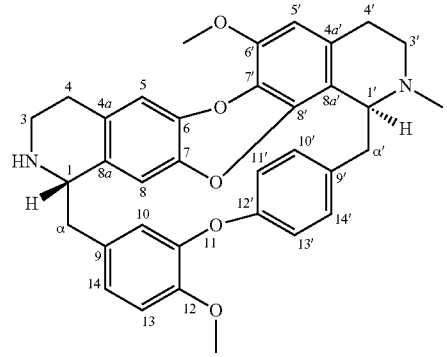

$^1$H NMR (500 MHz, CDCl$_3$) δ 7.55 (1H, dd, J=8.3 Hz, J=2.1 Hz, H-14'), 7.25 (1H, dd, J=8.3 Hz, J=2.7 Hz, H-13'), 7.14 (1H, dd, J=8.3 Hz, J=2.1 Hz, H-10'), 6.91 (3H, m, H-11', H-13, H-14), 6.65 (1H, s, H-5), 6.64 (1H, d, J=1.9 Hz, H-10), 6.35 (H, s, H-5'), 6.21 (1H, s, H-8), 4.00 (1H, m, H-1'), 3.99 (3H, s, 12-OMe), 3.88 (3H, s, 6'-OMe), 3.62 (1H, d, J=4.6 Hz, H-1), 3.34 (1H, d, J=14.5 Hz, H-α'), 3.20-3.11 (2H, m, H-3, H-3'), 3.03-2.90 (4H, H-3, H-3', H-4', H-α), 2.78-2.72 (2H, m, H-4, H-α), 2.66 (1H, m, H-α'), 2.63 (3H, s, N2-Me), 2.59-2.50 (2H, m, H-4, H-4').

$^{13}$C NMR (125 MHz, CDCl$_3$) δ 154.9 (C-12'), 150.2 (C-6), 147.7 (C-11), 146.2 (C-6'), 139.9 (C-6 or C-7 or C-8' or C-9'), 139.6 (C-6 or C-7 or C-8' or C-9'), 139.5 (C-6 or C-7 or C-8' or C-9'), 139.3 (C-6 or C-7 or C-8' or C-9'), 136.4 (C-8a), 134.7 (C-9), 131.7 (C-10'), 131.2 (C-4a), 129.7 (C-7'), 128.9 (C-14'), 127.6 (C4a'), 122.6 (C-13'), 122.1 (C-14), 121.5 (C-11'), 121.1 (C-8a'), 117.9 (C-10), 116.5 (C-5), 113.2 (C-8), 112.7 (C-13), 106.9 (C-5'), 60.7 (C-1 and C-1'), 56.5 (C-6'-OMe and C-12-OMe), 45.1 (C-3'), 44.1 (C-α), 43.2 (C-3), 42.4 (C—N2-Me), 41.7 (C-α'), 29.0 (C-4), 24.3 (C-4').

HRMS-ESI (m/z) calculated for C$_{35}$H$_{35}$N$_2$O$_5$ [M+H]$^+$: 563.2540; Found: 563.2544.

(7)

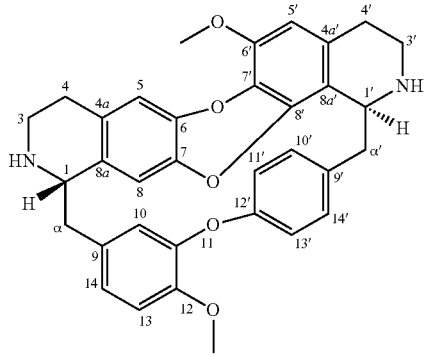

¹H NMR (500 MHz, MeOD) δ 7.58 (1H, dd, J=8.4 Hz, J=2.2 Hz, H-14'), 7.20 (1H, dd, J=8.3 Hz, J=2.6 Hz, H-13'), 7.07 (1H, dd, J=8.3 Hz, J=2.2 Hz, H-10'), 7.04 (1H, d, J=8.4 Hz, H-13), 7.02 (1H, dd, J=8.3 Hz, J=2.0 Hz, H-14), 6.74 (1H, dd, J=8.4 Hz, J=2.5 Hz, H-11'), 6.62 (1H, s, H-5), 6.61 (1H, d, J=1.8 Hz, H-10), 6.57 (1H, s, H-5'), 6.27 (1H, s, H-8), 4.37 (1H, dd, J=5.8 Hz, J=1.5 Hz, H-1'), 3.91 (3H, s, 12-OMe), 3.80 (1H, m, H-1), 3.79 (3H, s, 6'-OMe), 3.45-3.34 (3H, m, H3', H-α'), 3.19 (1H, m, H-3), 3.12-2.98 (H-3, H-4', Hα), 2.93-2.88 (3H, m, H-4', H-α, H-α'), 2.83 (1H, m, H-4), 2.71 (1H, m, H-4).

¹³C NMR (125 MHz, MeOD) δ 157.3 (C-12'), 151.3 (C-11), 149.8 (C-12), 148.7 (C-6'), 142.0 (C-6 or C-7), 141.0 (C6 or C-7), 139.9 (C-8'), 138.4 (C-9'), 133.8 (C-9), 133.5 (C-8a), 132.7 (C-4a and C-10'), 130.9 (C-7'), 130.5 (C-14'), 128.6 (C-4a'), 124.2 (C-14), 123.6 (C-13'), 122.3 (C-11'), 119.6 (C-10), 119.2 (C-8a'), 117.2 (C-5), 114.8 (C-13), 114.6 (C-8), 108.9 (C-5'), 59.7 (C-1), 57.0 (C-6'-OMe or C-12-OMe), 56.9 (C-6'-OMe or C-12-OMe), 54.3 (C-1'), 44.2 (C-α'), 42.6 (C-3), 40.8 (C-α), 38.2 (C-3'), 27.6 (C-4), 26.9 (C-4').

HRMS-ESI (m/z) calculated for $C_{34}H_{33}N_2O_5$ [M+H]⁺: 549.2384; Found: 549.2388.

Example 24: Product 41

To a solution of nortrilobine 7 (7.5 mg-13.69 µmol) in 500 µL of tetrahydrofuran was added 3-(diethylamino)propylisothiocyanate (5 µL-29.02 µmol) and N-ethyl-N-isopropylpropan-2-amine (5 µL-29.40 µmol). The mixture was stirred 24 hours at RT in inert argon atmosphere. The reaction mixture was concentrated under reduced pressure and the residue was purified by HPLC semi-preparative X-Terra RP-18, eluting with a linear gradient H₂O/MeCN with 1% formic acid (80:20 to 0:100), to give 41 (6.2 mg, 6.95 µmol, 51%).

¹H NMR (500 MHz, MeOD) δ 8.35 (1H, br, H-14'), 7.12 (1H, br, H-10'), 7.07 (1H, br, H-13'), 7.00 (1H, br, H-11'), 6.97 (1H, d, J=8.2 Hz, H-13), 6.80 (1H, br d, J=8.3 Hz, H-14), 6.75 (1H, br, H-10), 6.60 (1H, br s, H-5), 6.50 (1H, br s, H-5'), 6.03 (1H, br s, H-8), 3.94 (3H, s, 12-OMe), 3.84 (3H, s, 6'-OMe), 3.80 (2H, m, H-3" or H-3'''), 3.71-3.60 (4H, m, H-3', H-3" or H-3'''), 3.47 (1H, br d, J=15.9 Hz, H-α'), 3.14-3.05 (8H, m, H-7", H-7''', H-9", H-9'''), 3.03-2.87 (8H, m, H-4', H-5", H-5''', H-α, H-α'), 2.79-2.68 (2H, m, H-4, H-4'), 2.58 (1H, br d, J=16.3 Hz, H-4), 2.06 (2H, br, H-4" or H-4'''), 1.91 (2H, br, H-4" or H-4'''), 1.24 (12H, br t, J=7.1 Hz, H-8", H-10'').

¹³C NMR (125 MHz, MeOD) δ 182.1 (C-1" or C-1'''), 182.0 (C-1" or C-1'''), 156.7 (C12'), 151.7 (C-11), 149.5 (C-12), 148.2 (C-6'), 141.6 (C-6 or C-7), 141.1 (C-6 or C-7), 140.4 (C-8'), 139.4 (C-9'), 135.7 (C-4a), 135.2 (C-9), 132.2 (C-10' and C-14'), 131.4 (C-8a), 130.9 (C-7'), 129.9 (C-4a'), 124.2 (C-14), 123.3 (C-13'), 122.5 (C-11'), 121.4 (C-8a'), 118.7 (C-10), 117.1 (C-5), 115.0 (C-8), 114.1 (C-13), 108.5 (C-5'), 62.7 (C-1), 59.1 (C-1'), 57.0 (C-6'-OMe and C-12-OMe), 50.6 (C-5" or C-5'''), 50.5 (C-5" or C-5'''), 48.2 (C-7" or C-7''' or C-9" or C-9'''), 48.0 (C-7" or C-7''' or C-9" or C-9'''), 46.2 (C-α'), 45.9 (C-α), 44.1 (C3" or C3''''), 43.9 (C3" or C3''''), 42.8 (C-3'), 28.7 (C-4), 27.9 (C-4'), 25.7 (C-4" and C-4'''), 9.6 (C-8" or C-8''' or C-10" or C-10'''), 9.5 (C-8" or C-8''' or C-10" or C-10''').

HRMS-ESI (m/z) calculated for $C_{50}H_{64}N_6O_5S_2$[M+H]⁺: 893.4452; Found: 893.4450.

Example 25: Product 42

To a solution of O-methylcosoline 3 (6.3 mg-11.21 µmol) in 300 µL of tetrahydrofuran was added N,N-diethyl-3-isothiocyanatopropan-1-amine (3 µL-11.07 µmol) and triethylamine (3 µL-22.22 µmol). The mixture was stirred 20 hours at RT. The reaction mixture was concentrated under reduced pressure and the residue was purified by HPLC semi-preparative X-Terra RP-18, eluting with a linear gradient H₂O/MeCN with 1% formic acid (80:20 to 0:100), to give 42 (6 mg, 8.17 µmol, 73%).

(41)

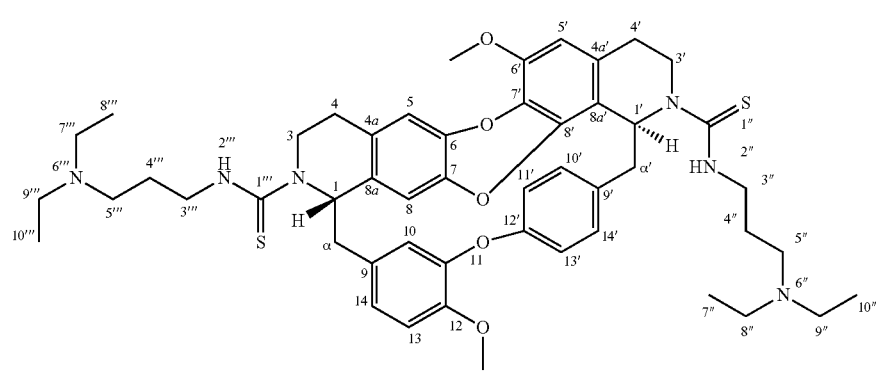

(42)

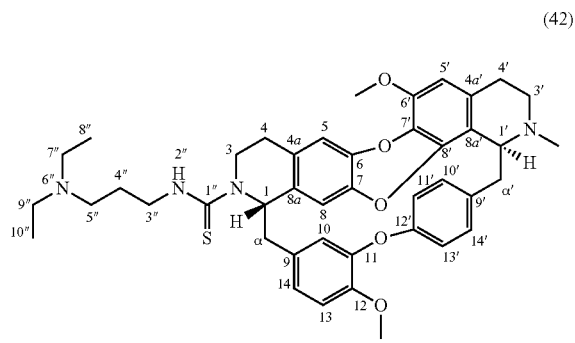 [SMILES: CCN(CC)CCCNC(=S)N1CCc2cc3c4cc2[C@@H]1Cc1ccc(OC)c(c1)Oc1ccc(cc1)C[C@H]1c2c(cc(OC)c(c2O4)O3)CCN1C]

¹H NMR (500 MHz, MeOD) δ 7.66 (1H, br dd, J=8.4 Hz, J=1.6 Hz, H-14'), 7.21 (2H, dd, J=8.5 Hz, J=2.3 Hz, H-10', H-13'), 7.09 (1H, br dd, J=8.3 Hz, J=2.5 Hz, H-11'), 6.94 (1H, d, J=8.1 Hz, H-13), 6.78-6.74 (2H, m, H-10, H14), 6.60 (1H, s, H-5), 6.50 (1H, s, H-5'), 5.98 (1H, s, H-8), 4.20 (1H, br t, J=3.2 Hz, H-1'), 3.94 (3H, s, 12-OMe), 3.82 (3H, s, 6'-OMe), 3.69 (2H, m, H-3"), 3.39 (1H, br d, J=15.6 Hz, H-α'), 3.28 (1H, m, H-3'), 3.20 (4H, q, J=7.3 Hz, H-7", H-9"), 3.12-3.06 (3H, m, H-3', H-α), 3.12-3.06 (3H, m, H-3', H-5"), 2.99 (1H, m, H-4'), 2.92-2.87 (2H, m, H-α), 2.86-2.74 (3H, m, H-4, H-4', H-α'), 2.67 (3H, s, N2'-Me), 2.63 (1H, m, H-4), 1.97 (2H, br, H-4"), 1.28 (6H, br t, J=7.5 Hz, H-8", H-10").

¹³C NMR (125 MHz, MeOD) δ 182.3 (C-1"), 156.7 (C12'), 151.7 (C-11), 149.5 (C-12), 148.4 (C-6'), 141.6 (C-6 or C-7 or C-8'), 141.2 (C-6 or C-7 or C-8'), 140.8 (C-6 or C-7 or C-8'), 140.2 (C-9'), 135.8 (C-8a), 135.1 (C-9), 132.6 (C-10'), 131.4 (C-4a or C-7'), 131.2 (C-4a or C-7'), 129.5 (C-14'), 128.3 (C-4a'), 124.2 (C-14), 123.8 (C-13'), 122.9 (C-11'), 119.0 (C-8a'), 118.5 (C-10), 117.0 (C-5), 115.0 (C-8), 114.0 (C-13), 108.2 (C-5'), 62.8 (C-1), 62.0 (C-1'), 57.0 (C-6'-OMe or C-12-OMe), 56.9 (C-6'-OMe or C-12-OMe), 50.3 (C-5"), 48.1 (C-7" and C-9"), 46.5 (C-3'), 46.1 (C-α), 43.6 (C-3"), 42.5 (C-α'), 41.5 (C—N2'-Me), 28.6 (C-4), 25.5 (C-4"), 24.0 (C-4'), 9.2 (C-8" and C-10").

HRMS-ESI (m/z) calculated for $C_{43}H_{51}N_4O_5S$ [M+H]⁺: 735.3575; Found: 735.3559.

Example 26: Product 43

Step 1: Synthesis of N-methyl-carbamoylimidazole

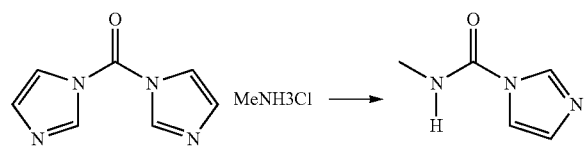

To a solution of 1,1-carbonyldiimidazole (2 g-12.33 mmol) in a mixture of DMF-MeCN (8 mL, (2:6)) was added MeNH₃Cl (0.690 g-10.30 mmol). The reaction mixture was stirred 2 hours at RT. The reaction mixture was concentrated under reduced pressure and the residue was purified by silica gel column with a linear gradient of dichloromethane-methanol (100:0 to 96:4), to give N-methyl-carbamoylimidazole (808 mg, 6.46 mmol, 68%)

Step 2: Addition of N-methyl-carbamoylimidazole to Nortrilobine (Product 7)

To a solution of nortrilobine 7 (5 mg-9.12 µmol) in 500 µL of dicholoromethane was added N-methyl-carbamoylimidazole (3 mg-23.98 µmol) and triethylamine (4 µL-29.63 µmol). The mixture was stirred 24 hours at RT. The reaction mixture was concentrated under reduced pressure and the residue was purified by HPLC semi-preparative X-Terra RP-18, eluting with a linear gradient H₂O/MeCN with 0.02% triethylamine (80:20 to 0:100), to give 43 (3.3 mg, 4.98 µmol, 55%).

(43)

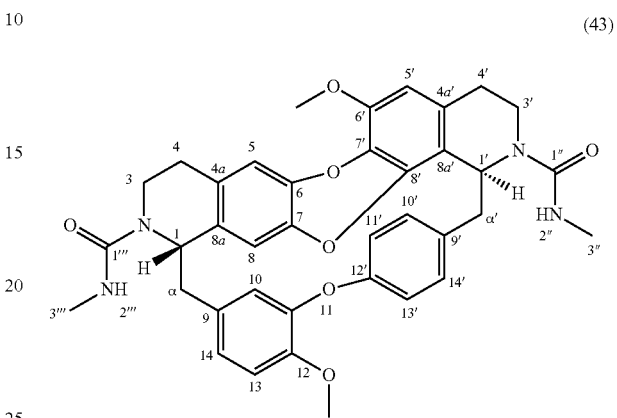

¹H NMR (500 MHz, CDCl₃) δ 8.13 (1H, br dd, J=8.5 Hz, J=1.6 Hz, H-14'), 7.30 (1H, dd, J=8.5 Hz, J=2.7 Hz, H-13'), 7.16 (1H, dd, J=8.2 Hz, J=2.2 Hz, H-10'), 7.06 (1H, dd, J=8.2 Hz, J=2.7 Hz, H-11'), 6.91 (1H, d, J=8.1 Hz, H-13), 6.80 (1H, dd, J=8.2 Hz, J=2.2 Hz, H-14), 6.65 (1H, d, J=2.1 Hz, H-10), 6.64 (1H, s, H-5), 6.33 (1H, s, H-5'), 6.13 (1H, s, H-8), 5.73 (1H, br d, H-1'), 4.58 (1H, q, J=4.5 Hz, 2"-NH), 4.43 (1H, dd, J=13.8 Hz, J=5.0 Hz, H-3), 4.34 (1H, br d, H-1), 4.06 (1H, q, J=4.6 Hz, 2'''-NH), 4.00 (3H, s, 12-OMe), 3.86 (3H, s, 6'-OMe), 3.77 (1H, br, H-3'), 3.49 (1H, m, H-3'), 3.65 (1H, br d, J=15.0 Hz, H-α'), 3.11 (1H, dd, J=14.9 Hz, J=3.4 Hz, H-α), 2.97-2.91 (3H, m, H-3, H-4', H-α'), 2.90 (3H, d, J=4.7 Hz, 3'''-NHMe), 2.82 (1H, dd, J=14.9 Hz, J=3.2 Hz, H-α), 2.77-2.68 (2H, m, H-4, H-4'), 2.65 (3H, d, J=4.6 Hz, 3"-NHMe), 2.50 (1H, br d, J=15.4 Hz, H-4).

¹³C NMR (125 MHz, CDCl₃) δ 157.7 (C-1"), 157.5 (C-1'''), 154.0 (C12'), 151.0 (C-11), 147.9 (C-12), 146.6 (C-6'), 140.1 (C-6 or C-7), 139.8 (C-6 or C-7), 139.2 (C-8' or C-9'), 139.1 (C-8' or C-9'), 134.5 (C-9), 133.6 (C-8a), 131.1 (C-10'), 130.8 (C-4a), 130.4 (C-14'), 130.0 (C-7'), 128.2 (C-4a'), 123.4 (C-13'), 121.5 (C-11' and C-14), 120.8 (C-8a'), 116.6 (C-10), 116.2 (C-5), 114.0 (C-8), 112.1 (C-13), 106.7 (C-5'), 59.3 (C-1), 56.6 (C-6'-OMe), 56.4 C-12-OMe), 52.5 (C-1'), 46.4 (C-α), 45.7 (C-α'), 39.7 (C-3'), 37.6 (C-3), 28.4 (C-4), 28.0 (C-3"), 27.6 (C-3'''), 27.3 (C-4').

HRMS-ESI (m/z) calculated for $C_{38}H_{38}N_4NaO_7$ [M+Na]⁺: 685.2633; Found: 685.2616.

Example 27: Product 44

To a solution of trilobine 1 (12 mg-21.35 µmol) in 500 µL of dicholoromethane was added N-methyl-carbamoylimidazole (2.7 mg-21.58 µmol) and triethylamine (4 µL-29.63 µmol). The mixture was stirred 24 hours at RT. The reaction mixture was concentrated under reduced pressure and the residue was purified by HPLC semi-preparative X-Terra RP-18, eluting with a linear gradient H₂O/MeCN with 0.02% triethylamine (55:45 to 40:60), to give 44 (4.7 mg, 7.59 µmol, 36%).

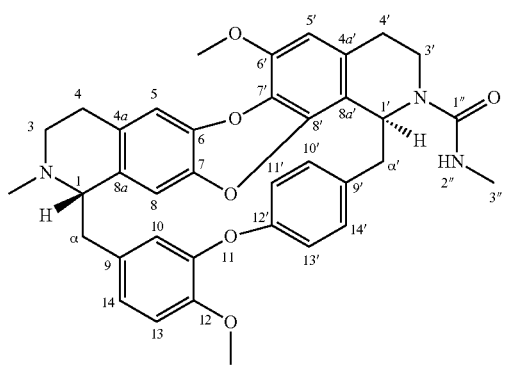

(44)

¹H NMR (500 MHz, MeOD) δ 7.96 (1H, br dd, J=8.5 Hz, J=1.7 Hz, H-14'), 7.06 (1H, dd, J=8.4 Hz, J=2.5 Hz, H-13'), 7.00 (1H, m, H-10'), 6.99 (1H, d, J=8.3 Hz, H-13), 6.92 (1H, dd, J=8.3 Hz, J=2.0 Hz, H-14), 6.87 (1H, dd, J=8.1 Hz, J=2.4 Hz, H-11'), 6.62 (1H, d, J=1.8 Hz, H-10), 6.58 (1H, s, H-5), 6.56 (1H, s, H-5'), 6.22 (1H, s, H-8), 5.66 (1H, br d, J=6.3 Hz, H-1'), 3.91 (3H, s, 12-OMe), 3.84 (3H, s, 6'-OMe), 3.56 (2H, m, H-3'), 3.25 (2H, m, H-1, H-α'), 2.94-2.82 (6H, m, H-3, H-4', H-α, H-α'), 2.80 (3H, s, 3"-NHMe), 2.76 (2H, m, H-3, H-4), 2.62 (1H, m, H-4), 2.31 (3H, s, N2-Me).

¹³C NMR (125 MHz, MeOD) δ 160.3 (C-1"), 156.6 (C12'), 151.6 (C-11), 149.3 (C-12), 148.2 (C-6'), 141.4 (C-6 or C-7), 140.8 (C-6 or C-7), 140.0 (C-8'), 139.3 (C-9'), 136.0 (C-9), 135.1 (C-8a), 132.1 (C-4a and C-14'), 131.7 (C-10'), 131.1 (C-4a' or C-7'), 131.0 (C-4a' or C-7'), 123.6 (C-14), 123.4 (C-13'), 122.2 (C-11'), 121.2 (C-8a'), 119.0 (C-10), 116.8 (C-5), 115.3 (C-8), 114.3 (C-13), 108.3 (C-5'), 68.1 (C-1), 57.0 (C-6'-OMe and C-12-OMe), 53.0 (C-1'), 52.2 (C-3), 47.1 (C-α'), 41.5 (C—N2-Me and C-3'), 40.3 (C-α), 28.7 (C-4'), 28.0 (C-3"), 27.6 (C-4).

HRMS-ESI (m/z) calculated for C₃₇H₃₈N₃O₆ [M+H]⁺: 685.2755; Found: 620.2753.

Example 28: Product 45

To a solution of O-methylcocsoline 3 (12 mg-21.35 μmol) in 500 μL of dicholoromethane was added N-methyl-carbamoylimidazole (2.7 mg-21.58 μmol) and triethylamine (4 μL-29.63 μmol). The mixture was stirred 24 hours at RT. The reaction mixture was concentrated under reduced pressure and the residue was purified by HPLC semi-preparative X-Terra RP-18, eluting with a linear gradient H₂O/MeCN with 0.02% triethylamine (55:45 to 40:60), to give 45 (3.8 mg, 6.14 μmol, 29%).

(45)

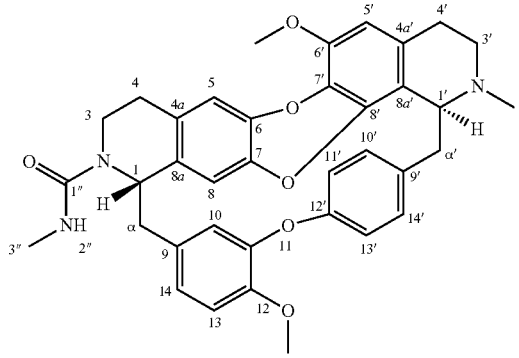

¹H NMR (500 MHz, MeOD) δ 7.63 (1H, br dd, J=8.7 Hz, J=1.3 Hz, H-14'), 7.18 (2H, m, H-10', H-13'), 7.01 (1H, dd, J=8.3 Hz, J=2.5 Hz, H-11'), 6.95 (1H, d, J=8.3 Hz, H-13), 6.75 (1H, dd, J=8.0 Hz, J=1.7 Hz, H-14), 6.61 (1H, d, J=1.7 Hz, H-10), 6.53 (1H, s, H-5), 6.45 (1H, s, H-5'), 6.05 (1H, s, H-8), 4.84 (1H, br, H-1), 4.0 (2H, m, H-1', H-3), 3.93 (3H, s, 12-OMe), 3.81 (3H, s, 6'-OMe), 3.29 (1H, m, H-α'), 3.14 (1H, m, H-3'), 3.05 (1H, m, H-3), 2.94-2.88 (2H, m, H-3', H-4'), 2.82 (1H, m, H-α), 2.76-2.66 (3H, m, H-4, H-α, H-α'), 2.64 (3H, s, 3"-NHMe), 2.55 (3H, s, N2'-Me), 2.49 (1H, m, H-4).

¹³C NMR (125 MHz, MeOD) δ 160.3 (C-1"), 156.6 (C12'), 152.0 (C-11), 149.5 (C-12), 148.3 (C-6'), 141.8 (C-6 or C-7 or C-8' or C-9'), 141.6 (C-6 or C-7 or C-8' or C-9'), 141.5 (C-6 or C-7 or C-8' or C-9'), 141.2 (C-6 or C-7 or C-8' or C-9'), 136.5 (C-8a or C-9), 136.4 (C-8a or C-9), 133.2 (C-10'), 131.7 (C-4a), 131.3 (C-7'), 129.7 (C-14'), 129.3 (C-4a'), 123.9 (C-13' and C-14), 123.1 (C-11'), 121.0 (C-8a'), 118.5 (C-10), 117.4 (C-5), 115.3 (C-8), 114.6 (C-13), 108.5 (C-5'), 62.4 (C-1'), 59.1 (C-1), 57.3 (C-6'-OMe or C-12-OMe), 57.2 (C-6'-OMe or C-12-OMe), 47.7 (C-α), 46.7 (C-3'), 43.5 (C-α'), 42.2 (C—N2'-Me), 39.7 (C-3), 29.2 (C-4), 28.2 (C-3"), 24.5 (C-4').

HRMS-ESI (m/z) calculated for C₃₇H₃₈N₃O₆ [M+H]⁺: 685.2755; Found: 620.2749.

Example 29: Product 46

To a solution of O-methylcocsoline 3 (10 mg-17.79 μmol) in 500 μL of THF was added methyl isothiocyanate (2.5 μL-36.55 μmol) and N,N-diisopropylethylamine (5 μL-29.40 μmol). The mixture was stirred 24 hours at RT. The reaction mixture was concentrated under reduced pressure and the residue was purified by HPLC semi-preparative X-Terra RP-18, eluting with a linear gradient H₂O/MeCN with 0.02% triethylamine (80:20 to 0:100), to give 46 (7.2 mg, 11.34 μmol, 64%).

(46)

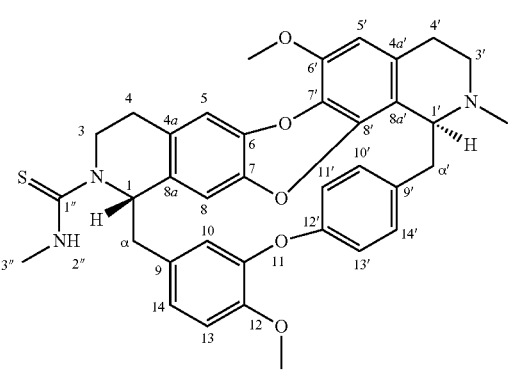

¹H NMR (500 MHz, CDCl₃) δ 7.66 (1H, dd, J=8.3 Hz, J=2.0 Hz, H-14'), 7.26 (1H, dd, J=8.3 Hz, J=2.7 Hz, H-13'), 7.21 (1H, dd, J=8.3 Hz, J=2.1 Hz, H-10'), 7.08 (1H, dd, J=8.4 Hz, J=2.7 Hz, H-11'), 6.91 (1H, d, J=8.3 Hz, H-13), 6.78 (1H, dd, J=8.0 Hz, J=2.1 Hz, H-14), 6.67 (2H, m, H-5, H-10), 6.34 (1H, s, H-5'), 6.04 (1H, s, H-8), 5.42 (1H, br d, J=11.3 Hz, H-3), 5.24 (1H, q, J=4.2 Hz, 2"-NH), 4.54 (1H, br, H-1), 4.07 (1H, br t, J=3.0 Hz, H-1'), 4.01 (3H, s, 12-OMe), 3.87 (3H, s, 6'-OMe), 3.36 (1H, br dd, J=15.9 Hz, J=2.6 Hz, H-α'), 3.19-3.12 (3H, m, H-3, H-3', H-α), 2.94 (3H, d, J=4.3 Hz, 3"-NHMe), 2.92-2.86 (3H, m, H-3', H-4, H-4'), 2.82 (1H, dd, J=15.2 Hz, J=3.6 Hz, H-α), 2.74 (1H, dd, J=16.0 Hz, J=3.7 Hz, H-α'), 2.62 (3H, s, N2'-Me), 2.57-2.49 (2H, m, H-4, H-4').

$^{13}$C NMR (125 MHz, CDCl$_3$) δ 182.2 (C-1''), 153.4 (C12'), 151.4 (C-11), 148.2 (C-12), 146.3 (C-6'), 140.9 (C-9'), 140.5 (C-6 or C-7), 140.2 (C-6 or C-7), 139.3 (C-8'), 133.4 (C-9), 132.4 (C-8a), 131.6 (C-10'), 133.7 (C-4a), 129.6 (C-7'), 128.7 (C-14'), 128.13 (C-4a'), 123.0 (C-13'), 121.8 (C-11'), 121.5 (C-14), 120.7 (C-8a'), 116.3 (C-5 and C-10), 113.6 (C-8), 112.1 (C-13), 106.8 (C-5'), 61.7 (C-1), 60.5 (C-1'), 56.5 (C-6'-OMe), 56.4 (C-12-OMe), 45.6 (C-3' or C-α), 45.5 (C-3' or C-α), 44.1 (C-3), 42.2 (C-α' and C—N2'-Me), 32.8 (C-3''), 27.8 (C-4), 24.0 (C-4').

HRMS-ESI (m/z) calculated for C$_{37}$H$_{38}$N$_3$O$_5$S [M+H]$^+$: 636.2527; Found: 636.2524.

Example 30: Product 47

To a solution of nortrilobine 7 (5 mg-9.12 μmol) in 500 μL of THF was added methyl isothiocyanate (2 μL-29.24 μmol) and N,N-diisopropylethylamine (3 μL-17.64 μmol). The mixture was stirred 24 hours at RT. The reaction mixture was concentrated under reduced pressure and the residue was purified by HPLC semi-preparative X-Terra RP-18, eluting with a linear gradient H$_2$O/MeCN with 0.02% triethylamine (80:20 to 0:100), to give 47 (3.2 mg, 4.61 μmol, 51%).

(47)

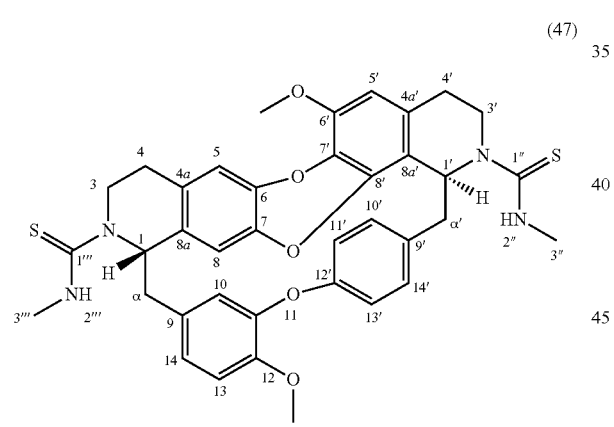

$^1$H NMR (500 MHz, CDCl$_3$) δ 8.31 (1H, br, H-14'), 7.25 (1H, dd, J=8.3 Hz, J=2.4 Hz, H-13'), 7.14 (1H, br dd, J=8.3 Hz, J=2.3 Hz, H-10'), 7.05 (1H, dd, J=8.1 Hz, J=2.6 Hz, H-11'), 6.93 (1H, d, J=8.3 Hz, H-13), 6.81 (1H, dd, J=8.3 Hz, J=1.8 Hz, H-14), 6.77 (1H, d, J=1.9 Hz, H-10), 6.69 (1H, s, H-5), 6.57 (1H, br, H-1'), 6.37 (1H, s, H-5'), 6.17 (1H, s, H-8), 5.80 (1H, q, J=4.4 Hz, 2''-NH), 5.45 (1H, br d, J=12.0 Hz, H-3), 5.20 (1H, q, J=4.3 Hz, 2''-NH), 4.53 (1H, br, H-1), 4.26 (1H, br, H-3'), 4.01 (3H, s, 12-OMe), 3.87 (3H, s, 6'-OMe), 3.70 (1H, m, H-3'), 3.42 (1H, br d, J=14.5 Hz, H-α'), 3.28 (1H, m, H-α), 3.24 (3H, d, J=4.4 Hz, 3''-NHMe), 3.15 (1H, td, J=12.8 Hz, J=2.6 Hz, H-3), 3.05 (1H, dd, J=14.9 Hz, J=5.3 Hz, H-α'), 2.99 (1H, m, H-4'), 2.93 (3H, d, J=4.5 Hz, 3''-NHMe), 2.90 (1H, m, H-4), 2.87-2.79 (2H, m, H-4', H-α), 2.57 (1H, br d, J=16.4 Hz, H-4).

$^{13}$C NMR (125 MHz, CDCl$_3$) δ 182.2 (C-1'''), 182.0 (C-1''), 154.3 (C12'), 151.1 (C-11), 148.4 (C-12), 146.9 (C-6'), 140.5 (C-6 or C-7), 140.0 (C-6 or C-7), 139.2 (C-8'), 137.8 (C-9'), 133.3 (C-9), 132.5 (C-8a), 131.5 (C-14'), 133.3 (C-4a), 130.9 (C-10'), 130.1 (C-7'), 128.3 (C-4a'), 123.0 (C-13'), 121.8 (C-14), 121.5 (C-11'), 120.0 (C-8a'), 116.9 (C-10), 116.3 (C-5), 113.8 (C-8), 112.2 (C-13), 106.9 (C-5'), 61.8 (C-1), 57.0 (C-1'), 56.6 (C-6'-OMe), 56.4 (C-12-OMe), 45.6 (C-α'), 44.8 (C-α), 44.1 (C-3), 44.2 (C-3), 42.5 (C-3'), 33.4 (C-3''), 32.8 (C-3'''), 28.2 (C-4), 27.2 (C-4').

HRMS-ESI (m/z) calculated for C$_{38}$H$_{38}$N$_4$NaO$_5$S [M+Na]$^+$: 717.2156; Found: 717.2156.

Example 31: Product 48

Step 1: Synthesis of N-(3-(diethylamino)propyl)-1H-imidazole-1-carboxamide

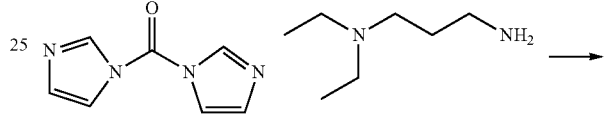

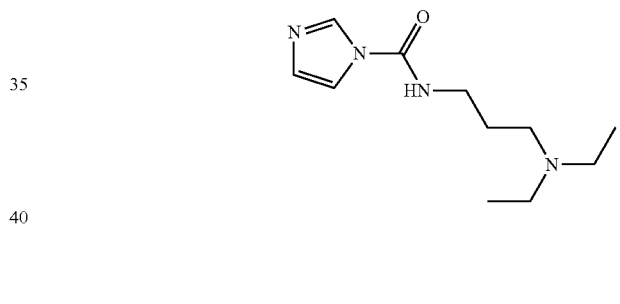

To a solution of 1,1-carbonyldimidazole (200 mg-1.23 mmol) in a mixture of DMF-MeCN (8 mL, (2:6)) was added 3-(diethylamino)propylamine (194 μL-1.23 mmol). The reaction mixture was stirred 2 hours at RT. The reaction mixture was concentrated under reduced pressure and the residue was purified by silica gel column with a linear gradient of dichloromethane-methanol (100:0 to 85:15), to give N-(3-(diethylamino)propyl)-1H-imidazole-1-carboxamide (60 mg, 0.267 mmol, 22%).

Step 2: Addition of N-(3-(diethylamino)propyl)-1H-imidazole-1-carboxamide to Nortrilobine 7

To a solution of nortrilobine 7 (6.3 mg-11.49 μmol) in 500 μL of dicholoromethane was added N-(3-(diethylamino)propyl)-1H-imidazole-1-carboxamide (10.32 mg-46.00 μmol) and triethylamine (6 μL-44.44 μmol). The mixture was stirred 24 hours at RT. The reaction mixture was concentrated under reduced pressure and the residue was purified by HPLC semi-preparative X-Terra RP-18, eluting with a linear gradient H$_2$O/MeCN with 0.02% triethylamine (80:20 to 0:100), to give 48 (3.1 mg, 3.60 μmol, 31%).

(48)

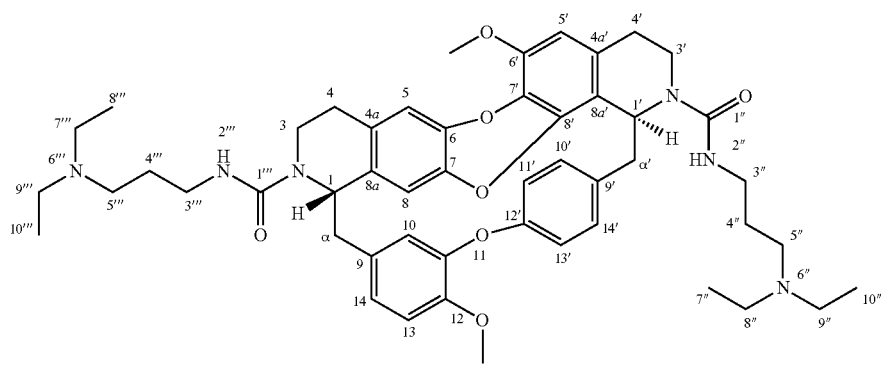

¹H NMR (500 MHz, CDCl₃) δ 8.16 (1H, br d, J=8.5 Hz, H-14'), 7.30 (1H, dd, J=8.4 Hz, J=2.7 Hz, H-13'), 7.16 (1H, br dd, J=8.2 Hz, J=1.9 Hz, H-10'), 7.05 (1H, dd, J=8.2 Hz, J=2.5 Hz, H-11'), 6.90 (1H, d, J=8.3 Hz, H-13), 6.79 (1H, dd, J=8.3 Hz, J=1.8 Hz, H-14), 6.62 (1H, d, J=2.0 Hz, H-10), 6.61 (1H, s, H-5), 6.32 (1H, s, H-5'), 6.11 (1H, s, H-8), 5.80 (1H, br, H-1'), 4.65 (1H, br, H-1), 4.26 (1H, br d, J=12.0 Hz, H-3), 4.01 (1H, m, H-3'), 3.98 (3H, s, 12-OMe), 3.85 (3H, s, 6'-OMe), 3.44 (4H, m, H-3", H-3'''), 3.33 (1H, br d, J=15.5 Hz, H-α), 3.19 (1H, m, H-3'), 3.06-2.92 (5H, m, H-3, H-4', H-α, H-α'), 2.89-2.76 (8H, m, H-7", H-7''', H-9", H-9'''), 2.73 (1H, m, H-4), 2.69-2.61 (5H, m, H-4', H-5", H-5'''), 2.51 (1H, br d, J=16.3 Hz, H-4), 1.92 (2H, m, H-4" or H-4'''), 1.73 (2H, m, H-4" or H-4'''), 1.16 (12H, m, H-8", H-8''', H-10", H-10''').

¹³C NMR (125 MHz, CDCl₃) δ 157.3 (C-1" or C-1'''), 157.2 (C-1" or C-1'''), 154.2 (C12'), 150.8 (C-11), 147.7 (C-12), 146.4 (C-6'), 139.9 (C-6 and C-7), 139.3 (C-8' or C-9'), 139.2 (C-8' or C-9'), 134.6 (C8a and C-9), 131.1 (C-10'), 130.2 (C-4a and C-14'), 129.8 (C-7'), 128.5 (C-4a'), 123.2 (C-13'), 121.8 (C-14), 121.5 (C-11'), 121.2 (C-8a'), 116.8 (C-10), 116.1 (C-5), 114.2 (C-8), 112.3 (C-13), 106.7 (C-5'), 58.4 (C-1), 56.6 (C-6'-OMe), 56.3 (C-12-OMe), 52.2 (C-1'), 50.0 (C-5" and C-5'''), 46.5 (C-α), 46.0 (C7" and C7''' and C-9" and C-9'''), 45.4 (C-α'), 39.2 (C-3' and C-3" and C-3'''), 38.1 (C-3), 28.2 (C-4), 27.4 (C-4'), 25.5 (C-4" or C-4'''), 24.8 (C-4" or C-4'''), 9.8 (C-8" or C-8''' or C-10" or C-10'''), 9.4 (C-8" or C-8''' or C-10" or C-10''').

HRMS-ESI (m/z) calculated for $C_{50}H_{65}N_6O_7$ [M+H]⁺: 861.4909; Found: 861.4892.

Example 32: Product 49

To a solution of trilobine 1 (10.5 mg-18.68 µmol) in 500 µL of dicholoromethane was added N-(3-(diethylamino)propyl)-1H-imidazole-1-carboxamide (8.4 mg-37.44 µmol) and 65 trimethylamine (5 µL-37.03 µmol). The mixture was stirred 24 hours at RT. The reaction mixture was concentrated under reduced pressure and the residue was purified by HPLC semi-preparative X-Terra RP-18, eluting with a linear gradient H₂O/MeCN with 0.1% formic acid (85:15 to 70:30), to give 49 (8 mg, 11.14 µmol, 59%).

(49)

¹H NMR (500 MHz, CDCl₃) δ 7.96 (1H, br d, J=7.4 Hz, H-14'), 7.19 (1H, br d, J=7.4 Hz, H-13'), 6.97 (2H, br m, H-10', H-14), 6.88 (2H, br m, H-11', H-13), 6.67 (1H, s, H-5), 6.60 (1H, br, H-10), 6.43 (1H, s, H-5'), 6.35 (1H, s, H-8), 5.67 (1H, br d, J=5.8 Hz, H-1'), 3.94 (3H, s, 12-OMe), 3.88 (3H, s, 6'-OMe), 3.69-3.59 (3H, m, H-1, H-3'), 3.49-3.40 (2H, m, H-3"), 3.28 (2H, m, H-3, H-α'), 3.11 (1H, br d, J=14.4 Hz, H-α), 3.04-2.97 (6H, m, H-5", H-7", H-9"), 2.94-2.83 (4H, m, H-4', H-α, H-α'), 2.74-2.66 (3H, m, H-3, H-4), 2.35 (3H, s, N2-Me), 2.01 (2H, m, H-4"), 1.25 (6H, t, J=7.0 Hz, H-8", H-10").

¹³C NMR (125 MHz, CDCl₃) δ 157.8 (C-1"), 154.4 (C12'), 149.8 (C-11), 147.7 (C-12), 146.5 (C-6'), 140.6 (C-6 or C-7), 139.7 (C-6 or C-7), 138.7 (C-8'), 137.6 (C-9'), 132.7 (C-9), 131.3 (C-14'), 131.0 (C-8a), 130.8 (C-4a), 130.6 (C-10'), 129.9 (C-4a'), 129.7 (C-7'), 123.1 (C-13'), 122.8 (C-14), 121.3 (C-11'), 120.3 (C-8a'), 117.4 (C-10), 115.8 (C-5), 114.8 (C-8), 112.5 (C-13), 106.8 (C-5'), 64.8 (C-1), 56.6 (C-6'-OMe), 56.3 (C-12-OMe), 51.4 (C-1'), 50.9 (C-3), 49.1 (C-5"), 49.2 (C-α'), 45.6 (C-7" and C-9"), 40.9 (C-3'), 39.5 (C—N2-Me), 38.1 (C-3"), 37.3 (C-α), 28.3 (C-4'), 26.3 (C-4), 24.6 (C-4"), 8.6 (C-8" and C-10").

HRMS-ESI (m/z) calculated for $C_{43}H_{51}N_4O_6$ [M+H]⁺: 719.3803; Found: 719.3794.

Example 33: Product 50

To a solution of O-methylcocsoline 3 (10.5 mg-18.68 µmol) in 500 µl of THF was added N-(3-(diethylamino)propyl)-1H-imidazole-1-carboxamide (2.5 µL-36.55 µmol) and triethylamine (5 µL-37.03 µmol). The mixture was stirred 24 hours at RT. The reaction mixture was concentrated under reduced pressure and the residue was purified by HPLC semi-preparative X-Terra RP-18, eluting with a linear gradient H₂O/MeCN with 0.02% triethylamine (85:15 to 70:30), to give 50 (12 mg, 16.71 µmol, 89%).

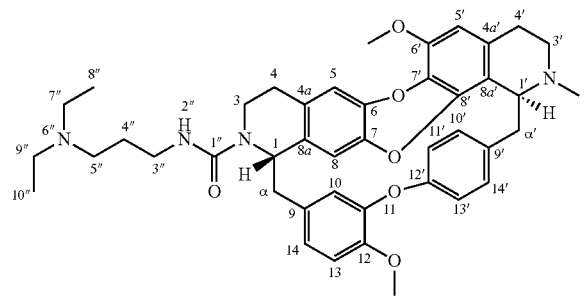

(50)

¹H NMR (500 MHz, CDCl₃) δ 7.66 (1H, br d, J=7.8 Hz, H-14'), 7.28 (1H, br, H-13'), 7.17 (1H, br d, J=7.9 Hz, H-10'), 7.11 (1H, br d, J=7.9 Hz, H-11'), 6.91 (1H, d, J=8.1 Hz, H-13), 6.78 (1H, br d, J=7.9 Hz, H-14), 6.67 (1H, br, H-10), 6.63 (1H, s, H-5), 6.33 (1H, s, H-5'), 6.12 (1H, s, H-8), 4.77 (1H, br, H-1), 4.26 (1H, br d, J=11.6 Hz, H-3), 4.09 (1H, br, H-1'), 3.98 (3H, s, 12-OMe), 3.87 (3H, s, 6'-OMe), 3.41 (1H, br d, J=15.3 Hz, H-α'), 3.29-3.18 (3H, m, H-3', H-3"), 3.08-2.94 (8H, m, H-3, H-3', H-4', H-7", H-9", H-α), 2.88 (2H, m, H-5"), 2.82-2.73 (3H, m, H-4, H-α, H-α'), 2.63 (3H, s, N2'-Me), 2.54 (2H, m, H-4, H-4'), 1.87 (2H, m, H-4"), 1.24 (6H, t, J=7.1 Hz, H-8", H-10").

¹³C NMR (125 MHz, CDCl₃) δ 157.2 (C-1"), 154.4 (C12'), 150.5 (C-11), 147.8 (C-12), 146.5 (C-6'), 140.0 (C-6 or C-7 or C-8' or C-9'), 139.8 (C-6 or C-7 or C-8' or C-9'), 139.7 (C-6 or C-7 or C-8' or C-9'), 134.6 (C-8a and C-9), 131.5 (C-10'), 130.2 (C-4a), 129.8 (C-7'), 128.4 (C-14'), 127.3 (C-4a'), 122.8 (C-13'), 122.0 (C-14), 121.8 (C-11'), 119.5 (C-8a'), 116.9 (C-10), 116.2 (C-5), 114.1 (C-8), 112.5 (C-13), 106.6 (C-5'), 61.0 (C-1'), 58.0 (C-1), 56.5 (C-6'-OMe), 56.4 (C-12-OMe), 48.9 (C-5"), 46.5 (C-α), 45.6 (C-7" and C-9"), 45.2 (C-3'), 42.1 (C-α'), 41.5 (C—N2'-Me), 38.2 (C-3 or C-3"), 38.1 (C-3 or C-3"), 28.2 (C-4), 24.7 (C-4"), 23.3 (C-4'), 8.5 (C-8" and C-10").

HRMS-ESI (m/z) calculated for $C_{43}H_{51}N_4O_6$ [M+H]⁺: 719.3803; Found: 719.37940.

Example 34: Product 51

Step 1: Treatment of Product 44 with Hydrogen Peroxide

To an ice-cooled mixture of product 44 (8.6 mg-13.89 µmol) in H₂O/1,4-dioxane (1:2, 450 µL) and sodium tungstate (2.5 mg-7.58 µmol) was added drop-wise hydrogen peroxide (18 µL-332.3 µmol). The reaction was stirred 1.5 hours at RT. Then manganese dioxide was added until a black precipitate. The reaction mixture was concentrated under reduced pressure and the residue was purified by silica gel column with an isocratic dichloromethane-methanol 1% NH₃ (70:30).

Step 2: Treatment with Iron Sulphate Heptahydrate:

To an ice-cooled solution of product of step 1 (6.8 mg-10.71 µmol) in 400 µl of methanol was added iron sulphate heptahydrate (13 mg-46.76 µmol). The reaction was stirred 24 hours at RT. Then, the reaction mixture was concentrated under reduced pressure. The residue was dissolved with EDTA (10 mL-0.1M) and adjusted at pH=10 with ammoniac. The solution was extracted by a liquid/liquid extraction with dichloromethane. The organic phase was dried with sulfate magnesium and concentrated under reduced pressure. The residue was purified by HPLC semi-preparative X-Terra RP-18, eluting with a linear gradient H₂O/MeCN with 0.02% triethylamine (60:40 to 30:70), to give 51 (1.2 mg, 1.98 µmol, 14%).

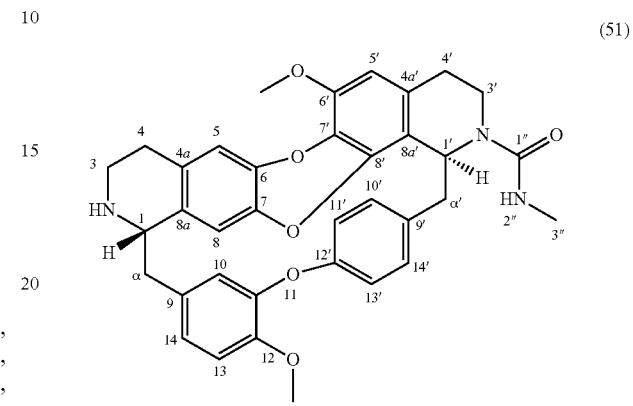

(51)

¹H NMR (500 MHz, MeOD) δ 7.83 (1H, dd, J=8.6 Hz, J=2.0 Hz, H-14'), 7.05 (1H, br dd, J=8.3 Hz, J=2.3 Hz, H-13'), 7.01 (1H, br d, J=8.5 Hz, H-13), 6.97 (1H, br, H-14), 6.93 (1H, br, H-10'), 6.80 (1H, br, H-11'), 6.70 (1H, br, H-10), 6.63 (2H, br s, H-5, H-5'), 6.32 (1H, br s, H-8), 5.57 (1H, br d, J=8.6 Hz, H-1'), 3.91 (3H, s, 12-OMe), 3.86 (3H, s, 6'-OMe), 3.66 (1H, m, H-3'), 3.48 (1H, br, H-1), 3.38 (1H, m, H-3'), 3.22 (1H, br d, J=13.3 Hz, H-α'), 3.07-2.83 (6H, m, H-3, H-4 or H-4', H-α, H-α'), 2.81 (3H, br, NH-3"Me), 2.76 (2H, m, H-4 or H4', H-α), 2.64 (1H, m, H-4 or H-4').

¹³C NMR (125 MHz, MeOD) δ 160.5 (C-1"), 157.5 (C12'), 151.1 (C-11), 149.7 (C-12), 148.3 (C-6'), 141.4 (C-6 or C-7 or C-8'), 140.4 (C-6 or C-7 or C-8'), 139.8 (C-6 or C-7 or C-8'), 138.3 (C-9'), 137.0 (C-8a), 135.4 (C-9), 134.0 (C-4a), 132.5 (C-14'), 131.6 (C-10'), 131.5 (C-4a'), 131.2 (C-7'), 124.4 (C-14), 123.1 (C-13'), 121.6 (C-11'), 120.9 (C-8a'), 119.8 (C-10), 116.8 (C-5), 114.5 (C-8), 114.0 (C-13), 108.3 (C-5'), 60.2 (C-1), 57.0 (C-6'-OMe and C-12-OMe), 52.9 (C-1'), 47.3 (C-α'), 43.6 (C-3), 42.2 (C-3'), 41.1 (C-α), 29.0 (C-4 or C-4'), 28.9 (C-4 or C-4'), 28.0 (C-3").

HRMS-ESI (m/z) calculated for $C_{36}H_{36}N_3O_6$ [M+H]⁺: 606.2599; Found: 606.2602.

Example 35: Product 53

To a solution of 2'-norcocsuline 5 (6 mg-10.95 µmol) in 250 µL of dicholoromethane was added N-methylcarbamoylimidazole (5.5 mg-44 µmol) and triethylamine (2 µL-14.84 µmol). The mixture was stirred 16 hours at RT. The reaction mixture was concentrated under reduced pressure and the residue was purified by HPLC semi-preparative X-Terra RP-18, eluting with a linear gradient H₂O/MeCN with 0.02% triethylamine (70:30 to 35:65), to give 53 (2.1 mg, 3.47 µmol, 32%).

(53)

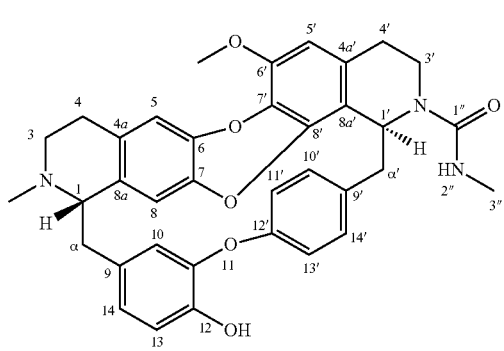

¹H NMR (500 MHz, DMSO-d$_6$) δ 7.99 (1H, dd, J=8.5 Hz, J=1.8 Hz, H-14'), 7.12 (2H, m, H-10', H-13'), 6.99 (1H, dd, J=8.2 Hz, J=2.6 Hz, H-11'), 6.79 (1H, d, J=8.0 Hz, H-13), 6.74 (1H, dd, J=8.2 Hz, J=1.9 Hz, H-14), 6.65 (1H, s, H-5), 6.60 (1H, s, H-5'), 6.54 (1H, q, J=4.2 Hz, 2"-NH), 6.42 (1H, d, J=1.9 Hz, H-10), 6.07 (1H, s, H-8), 5.64 (1H, m, H-1'), 3.79 (3H, s, 6'-OMe), 3.72 (1H, m, H-3'), 3.41 (1H, m, H-3'), 3.18 (1H, br, H-α'), 3.07 (1H, br t, J=3.4 Hz, H-1), 2.85-2.65 (7H, m, H-3, H-4, H-4', H-α, H-α'), 2.64 (3H, d, J=4.4 Hz, NH-3"Me) 2.55 (1H, m, H-4), 2.46 (1H, m, H-3), 2.24 (3H, s, N2-Me).

¹³C NMR (125 MHz, DMSO-d$_6$) δ 157.2 (C-1"), 154.1 (C12'), 148.7 (C-11), 145.8 (C-6'), 144.8 (C-12), 138.8 (C-6 or C-7), 138.7 (C-6 or C-7), 138.2 (C-9'), 138.0 (C-8'), 135.5 (C-8a), 132.9 (C-9), 130.6 (C-4a), 130.5 (C-10'), 130.1 (C-14'), 129.0 (C-4a'), 128.7 (C-7'), 122.2 (C-13' or C-14), 122.1 (C-13' or C-14), 121.2 (C-11'), 120.2 (C-8a'), 116.9 (C-10), 116.5 (C-13), 115.4 (C-5), 113.5 (C-8), 107.2 (C-5'), 67.2 (C-1), 55.9 (C-6'-OMe), 50.7 (C-1'), 50.1 (C-3), 45.1 (C-α'), 42.3 (C—N2-Me), 40.3 (C-α), 38.9 (C-3'), 27.3 (C-3"), 27.2 (C-4), 26.7 (C-4').

HRMS-ESI (m/z) calculated for $C_{36}H_{36}N_3O_6$ [M+H]⁺: 606.2599; Found: 606.2596.

Example 36: Product 54

To an ice-cooled (−50° C.) mixture of cocsuline 4 (6 mg-10.68 μmol) in 600 μL of dichloromethane (600 μL) and triethylamine (2 μL-14.84 μmol) was added trifluoromethanesulfonic anhydride (2 μL-12.2 μmol). The mixture was stirred 2 hours at −50° C. and then 16 hours at RT. The reaction mixture was concentrated under reduced pressure and the residue was purified by HPLC semi-preparative X-Terra RP-18, eluting with a linear gradient H₂O/MeCN with 0.02% triethylamine (80:20 to 0:100), to give 54 (4.9 mg, 7.06 μmol, 66%).

(54)

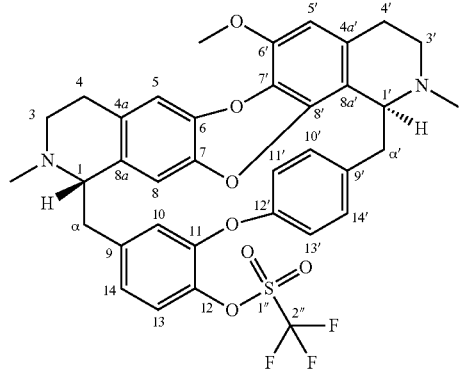

¹H NMR (500 MHz, CDCl$_3$) δ 7.63 (1H, dd, J=8.4 Hz, J=2.1, H-14'), 7.23 (1H, dd, J=8.5 Hz, J=2.6 Hz, H-13'), 7.21 (2H, m, H-10', H-13), 7.00 (1H, dd, J=8.4 Hz, J=2.7 Hz, H-11'), 6.93 (1H, dd, J=8.3 Hz, J=1.9 Hz, H-14), 6.73 (1H, d, J=1.9 Hz, H-10), 6.63 (1H, s, H-5), 6.33 (1H, s, H-5'), 6.03 (1H, s, H-8), 4.02 (1H, br t, J=3.2 Hz, H-1'), 3.87 (3H, s, 6'-OMe), 3.36 (1H, br dd, J=15.4 Hz, J=2.5 Hz, H-α'), 3.23 (1H, br t, J=3.1 Hz, H-1), 3.17 (1H, m, H-3'), 3.00-2.81 (5H, m, H-3, H-3', H-4', H-α), 2.76-2.69 (2H, m, H-4, H-α'), 2.64-2.61 (2H, m, H-3, H-4), 2.60 (3H, s, N2'-Me), 2.52 (1H, m, H-4'), 2.39 (3H, s, N2-Me).

¹³C NMR (125 MHz, CDCl$_3$) δ 153.3 (C12'), 152.5 (C-11), 146.3 (C-6'), 144.3 (C-12), 141.1 (C-9'), 140.0 (C-6 or C-7 or C-8'), 139.7 (C-6 or C-7 or C-8'), 139.5 (C-6 or C-7 or C-8'), 136.9 (C-9), 134.9 (C-8a), 131.6 (C-10'), 130.2 (C-4a), 129.7 (C-7'), 128.9 (C-14'), 127.8 (C-4a'), 123.0 (C-13), 122.5 (C-13'), 122.4 (C-14), 121.5 (C-11'), 120.6 (C-8a'), 119.0 (d, J=2.6 Hz, C-2"), 118.8 (C-10), 116.1 (C-5), 113.9 (C-8), 106.8 (C-5'), 67.3 (C-1), 60.6 (C-1'), 56.5 (C-6'-OMe), 50.3 (C-3), 45.3 (C-3'), 42.8 (C—N2-Me), 42.3 (C-α'), 42.1 (C—N2'-Me), 41.9 (C-α), 27.6 (C-4), 23.7 (C-4').

HRMS-ESI (m/z) calculated for $C_{36}H_{34}F_3N_2O_7S$ [M+H]⁺: 695.2033; Found: 695.2117.

Example II. Biological Tests of the Compounds According to the Invention

II. 1 hDNMT3A Assay hDNMT3A enzyme inhibition was adapted from the restriction-based fluorescence assay protocol as described in the literature (Ceccaldi et al. Chem Bio Chem 2011, 12, 1337-1345). Briefly, a 5'-labelled biotin oligonucleotide is hybridized to its complementary strand labelled with 6-carboxyfluorescein at the 3'-end into a 384 well microplate (black Optiplates; Perkin Elmer) pre-coated with avidin. The duplex contains a unique CpG site overlapping with a restriction site of a methylation sensitive restriction enzyme. The human C-terminal DNMT3A (623-908a.a.), produced as described in (Gros et al. Nucl. Acids Res. 2013, 41(19): e185), was added in each well (200 ng/well) and mixed with the chemical compounds at desired concentrations and freshly prepared SAM (20 μM final concentration) to start the reaction in a total volume of 50 μL. After 1 hour incubation at 37° C. each well were washed three times with PBS, Tween-20 0.05%, NaCl (500 mM) and three more times with PBST. Specific fluorescent signals were detected with the methylation-sensitive restriction enzyme HpyCH4IV (NEB) as described and measured on a Perkin Elmer Envision detector. The percentage of inhibition is reported. The formula used to calculate the percentage of inhibition is [(X−Y)/X]×100, where X is the signal determined in the absence of the inhibitor and Y is the signal obtained in the presence of the inhibitor. The concentration at which 50% of efficacy of inhibition is observed (EC50) was determined by analysis of a concentration range of the tested compound in triplicates. The non-linear regression fittings with sigmoidal dose-response (variable slope) were performed with GraphPad Prism 4.03 (GraphPad Software).

Compounds of the invention inhibit human DNMT3A enzyme as reported in the table 1.

TABLE 1

Percentage of inhibition of catalytic human DNMT3A by the compounds at 32 and 10 µM and concentration in µM at which 50% of efficacy of inhibition is observed (EC50).

| | hDNMT 3A inhibition | | |
|---|---|---|---|
| | | Inhibition (%) | |
| N° | EC50 (µM) | 32 µM | 10 µM |
| Trilobine (1) | 3.80 | 96 | 88 |
| | 3.21 to 4.49 | | |
| (10) | n.d. | 72 | 17 |
| (11) | n.d. | 77 | 43 |
| (12) | 2.67 to 3.80 | 93 | 78 |
| (13) | n.d. | 45 | 39 |
| (14) | 1.91 | 96 | 93 |
| | 1.15 to 3.18 | | |
| (15) | n.d. | 50 | 46 |
| (16) | n.d. | 77 | 56 |
| (17) | n.d. | 79 | 69 |
| (18) | n.d. | 66 | 66 |
| (19) | n.d. | 71 | 67 |
| (20) | n.d. | 66 | 50 |
| (21) | n.d. | 82 | 32 |
| (22) | n.d. | 64 | 60 |
| (24) | n.d. | 77 | 42 |
| (25) | n.d. | 72 | 46 |
| (27) | n.d. | 67 | 21 |
| (28) | n.d. | 60 | 18 |
| (30) | 4.19 to 9.36 | 88 | 66 |
| (31) | n.d. | 79 | 43 |
| (32) | 5.34 to 6.87 | 82 | 57 |
| (33) | n.d. | 87 | 32 |
| (41) | 0.557 to 0.910 | 95 | 94 |
| (42) | 0.64 | 98 | 98 |
| | 0.47 to 0.86 | | |
| (43) | n.d. | 49 | 24 |
| (44) | 3.96 | 96 | 82 |
| | 3.04 to 5.17 | | |
| (45) | n.d. | 73 | 31 |
| (46) | n.d. | 52 | 7 |
| (47) | n.d. | 40 | 10 |
| (48) | 1.93 | 98 | 82 |
| | 1.00 to 3.72 | | |
| (49) | 6.10 | 75 | 60 |
| | 3.72 to 10.0 | | |
| (50) | 2.06 | 91 | 69 |
| | 1.28 to 3.31 | | |
| (51) | n.d. | 69 | 2 |
| (54) | n.d. | 32 | 0 |

II.2 hDNMT1 Assay.

His-DNMT1 (182 kDa, human) was cloned, expressed and purified as described (Halby et al. *Chem Bio Chem* 2012, 13, 157-165). The reaction was performed in a 10 µL total reaction volume in low volume NBS™ 384-well microplates (Corning), containing the tested compound (up to 1% DMSO), 1 µM of a SAM/[methyl-$^3$H] SAM (3TBq/mmol, PerkinElmer) mix in a ratio of 3-to-1 (isotopic dilution 1*:3), 0.3 µM of biotinylated hemimethylated DNA duplex (5'-GATmCGCmCGATGmCGmCGAATmCGmC-GATmCGATGmCGAT-3' and BIOT-5'-ATCGCATC-GATCGCGATTCGCGCATCGGCGATC-3'), and 90 nM of DNMT1 in methylation buffer (20 mM HEPES pH 7.2, 1 mM EDTA, 50 mM KCl, 25 µg/mL BSA). The reaction was incubated at 37° C. for 2 hours. 8 µL are then transferred into a streptavidin 96-well scintillant coated Flashplate™ (PerkinElmer) containing 190 µL of 20 µM SAH in 50 mM Tris-HCl pH 7.4. The Flashplate™ was agitated at room temperature for 1 hour and read in 200 µL of 50 mM Tris-HCl pH 7.4 on TopCount NXT (PerkinElmer). The percentage of inhibition is reported. The formula used to calculate the percentage of inhibition is [(X−Y)/X]×100, where X is the signal determined in the absence of the inhibitor and Y is the signal obtained in the presence of the inhibitor.

Compounds of the invention inhibit human DNMT1 enzyme as reported in the table 2.

TABLE 2

Table 1. Percentage of inhibition of full-length human DNMT3 by the compounds at 32 and 10 µM and concentration in µM at which 50% of efficacy of inhibition is observed (EC50).

| | hDNMT 1 inhibition | | |
|---|---|---|---|
| | EC50 | Inhibition (%) | |
| N° | (µM) | 32 µM | 10 µM |
| Trilobine (1) | n.d.* | 50% | 4% |
| (41) | 11.0 ± 0.7 | 99% | 60% |
| (42) | 10.6 ± 2.8 | 100% | 38% |
| (44) | n.d.* | 15% | 0% |
| (48) | 14.6 ± 1.3 | 98% | 32% |

*n.d.: not determined

Since the compounds are inhibitors of DNMTs, their ability to induce the luciferase expression under the control of a methylated CMV promoter was evaluated.

II.3 CMV-luc Reexpression

KG-1 cells were stably transfected with the firefly luciferase reporter gene (luc+ from pGL3; Promega) under the control of the cytomegalovirus (CMV) promoter (from pEGFP-N1; Clontech Laboratories Inc.) partially methylated (50%). 20,000 cells per well were seeded in a 96-well plate. After 24 h incubation in the presence of the test compound or solvant (DMSO), the induction of the promoter was measured by quantification of the luciferase signal with the Brite-lite assay system (PerkinElmer) according to the manufacturer's protocol. The luminescence was measured on an EnVision multilabel plate reader (PerkinElmer), and the data are expressed as the fold induction as compared with the DMSO control. The mean of three experiments and the standard error is reported.

Compounds of the invention induced expression of the luciferase gene under the control of the methylated CMV promoter (table 3).

TABLE 3

Induction fold in the luciferase expression induced by the compounds compared to cells treated with DMSO.

| | Induction Fold (IF) of luciferase gene reporter in KG-1 CMV-Luc Concentration (µM) | | | | | |
|---|---|---|---|---|---|---|
| No | 10 | 5 | 3.2 | 1 | 0.32 | 0.1 |
| Trilobine (1) | too cytotoxic | 6.4 ± 0.1 | 3.5 ± 1.1 | 2.6 ± 1.4 | 1.9 ± 1.2 | 1.1 ± 0.1 |

TABLE 3-continued

Induction fold in the luciferase expression induced by the compounds compared to cells treated with DMSO.

Induction Fold (IF) of luciferase gene reporter in KG-1 CMV-Luc Concentration (μM)

| No | 10 | 5 | 3.2 | 1 | 0.32 | 0.1 |
|---|---|---|---|---|---|---|
| (41) | 3.1 ± 0.4 | 2.8 ± 0.2 | 2.0 ± 0.3 | 1.3 ± 0.1 | 1.1 ± 0.1 | 1.1 ± 0.1 |
| (42) | too cytotoxic | 2.3 ± 0.1 | 2.0 ± 0.2 | 1.5 ± 0.1 | 1.3 ± 0.1 | 1.2 ± 0.1 |
| (44) | 9.0 ± 1.3 | 2.5 ± 0.9 | 2.0 ± 0.1 | 1.3 ± 0.1 | 1.1 ± 0.1 | 1.1 ± 0.1 |
| (48) | 2.3 ± 1.3 | 1.3 ± 0.1 | 1.2 ± 0.1 | 1.2 ± 0.1 | 1.2 ± 0.3 | 1.1 ± 0.1 |

Their ability to demethylate the CMV promoter in the cancer cells and to open the chromatin on such promoter was also measured.

II.4 CMV Promoter Analysis

Using the Nucleosome Occupancy and Methylome Sequencing (NOMe-Seq) technique, the methylation status of the CMV promoter and the position of the nucleosomes on such promoter were both analysed.

NOMe-seq is a modified version of the methylation-dependent single promoter assay described by Miranda et al. (*Curr Protoc Mol Biol.* 2010 21.17.1-16) and the methylase-based DNA assay was performed as previously described with minor modifications. After nuclei extraction, GpC DNA methyltransferase M.CviPI (New England Biolabs) reactions were done in M.CviPI reaction buffer. GpC methyltransferase treatment was followed by DNA extraction, sodium bisulfite conversion, PCR amplification of the region of interest, cloning, and sequencing of individual clones to reveal the structure of single replicas as functional units. After treatment with the compounds or with DMSO, KG-1-Luc cells were centrifuged for 5 min at 500×g. Cell pellets were washed in ice-cold PBS, resuspended in 1 mL of ice-cold nuclei buffer [10 mM Tris (pH 7.4), 10 mM NaCl, 3 mM $MgCl_2$, 0.1 mM EDTA, and 0.5% Nonidet P-40, plus protease inhibitors] per $2 \times 10^6$ cells, and incubated on ice for 10 min. Nuclei were recovered by centrifugation at 900×g for 5 min, washed twice in nuclei wash buffer [10 mM Tris (pH 7.4), 10 mM NaCl, mM $MgCl_2$, and 0.1 mM EDTA containing protease inhibitors], and resuspended with 200 μL in 1×M.CviPI reaction buffer supplemented with 0.3 M sucrose, 160 μM SAM (New England Biolabs). 100 μL of purified genomic DNA were treated with 100 U of M.CviPI for 15 min at 37° C. in 200 μL final volume. The other part of 100 μL of purified genomic DNA were not treated with 100 U of M.CviPI but just incubated for 15 min at 37° C. to obtain CpG methylation profile. Reactions were stopped by the addition of an equal volume of stop solution [20 mM Tris.HCl (pH 7.9), 600 mM NaCl, 1% SDS, 10 mM EDTA, and 400 μg/mL Proteinase K] and incubated at 55° C. overnight. DNA was purified by phenol/chloroform extraction and ethanol precipitation. Bisulfite conversion was performed with the EZ DNA Methylation-Gold Kit (Zymo Research). Bisulfited DNA was eluted with 12 μL of water and 8 μL were used for CMV amplification.

PCR Amplification of Bisulfite-Treated DNA

The CMV promoter DNA amplification was carried on 8.3 μL eluted bisulfited DNA in 20 μL PCR reaction containing 1×KAPA2G Buffer A, 2.0 mM $MgCl_2$, 200 μM dNTPs, 125 nM each primer and 1.0 units KAPA2G™ Robust HotStart DNA Polymerase (KapaBiosystems) on C1000 Touch™ thermal cycler 95° C. 3 min following by 95° C. for 20 sec, 55° C. for 30 sec, 72° C. for 30 sec×40 cycles and final extension at 72° C. 1 min. PCR fragments were quality controlled by agarose gel electrophoresis. Oligonucleotides used are listed in table below.

Steps of cloning and sequencing were as those described previously except that M13 PCR was used to amplify the cloned sequence in 20 μL PCR reaction volume containing 1×KAPA2G Buffer B, 2.0 mM $MgCl_2$, 200 μM dNTPs, 125 nM each primer and 1.0 U KAPA2G™ Robust HotStart DNA Polymerase (KapaBiosystems) on C1000 Touch™ thermal cycler 95° C. 3 min following by 95° C. for 20 sec, 55° C. for 30 sec, 72° C. for 30 sec×40 cycles and final extension at 72° C. 1 min.

TABLE 4

Oligonucleotides used in this study

| Targets | Sequences | Analysis |
|---|---|---|
| CMV | F: GGGGTTATTAGTTTATAGTTTATATATGGA<br>R: AATACCAAAACAAACTCCCATTAAC | NOMeSeq |
| M13 forward | 5' TGTAAAACGACGGCCAGT 3' | NOMeSeq |
| P16 CDKN2A | F: GGTTTTTTTAGAGGATTTGAGGGATAGG<br>R: CTACCTAATTCCAATTCCCCTACAAACTTC | COBRA |
| P15 CDKN2B | F: TGAGATGGTAGAATAAAAATTATTAAAAA<br>R: AAACAAAAACATACCCAATAAAAAC | Bisulfite PCR Cloning-Sequencing |

Sequence Alignment and Analysis of CG and GC Methylation Levels

Genomic alignment and bisulfite sequence analysis was performed largely as previously described (Berman et al. Nat Genet 2012, 44, 40-6).

BISMA (Bisulfite Sequencing DNA Methylation Analysis) software was used for CpG methylation analysis of primary bisulfite sequencing data from subcloned individual molecules (Rohde et al. *BMC Bioinformatics* 2010, 11, 230). Methyl Viewer (Pardo et al. *Nucleic Acids Res* 2011, 39, e5) was used to obtain GC methylation results and nucleosome occupancy. The ratio of methylation is representative of the chromatin accessibility by M.CviPI and nucleosome occupancy. The combined methylation status for each clone by CpG (BISMA) or GpC (Methyl Viewer) site has been assembled. The methylation status of cytosines in CpG and GpC contexts at a given position within the sequence, given as ratio of methylation, can be calculated as follows: R=[MCT/MCNT], where MCT is the percentage of Methylated Cytosines analysed DNA sequence in the Treated sample, and MCNT is the percentage of Methylated Cytosines on the same DNA sequence in a Not Treated sample. The chromatin accessibility is represented in the table 5 as ration of GpC methylation. The DNA demethylation is reported as percentage of methylated cytosine in the treated sample compared the non treated sample (Table 5).

C5 DNA Methylation Analysis at Endogenous Promoters

Cancer cell lines (colon HCT116 or leukaemia KG1) were treated with the compounds as indicated in the Data Tables and then analysed as following.

DNA Extraction and Bisulphite Treatment

DNA was isolated from cultured cells using the DNeasy Blood and Tissue Kit according to the manufacturer's specifications (Qiagen). DNA bisulphite conversion was performed on 2 µg of DNA using the EZ DNA Methylation-Gold Kit according to the manufacturer's specifications (Zymo Research) and bisulfited DNA was eluted with 10 µL of water.

Two different techniques were used to analyse the DNA methylation profile after bisulfite conversion of genomic DNA: (A) cloning and sequencing or (B) COBRA. The primers for each promoter are specified in Table 4.

A/ Cloning and Sequencing

Sequencing of bisulfite-treated DNA allowing resolution of the methylation state of every cytosine in the target sequence, at single molecule resolution, is considered as the "gold standard" for DNA methylation analysis.

CDKN2B (P15) and P73 Promoter PCR Amplification of Bisulfite-Treated DNA

Bisulfite-specific primers with a minimum length of 18 bp were designed using Primer 3 program. The target sequence of the designed primers contained no CpGs allowing amplification of both un- and hypermethylated DNAs. All primers were tested for their ability to yield high quality sequences and primers that gave rise to an amplicon of the expected size using non-bisulfite treated DNA as a template were discarded, thus ensuring the specificity for bisulfite-converted DNAs. Primers used in this study are listed in the table above. The targeted DNA amplification was set up with 2.5 µL eluted bisulfited DNA in 50 µL PCR reaction volume containing 1×PCR buffer, 1.5 mM MgCl$_2$, 200 µM dNTPs, 200 nM each primer and 1.0 units Platinum® Taq DNA Polymerase (Invitrogen) on C1000 Touch™ thermal cycler 94° C. 2 min following by 94° C. for 30 sec, 55° C. for 30 sec, 72° C. for 1 min×35 cycles and final extension at 72° C. 6 min. PCR fragments were quality controlled by agarose gel electrophoresis.

Cloning and Sequencing

PCR amplicons were cloned with the StrataClone Ultra Blunt PCR Cloning Kit (Agilent Technologies), according to the manufacturers' instructions and up to 24 clones were picked for sequencing. First, M13 PCR was performed to amplify cloned sequence: each colony was resuspended in 50 µL water and 1 µL of each bacterial suspension was used to a 20 µL PCR reaction volume containing 1×PCR buffer, 2.5 mM MgCl$_2$, 2 mM dNTPs, 3.2 µM each primer that anneals to sites flanking the insertion/ligation plasmid site, and 1.25 units AmpliTaq Gold DNA polymerase (Applied Biosystems) on C1000 Touch™ thermal cycler 95° C. 10 min following by 95° C. for 45 sec, 55° C. for 45 sec, 72° C. for 1 min×35 cycles and final extension at 72° C. 10 min. PCR amplicons were cleaned up using Bio-Gel-P100 (Bio-Rad Laboratories) to remove any excess nucleotides and primers. Final sequencing was performed using a M13 primer on ABI 3100 capillary sequencers using 1/8 dilution of ABI Prism BigDye terminator V3.1 sequencing chemistry after hotstart 96° C. for 60 sec and thermocycling 96° C. for 10 sec, 50° C. for 10 sec, 60° C. for 4 min×25 cycles. Sequencing reactions were cleaned up using Sephadex® G-50 (GE Healthcare) to remove any excess nucleotides and dyes. Electrophoregram files and methylation signals at a given CpG site were quantified using the BISMA software as described above.

B/ Combined Bisulfite Restriction Analysis (COBRA)

This technique is a variation of bisulfite sequencing and combines bisulfite conversion based polymerase chain reaction with restriction digestion. DNA methylation levels are easily and quickly measured at fewer CpG sites than bisulfite-cloning-sequencing.

CDKN2A (P16) Promoter PCR Amplification of Bisulfite-Treated DNA

DNA amplification was set up with 100 ng eluted bisulfited DNA in 50 µL PCR reaction containing 1×PCR buffer, 2.5 mM MgCl$_2$, 0.3 mM dNTPs, 400 nM each primer and 1.25 units EpiTaq HS (Takara) on C1000 Touch™ thermal cycler by 98° C. for 10 sec, 55° C. for 30 sec, 72° C. for 30 sec×40 cycles. 20 µL of PCR amplicons were digested in 30 µL by 2 units of BsiEI at 60° C. for 90 min. DNA fragments were migrated by 2% agarose gel electrophoresis and each band was quantified by Image Lab Software v2.0 (BioRad Laboratories).

Compounds of the invention are able to demethylate the promoter of several tumor suppressor genes in several cancer cells (data reported in the table here below) and to demethyate the CMV promoter, open the chromatin on such promoter and reactivate the luciferase signal (as reported in table 5).

TABLE 5 activity of the compounds on the CMV promoter and P15 promoter in leukaemia KG1 cells and on P16 promoter in colon cancer cells HTC116,

| | KG1 CMV-Luc model (24 h) at 5 µM | | | Demethylation (COBRA) | |
|---|---|---|---|---|---|
| | IF-24 h | DNA demethylation | Chromatin accessibility | P16 or P73*/HCT116 | P15/KG1 |
| Trilobine (1) | 5.8 ± 0.6 | −37 ± 8% | 1.9 ± 0.1 | −37% after 3 days (at 0.1 µM) −52% after 7 days (at 0.1 µM) −53% after 21 days (at 0.1 µM) | −25% after 3 days (at 0.32 µM) |
| (41) | 3.3 ± 0.1 | 0% | 2.1 ± 0.1 | 0% after 7 days (at 0.1 µM) *−24% after 7 days (at 0.32 µM) | n.d. |
| (42) | 1.1 ± 0.6 | n.d. | n.d. | n.d. | n.d. |
| (44) | 5.9 ± 0.2 | −53 ± 6% | 2.3 ± 0.2 | 0% after 7 days (at 0.1 µM) *−17% after 7 days (at 0.32 µM) | n.d. |
| (48) | 1.1 | n.d. | n.d. | ND | n.d. | n.d. = not determined

In addition the compounds were able to demethylate tumour suppressor genes promoters in cancer cells such as P16 in colon cancer cell line HCT116 and P15 in leukemia KG1.

II.5 Anti-Proliferative Activity

Human cancer cells were obtained from the ATCC (USA) and cultivated in medium suggested by the supplier supplemented with foetal calf serum (Lonza, France), at 37° C. and under 5% $CO_2$. To measure the anti-proliferative properties of tested molecules, $2 \times 10^4$ cells are seeded at day 0 in a 96 wells plate. The compounds to be tested, stored at −20° C. as $10^{-2}$ M stock solution in 100% DMSO, are freshly diluted on day 1 in the cell medium, before adding a dose range of 3.2 nM to 10 µM to the cells. Cells are treated everyday and cell viability assessed after 3 days or 7 days of treatment. The cell viability is assessed using the ATPLite kit from Perkin (ATPlite 1 Step Luminescence Assay System, ref 3016739), following the provider instructions. The raw data are analyzed with GraphPad Prism software (v4.03) to generate IC50 values corresponding to the compound concentrations giving 50% reduction in cell viability. The values presented are the mean results of at least two independent experiments. The standard errors are indicated.

Compounds of the invention present a potential anti-cancer activity on a panel of cancer cell lines (table 6).

TABLE 6

| | Antiproliferative activity: IC50 (µM)* | | |
|---|---|---|---|
| | HCT116 (colorectal cancer) | KG-1 (leukemia) | WM266-4 (melanoma)* |
| Trilobine (1) | 1.19 ± 0.02 | 2.1 ± 0.8 | 3.2 ± 0.8 |
| (41) | 0.96 ± 0.02 | 5.3 ± 0.4 | 4.4 ± 1.5 |
| (42) | 0.50 ± 0.01 | 3.57 ± 0.04 | n.d. |
| (44) | 1.88 ± 0.03 | 4.20 ± 0.05 | 12 ± 3 |

*two treatments instead of three.
n.d. = not determined

To further test the effect of compounds on DNA methylation and gene reexpression we analysed its effect on the invasiveness capacity of metastatic melanoma WM266 cell line in a 3D model.

II.6 Spheroid Formation and Invasion Assay

After treatment with compound 1 or 42 at concentrations at which the compound is not cytotoxic, metastatic melanoma cells WM-266-4 GFP (3000 cells/condition) were allowed to form spheroids for 2 days on agarose 1% (Sigma-Aldrich, #A95-39) coated in 96-well plates, leading to ~300 µm diameter spheroids. Then six different spheroids for each condition were individually embedded in EMEM media (Lonza, #BE12-684F) containing 1% of Bovin Collagen I (BD, #354231) and 2% SVF. The initial spheroid size and the 24 h invasion area were measured by fluorescent microscopy, using an Axiovert 200M device (5× Plan-Neofluor objective, Carl Zeiss, Germany). Fluorescent invasion areas were quantified using Image J (NIH) software on the sum of six Z-stacks images (20 µm interval) for each spheroid. Invasion Index was obtained by normalising the invasion area at 24 h by the initial spheroid area. Six individual spheroids were quantified for each condition and three independent experiments were performed. The results are illustrated in annexed FIG. 1.

Compounds of the invention decreased the invasion index in metastatic melanoma cells.

In conclusion, the compounds inhibit DNA methylation, in vitro and in cancer cells. By their action, the compounds are able to reprogram the cancer cells towards less aggressive state and could be used to sensitize towards immunotherapies and chemotherapies.

The invention claimed is:
1. A compound of the following formula (I) or a pharmaceutically acceptable salt or solvate thereof:

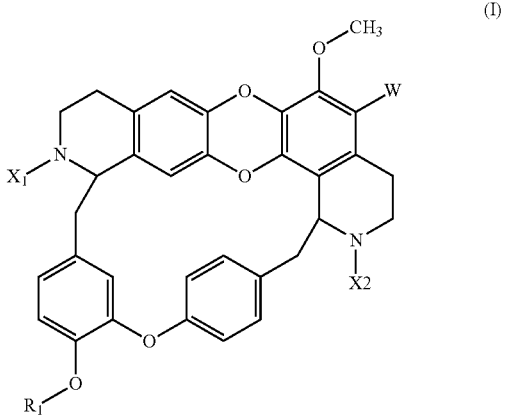

wherein:
W is H,
$X_1$ and $X_2$ are, independently of each other, H, $(C_1-C_{10})$-alkyl, $(C_1-C_{10})$-alkyl-$R_2$, $(C_2-C_{10})$-alkenyl, $(C_2-C_{10})$-alkenyl-$R_2$, $CONR_3R_4$, $CSNR_3R_4$, $COR_3$, $COOR_6$, CN, $SOOR_7$, C(NH)$NHR_3$, $(C_1-C_{10})$-alkyl-$(C_5-C_{10})$-aryl or $(C_1-C_{10})$-alkyl-(5-12)-membered-heterocycle, wherein:
at least one of $X_1$ and $X_2$ is $CONR_3R_4$ or $CSNR_3R_4$,
$R_2$ is OH, O—$(C_1-C_{10})$-alkyl, O—$(C_5-C_{10})$-aryl, $NO_2$, CN, $NR_4R_5$, (5-12)-membered-heterocycle, $(C_5-C_{10})$-aryl, O—$((CH_2)_2O)_n$—OH with n=1-3, $CONR_3R_4$, halogen, $COOR_4$, $CF_3$, or $(C_3-C_{12})$-cycloalkyl, in which $(C_5-C_{10})$-aryl and (5-12)-membered-heterocycle are optionally substituted by at least one group selected from $NR_4R_5$, $OR_5$, $(C_1-C_{10})$-alkyl, halogen and oxo (=O),
$R_3$ is H, or a group chosen among $(C_1-C_{10})$-alkyl, $(C_3-C_{12})$-cycloalkyl, $(C_2-C_{10})$-alkenyl, $(C_5-C_{10})$-aryl and a (5-12)-membered-heteroaryl, said group being optionally substituted by at least one group selected from halogen, CN, $NR_4R_5$, mono($C_1-C_6$)alkyl-amino, di-$(C_1-C_6)$-alkyl-amino, $NO_2$, $CONR_4R_5$, $COOR_4$, $CF_3$, $OR_4$ and $(C_1-C_{10})$-alkyl-$R_8$,
$R_4$ is H or $(C_1-C_{10})$-alkyl,
$R_5$ is H, $(C_1-C_{10})$-alkyl, $(C_5-C_{10})$-aryl or (5-12)-membered-heterocycle,
$R_6$ is H, $(C_1-C_{10})$-alkyl, $(C_5-C_{10})$-aryl or $(C_1-C_{10})$-alkyl-$R_2$,
$R_7$ is $(C_1-C_{10})$-alkyl, $(C_2-C_{10})$-alkenyl, $(C_5-C_{10})$-aryl or a (5-12)-membered-heterocycle, in which the fragments $(C_5-C_{10})$-aryl and (5-12)-membered-heterocycle are optionally substituted by at least one group selected from halogen, CN, $NR_4R_5$, mono($C_1-C_6$)alkyl-amino, di-$(C_1-C_6)$-alkyl-amino, $NO_2$, $CONR_3R_4$, $COOR_4$, $CF_3$ and $OR_4$,
$R_8$ is H, $(C_1-C_{10})$-alkyl, $(C_5-C_{10})$-aryl or (5-12)-membered-heterocycle, in which $(C_5-C_{10})$-aryl and (5-12)-membered-heterocycle are optionally substituted by at least one group selected from $NR_4R_5$, $OR_5$, $(C_1-C_{10})$-alkyl, halogen and oxo,
$R_1$ is hydrogen, $(C_1-C_6)$-alkyl, $COR_6$ or $SOOR_9$ with $R_9$ being a $(C_1-C_6)$-alkyl group optionally substituted by at least one halogen, with the proviso that at least one of $X_1$ and $X_2$ is not H or $(C_1-C_{10})$-alkyl.

2. The compound according to claim 1, having the following formula (Ia) or a pharmaceutically acceptable salt or solvate thereof:

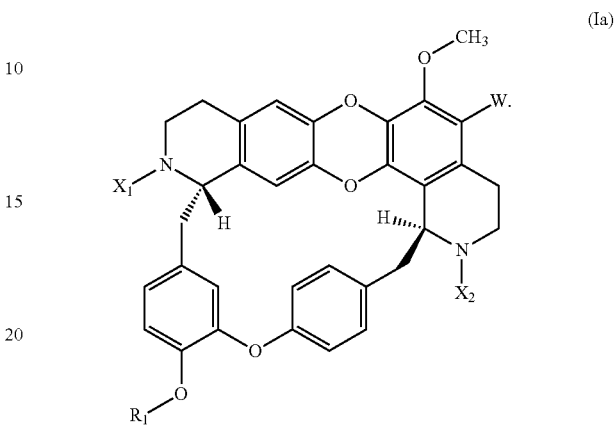

3. The compound according to claim 1, wherein $X_2$ is not H or $(C_1-C_{10})$-alkyl.
4. The compound according to claim 1, wherein $X_2$ is $CONR_3R_4$.
5. The compound according to claim 4, wherein $R_2$ is CN, $NR_4R_5$ or a (5-12)-membered-heterocycle optionally substituted by at least one group selected from $NR_4R_5$, $OR_5$, $(C_1-C_{10})$-alkyl, halogen and oxo (=O).
6. The compound according to claim 1, wherein $R_3$ is H, or a group chosen among $(C_1-C_{10})$-alkyl, $(C_3-C_{12})$-cycloalkyl, $(C_2-C_{10})$-alkenyl and $(C_6-C_{10})$-aryl, said group being optionally substituted by at least one group selected from halogen, $NR_4R_5$, mono-$(C_1-C_6)$-alkyl-amino, di-$(C_1-C_6)$-alkyl-amino, $OR_4$ and $(C_1-C_{10})$-alkyl-$R_8$.
7. The compound according to claim 1, wherein:
$R_4$ is H or $(C_1-C_6)$-alkyl,
$R_5$ is H or $(C_1-C_6)$-alkyl,
$R_6$ is $(C_1-C_6)$-alkyl-$R_2$,
$R_7$ is $(C_1-C_6)$-alkyl,
$R_8$ is a (5-12)-membered-heterocycle, optionally substituted by at least one group selected from $NR_4R_5$, $OR_5$, $(C_1-C_{10})$-alkyl, halogen and oxo.
8. The compound according to claim 1, wherein the (5-12)-membered-heterocycle is:
in the definition of $R_2$, a monocyclic or bicyclic heteroaryl containing 1 to 5 nitrogen atoms, each cycle comprising 5 or 6 members;
in the definition of $R_8$, a saturated, unsaturated or aromatic hydrocarbon monocycle or bicycle, each cycle having 5 or 6 members and 1 to 4 carbon atoms which have been replaced with heteroatoms selected from nitrogen, oxygen and sulfur atoms.
9. The compound according to claim 8, wherein the (5-12)-membered-heterocycle is:
in the definition of $R_2$, a pyrrole, an imidazole, a pyrazole, a pyridine, a pyrimidine, a pyridazine, a pyrazine, an indole, a benzimidazole, a purine, a quinoline, an isoquinoline, a cinnoline, a quinazoline or a quinoxaline;
in the definition of $R_8$, a pyrroline.
10. The compound according to claim 1, selected from the group consisting of compounds of the following formulas:

69                     70
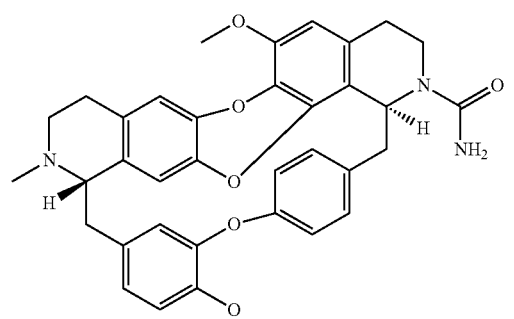
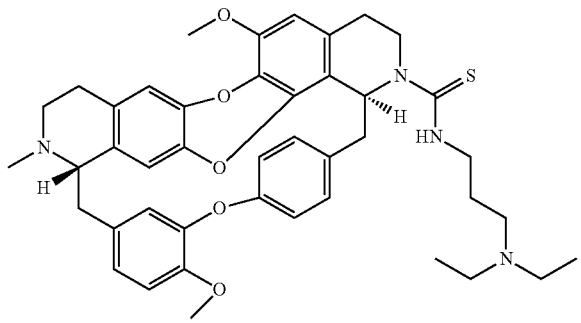
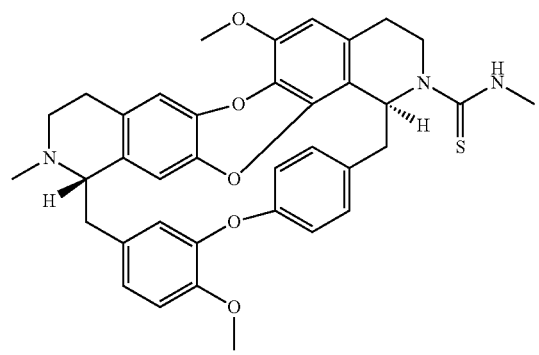
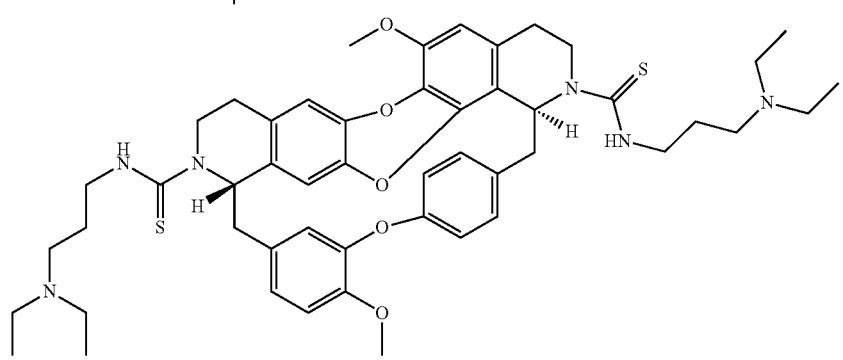
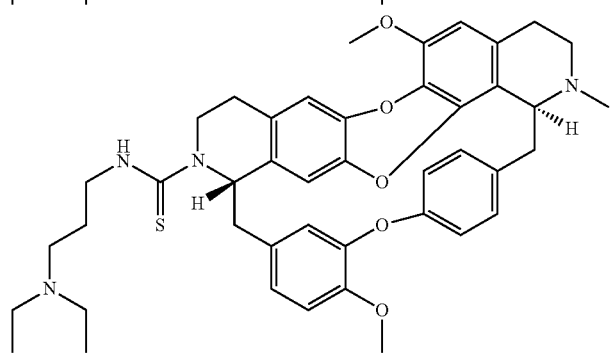
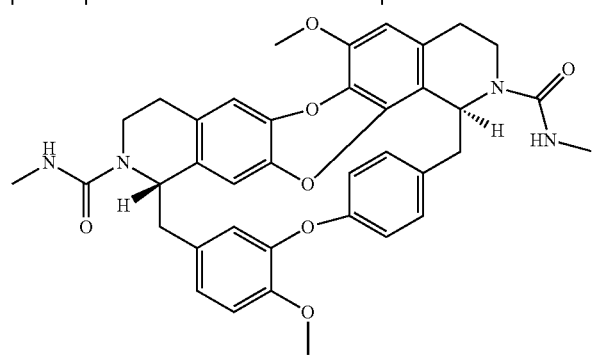
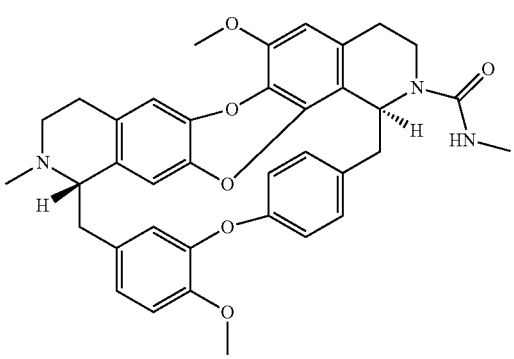

71
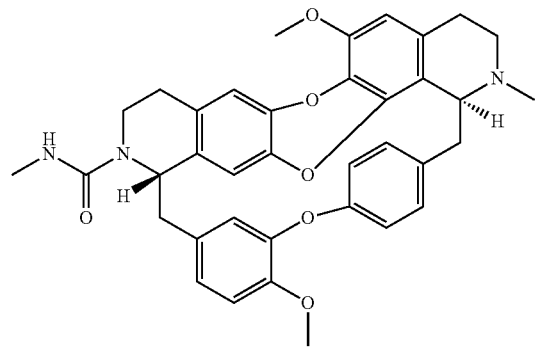
72
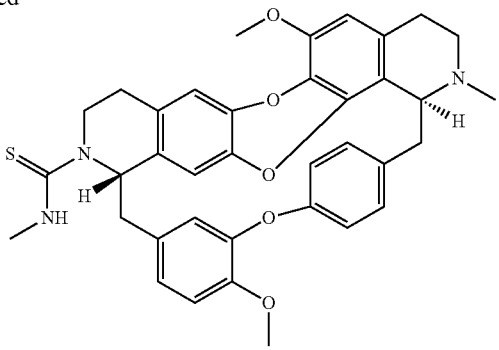
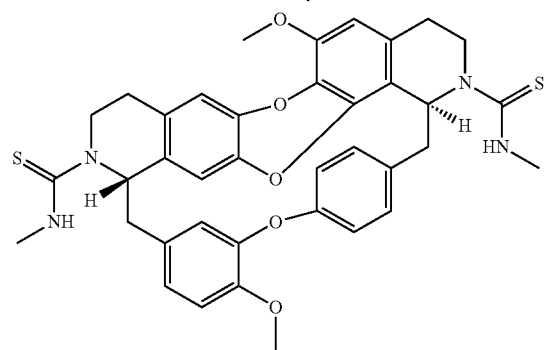
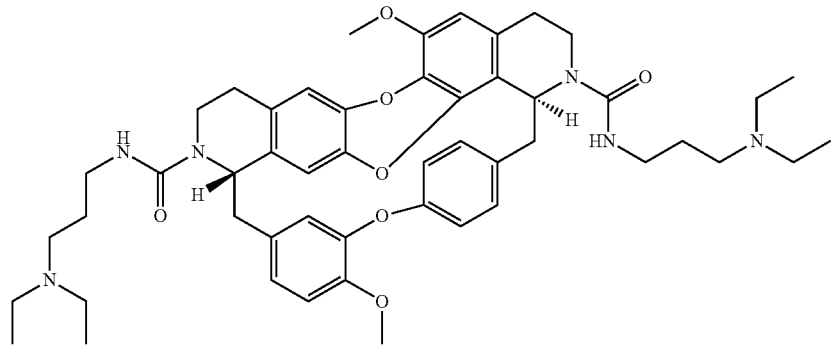
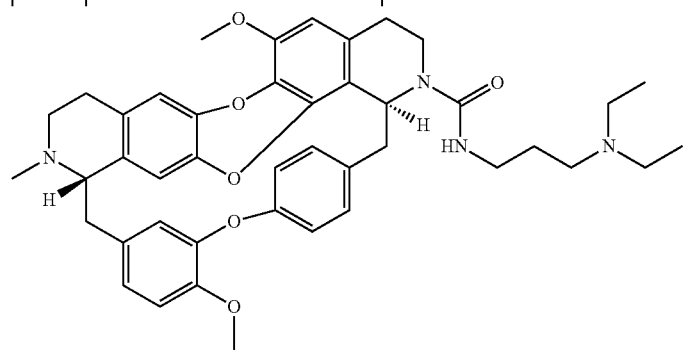
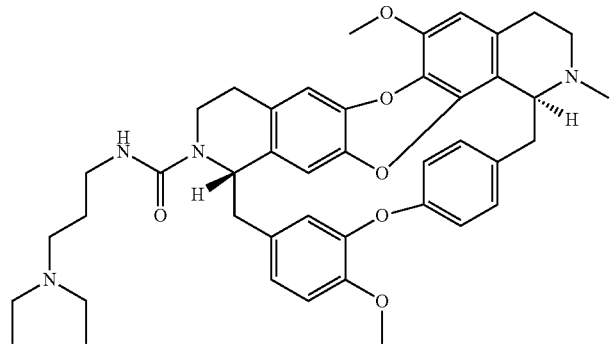
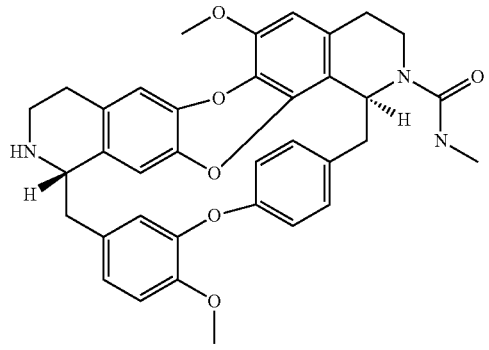

-continued

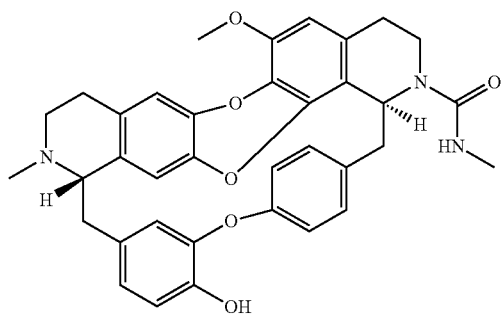

11. A pharmaceutical composition comprising at least one compound according to claim 1, and at least one pharmaceutically acceptable excipient.

12. The pharmaceutical composition according to claim 11, further comprising at least one other active ingredient.

13. The pharmaceutical composition according to claim 12, wherein the at least one other active ingredient is an other anticancer agent.

14. The pharmaceutical composition according to claim 13, wherein said other anticancer agent is selected from the group consisting of cytotoxic agents, immunotherapies and other epigenetics drugs.

15. The pharmaceutical composition according to claim 14, wherein:
cytotoxic agents are selected from doxorubicin, R-CHOP, PARP inhibitors, etoposide, cisplatin, vinerolbine, vinflunine, and bortezomib;
immunotherapies are selected from antiCTL4 and antiPD1; and
other epigenetics drugs are selected from HDACi, inhibitors of chromatin remodeler and inhibitors of histone modifiers.

16. The pharmaceutical composition according to claim 15, wherein:
the HDACi is selected from HDAC 1 & 2;
the inhibitor of chromatin remodeler is CDH4; and
the inhibitor of histone modifiers is selected from demethylases JARDI1A/B and methylases EZH2.

17. A pharmaceutical product comprising:
i. at least one compound according to claim 1, and
ii. at least one other active ingredient,
as a combination product for simultaneous, separate or sequential use in the treatment of cancer.

* * * * *

UNITED STATES PATENT AND TRADEMARK OFFICE
CERTIFICATE OF CORRECTION

PATENT NO. : 10,544,156 B2  
APPLICATION NO. : 15/765048  
DATED : January 28, 2020  
INVENTOR(S) : Ludovic Halby et al.

Page 1 of 1

It is certified that error appears in the above-identified patent and that said Letters Patent is hereby corrected as shown below:

In the Claims

At Column 68, Line 30 (in Claim 5):  
Change:  
"according to claim 4"  
To:  
-- according to claim 1 --

At Column 73, Line 15 (in Claim 10):  
At the end of the claim add:  
-- and the pharmaceutically acceptable salts and solvates thereof. --

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 9

<210> SEQ ID NO 1
<211> LENGTH: 33
<212> TYPE: DNA
<213> ORGANISM: Artificial Sequence
<220> FEATURE:
<223> OTHER INFORMATION: Biotinylated hemimethylated DNA duplex
<220> FEATURE:
<221> NAME/KEY: modified_base
<222> LOCATION: (4)..(4)
<223> OTHER INFORMATION: methylCytosine
<220> FEATURE:
<221> NAME/KEY: modified_base
<222> LOCATION: (7)..(7)
<223> OTHER INFORMATION: methylCytosine
<220> FEATURE:
<221> NAME/KEY: modified_base
<222> LOCATION: (12)..(12)
<223> OTHER INFORMATION: methylCytosine
<220> FEATURE:
<221> NAME/KEY: modified_base
<222> LOCATION: (14)..(14)
<223> OTHER INFORMATION: methylCytosine
<220> FEATURE:
<221> NAME/KEY: modified_base
<222> LOCATION: (19)..(19)
<223> OTHER INFORMATION: methylCytosine
<220> FEATURE:
<221> NAME/KEY: modified_base
<222> LOCATION: (21)..(21)
<223> OTHER INFORMATION: methylCytosine
<220> FEATURE:
<221> NAME/KEY: modified_base
<222> LOCATION: (25)..(25)
<223> OTHER INFORMATION: methylCytosine
<220> FEATURE:
<221> NAME/KEY: modified_base
<222> LOCATION: (30)..(30)
<223> OTHER INFORMATION: methylCytosine

<400> SEQUENCE: 1
gatcgccgat gcgcgaatcg cgatcgatgc gat                                33

<210> SEQ ID NO 2
<211> LENGTH: 33
<212> TYPE: DNA
<213> ORGANISM: Artificial Sequence
<220> FEATURE:
<223> OTHER INFORMATION: Biotinylated hemimethylated DNA duplex
<220> FEATURE:
<221> NAME/KEY: misc_binding
<222> LOCATION: (1)..(1)
<223> OTHER INFORMATION: Biotinylation

<400> SEQUENCE: 2
atcgcatcga tcgcgattcg cgcatcggcg atc                                33

<210> SEQ ID NO 3
<211> LENGTH: 30
<212> TYPE: DNA
<213> ORGANISM: Artificial Sequence
<220> FEATURE:
<223> OTHER INFORMATION: CMV forward primer

<400> SEQUENCE: 3
ggggttatta gtttatagtt tatatatgga                                    30

<210> SEQ ID NO 4
<211> LENGTH: 25
<212> TYPE: DNA
<213> ORGANISM: Artificial Sequence

```
<220> FEATURE:
<223> OTHER INFORMATION: CMV reverse primer

<400> SEQUENCE: 4
aataccaaaa caaactccca ttaac                                              25

<210> SEQ ID NO 5
<211> LENGTH: 18
<212> TYPE: DNA
<213> ORGANISM: Artificial Sequence
<220> FEATURE:
<223> OTHER INFORMATION: M13 forward primer

<400> SEQUENCE: 5
tgtaaaacga cggccagt                                                      18

<210> SEQ ID NO 6
<211> LENGTH: 28
<212> TYPE: DNA
<213> ORGANISM: Artificial Sequence
<220> FEATURE:
<223> OTHER INFORMATION: P16 CDKN2A forward primer

<400> SEQUENCE: 6
ggttttttta gaggatttga gggatagg                                           28

<210> SEQ ID NO 7
<211> LENGTH: 30
<212> TYPE: DNA
<213> ORGANISM: Artificial Sequence
<220> FEATURE:
<223> OTHER INFORMATION: P16 CDKN2A reverse primer

<400> SEQUENCE: 7
ctacctaatt ccaattcccc tacaaacttc                                         30

<210> SEQ ID NO 8
<211> LENGTH: 29
<212> TYPE: DNA
<213> ORGANISM: Artificial Sequence
<220> FEATURE:
<223> OTHER INFORMATION: P15 CDKN2B forward primer

<400> SEQUENCE: 8
tgagatggta gaataaaaat tattaaaaa                                          29

<210> SEQ ID NO 9
<211> LENGTH: 25
<212> TYPE: DNA
<213> ORGANISM: Artificial Sequence
<220> FEATURE:
<223> OTHER INFORMATION: P15 CDKN2B reverse primer

<400> SEQUENCE: 9
aaacaaaaac atacccaata aaac                                               25
```